(12) United States Patent
Rittershaus et al.

(10) Patent No.: US 6,193,979 B1
(45) Date of Patent: *Feb. 27, 2001

(54) COMPOSITIONS COMPRISING COMPLEMENT RECEPTOR TYPE 1 MOLECULES HAVING CARBOHYDRATE STRUCTURES THAT ARE SELECTIN LIGANDS

(75) Inventors: Charles W. Rittershaus, Malden; Carol A. Toth, Sharon, both of MA (US)

(73) Assignee: Avant Immunotherapeutics, Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/450,274

(22) Filed: May 25, 1995

Related U.S. Application Data

(63) Continuation of application No. PCT/US94/05285, filed on May 12, 1994, which is a continuation-in-part of application No. 08/061,982, filed on May 17, 1993, now abandoned.

(51) Int. Cl.$^7$ .................................................. A61K 39/385
(52) U.S. Cl. ..................... 424/195.11; 530/350; 530/395; 530/402
(58) Field of Search .............................. 514/2; 424/184.1, 424/195.11, 193.1; 530/350, 395, 402

(56) References Cited

U.S. PATENT DOCUMENTS

| | | |
|---|---|---|
| 4,752,569 | 6/1988 | Teraski et al. . |
| 5,081,034 | 1/1992 | Bevilacqua et al. . |
| 5,164,374 | 11/1992 | Rademacher et al. . |
| 5,166,133 | 11/1992 | Houston et al. . |
| 5,212,071 | 5/1993 | Fearon et al. . |
| 5,227,369 | 7/1993 | Rosen et al. . |
| 5,856,300 | * 1/1999 | Ritterhaus et al. ..................... 514/12 |

FOREIGN PATENT DOCUMENTS

| | | |
|---|---|---|
| 0 244 267 A3 | 11/1987 | (EP) . |
| 0319 253 A3 | 6/1989 | (EP) . |
| 0 512 733 A2 | 5/1991 | (EP) . |
| W0 91/16900 | 11/1991 | (WO) . |
| WO 91/19501 | 12/1991 | (WO) . |
| WO 91/19502 | 12/1991 | (WO) . |
| WO 92/01718 | 2/1992 | (WO) . |
| WO 92/02527 | 2/1992 | (WO) . |
| WO 92/19735 | 11/1992 | (WO) . |
| WO 94/26786 | 11/1994 | (WO) . |

OTHER PUBLICATIONS

Bevilacqua et al. *J. Clin. Invest.*, 91: 379–387 (1993).
Borman, Stu, "Race Is On To Develop Sugar–Based Anti–inflammatory, Antitumor Drugs", C&EN, Dec. 7, 1992, pp. 25–28.
Brustein et al., *J. Exp. Med.*, 176: 1415–1419 (1992).
Butcher, Eugene C., *Cell*, 67: 1033–1036 (Dec. 20, 1991).
Campbell et al., *J. Bio. Chem.*, 259: 11208–11214 (1984).
Goochee et al., *Bio/Technology*, 9: 1347–1355 (1991).
Howard et al., *J. Bio. Chem.*, 262: 16830–16837 (1987).
Imai et al., *Nature*, 361: 555–557 (1993).
Kobata et al., *Eur. J. Biochem.*, 209: 483–501 (1992).
Larsen et al., *Cell*, 59: 305–312 (1989).
Makrides et al., *J. Bio Chem.*, 267(34): 24754–24761 (1992).
Mulligan et al., *J. Clin. Invest.*, 90: 1600–1607 (1992).
Mulligan et al., *J. Immunol.*, 150(6): 2401–2406 (1993).
Nelson et al., *J. Clin. Invest.*, 91: 1157–1166 (1993).
Norgard et al., *Proc. Acad. Sci. USA*, 90: 1068–1072 (1993).
Paulson, James C., *TIBS*, 14: 272–276 (1989).
Philips et al., *Science*, 250: 1130–1135 (1990).
Potvin et al., *J. Bio. Chem.*, 265(3): 1615–1622 (1990).
Shandelya et al., *Circulation*, 87(2): 536–545 (1993).
Sharon et al., *Scientific American*, pp. 82–88 (Jan. 1993).
Skubitz et al., *J. Immunol.*, 139(5): 1631–1639 (1987).
Stanley et al., *J. Bio. Chem.*, 263(23): 11374–11381 (1988).
Stanley, Pamela, *Somatic Cell Genetics*, 9(5): 593–608 (1983).
Walz et al., *Science*, 250:1132–1135 (1990).
Yeh et al. (Jan. 1, 1991) J. Immunol. vol. 146(1):250–6.*
Mulligan et al. (Mar. 1, 1992) J. Immunol. vol. 148(5):1479–85.*
Kalli et al. (Dec. 1, 1991) J. Exp. Med. vol. 174(6):1451–60.*
Fearon (Oct. 1991) Clin. Exp. Immunol. vol. 86(Suppl. 1):43–6.*
Foxall et al. (May 1992) J. Cell. Biol. vol. 117(4) 895–902.*

* cited by examiner

*Primary Examiner*—Patrick Nolan
(74) *Attorney, Agent, or Firm*—Leon R. Yankwich; David G. O'Brien

(57) ABSTRACT

The present invention provides compositions comprising at least one complement moiety and at least one carbohydrate moiety, and methods of producing such compositions. In particular, the compositions of the invention comprise complement proteins related to the complement receptor type 1, and further comprise ligands for intercellular molecules, such as selectins. In a preferred embodiment, the compositions comprise a complement-related protein in combination with the Lewis X antigen or the sialyl Lewis X antigen. The compositions of the invention have use in the diagnosis or therapy of disorders involving complement activity and inflammation. Pharmaceutical compositions are also provided for treating or reducing inflammation mediated by inappropriate complement activity and intercellular adhesion.

28 Claims, 8 Drawing Sheets

SEQUENCE LISTING (1) GENERAL INFORMATION:

(iii) NUMBER OF SEQUENCES:11

(2) INFORMATION FOR SEQ ID NO: 1:

(i) SEQUENCE CHARACTERISTICS:
      (A) LENGTH: 68 base pairs
      (B) TYPE:nucleic acid
      (C) STRANDEDNESS: single
      (D) TOPOLOGY: linear (ii) MOLECULE TYPE:DNA (xi) SEQUENCE DESCRIPTION: SEQ ID NO: 1:

CGCCCGGTCT CCCCTTCTGC TGCGGAGGAT 30

CCCTGCTGGC GGTTGTGGTG CTGCTTGCGG 60

TGCCGGTG 68

(2) INFORMATION FOR SEQ ID NO:    2:

(i) SEQUENCE CHARACTERISTICS:
      (A) LENGTH:72 base pairs
      (B) TYPE:nucleic acid
      (C) STRANDEDNESS:single
      (D) TOPOLOGY:linear (ii) MOLECULE TYPE:DNA (xi) SEQUENCE DESCRIPTION: SEQ ID NO: 2:

CCAGGCCACC GGCAGCGCAA GCAGCACCAC 30

AACCGCCAGC AGGGATCCTC CGCAGCAGAA 60

GGGGAGACCG GG 72

(2) INFORMATION FOR SEQ ID NO: 3:

(i) SEQUENCE CHARACTERISTICS:
      (A) LENGTH:66 base pairs
      (B) TYPE:nucleic acid
      (C) STRANDEDNESS:single
      (D) TOPOLOGY:linear (ii) MOLECULE TYPE:DNA (xi) SEQUENCE DESCRIPTION: SEQ ID NO: 3:

GCCTGGGGTC AATGTCAAGC CCCAGATCAT 30

```
TTTCTGTTTG CCAAGTTGAA AACCCAAACC                              60

AATGCA                                                        66

(2) INFORMATION FOR SEQ ID NO: 4:

(i) SEQUENCE CHARACTERISTICS:
        (A) LENGTH:56 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO: 4:

TTGGTTTGGG TTTTCAACTT GGCAAACAGA                              30

AAATGATCTG GGGCTTGACA TTGACC                                  56

(2) INFORMATION FOR SEQ ID NO: 5:

(i) SEQUENCE CHARACTERISTICS:
        (A) LENGTH:31 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO: 5:

CCCCCCCTCG AGGTCGACGG TATCGATAAG                              30

C                                                             31

(2) INFORMATION FOR SEQ ID NO: 6:

(i) SEQUENCE CHARACTERISTICS:
        (A) LENGTH:56 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO: 6:

TATCAAATGC GGCCGCTAAG AATACCCTAG                              30

ATCTGGAGCA GCTTGGTAAC TCTGGC                                  56

(2) INFORMATION FOR SEQ ID NO: 7:

(i) SEQUENCE CHARACTERISTICS:
        (A) LENGTH:19 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO: 7:

GATGAACTAG TCTCGAGAG                                          19

(2) INFORMATION FOR SEQ ID NO: 8:

(i) SEQUENCE CHARACTERISTICS:
        (A) LENGTH:19 base pairs
        (B) TYPE:nucleic acid
        (C) STRANDEDNESS:single
        (D) TOPOLOGY:linear
```

-continued (ii) MOLECULE TYPE:DNA (xi) SEQUENCE DESCRIPTION: SEQ ID NO: 8:

CTCTCGAGAC TAGTTCATC                                                19

(2) INFORMATION FOR SEQ ID NO: 9:

(i) SEQUENCE CHARACTERISTICS:
      (A) LENGTH:40 base pairs
      (B) TYPE:nucleic acid
      (C) STRANDEDNESS:single
      (D) TOPOLOGY:linear (ii) MOLECULE TYPE:DNA (xi) SEQUENCE DESCRIPTION: SEQ ID NO: 9:

CGACACTTGA AAGACAAGCG CTACCAGTGA                                     30

CATTTTGGGG                                                           40

(2) INFORMATION FOR SEQ ID NO: 10:

(i) SEQUENCE CHARACTERISTICS:
      (A) LENGTH:13 base pairs
      (B) TYPE:nucleic acid
      (C) STRANDEDNESS:single
      (D) TOPOLOGY:linear (ii) MOLECULE TYPE:DNA (xi) SEQUENCE DESCRIPTION: SEQ ID NO: 10:

CGCTTAAGCT CGA                                                       13

(2) INFORMATION FOR SEQ ID NO: 11:

(i) SEQUENCE CHARACTERISTICS:
      (A) LENGTH:17 base pairs
      (B) TYPE:nucleic acid
      (C) STRANDEDNESS:single
      (D) TOPOLOGY:linear (ii) MOLECULE TYPE:DNA (xi) SEQUENCE DESCRIPTION: SEQ ID NO: 11:

GATCTCGAGC TTAAGCG                                                   17

COMPOSITIONS COMPRISING COMPLEMENT RECEPTOR TYPE 1 MOLECULES HAVING CARBOHYDRATE STRUCTURES THAT ARE SELECTIN LIGANDS

This is a continuation of international application No. PCT/US94/05285, filed May 12, 1994 and designating the United States, which is a CIP of U.S. application Ser. No. 08/061,982, filed May 17, 1993 and now abandoned.

1. FIELD OF THE INVENTION

In its broadest aspect, the present invention provides compositions comprising at least one complement moiety and at least one carbohydrate moiety, and methods of producing such compositions. In particular, the compositions of the invention comprise complement proteins related to the complement receptor type 1, and further comprise ligands for intercellular adhesion molecules, such as selectins. In a preferred embodiment, the compositions comprise a complement receptor type 1, or fragment or derivative thereof, in combination with the Lewis X antigen or the sialyl Lewis X antigen. The compositions of the invention have use in the diagnosis or therapy of disorders involving complement activity and inflammation. Pharmaceutical compositions are also provided for treating or reducing inflammation mediated by inappropriate complement activity and intercellular adhesion.

2. BACKGROUND OF THE INVENTION
2.1. THE COMPLEMENT SYSTEM

The complement system is a group of proteins that constitute about 10 percent of the globulins in the normal serum of humans (Hood, L. E., et al., 1984, Immunology, 2d Ed., The Benjamin/Cummings Publishing Co., Menlo Park, Calif., p. 339). Complement (C) plays an important role in the mediation of immune and allergic reactions (Rapp, H. J. and Borsos, T, 1970, Molecular Basis of Complement Action, Appleton-Century-Crofts (Meredity), New York). The activation of complement components leads to the generation of a group of factors, including chemotactic peptides that mediate the inflammation associated with complement dependent diseases. The sequential activation of the complement cascade may occur via the classical pathway involving antigen-antibody complexes, or by the alternative pathway which involves the recognition of foreign structures such as, certain cell wall polysaccharides. The activities mediated by activated complement proteins include lysis of target cells, chemotaxis, opsonization, stimulation of vascular and other smooth muscle cells, and functional aberrations such as degranulation of mast cells, increased permeability of small blood vessels, directed migration of leukocytes, and activation of B lymphocytes and macrophages (Eisen, H. N., 1974, Immunology, Harper & Row Publishers, Inc. Hagerstown, Md., p. 512).

During proteolytic cascade steps, biologically active peptide fragments, the anaphylatoxins C3a, C4a, and C5a (See WHO Scientific Group, 1977, WHO Tech Rep. Ser. 606:5 and references cited therein), are released from the third (C3), fourth (C4), and fifth (C5) native complement components (Hugli, T. E., 1981, CRC Crit. Rev. Immunol. 1:321; Bult, H. and Herman, A. G., 1983, Agents Actions 13:405).
2.2. COMPLEMENT RECEPTORS COMPLEMENT RECEPTOR 1 (CR1). The human C3b/C4b receptor, termed CR1 or CD35, is present on erythrocytes, monocytes/macrophages, granulocytes, B cells, some T cells, splenic follicular dendritic cells, and glomerular podocytes (Fearon D. T., 1980, J. Exp. Med. 152:20, Wilson, J. G., et al., 1983, J. Immunol. 131:684; Reynes, M., et al., 1976 N. Engl. J. Med. 295:10; Kazatchkine, M. D., et al., 1982, Clin. Immunol. Immunopathol. 27:210). CR1 specifically binds C3b, C4b and iC3b.

CR1 can inhibit the classical and alternative pathway C3/C5 convertases and act as a cofactor for the cleavage of C3b and C4b by factor I, indicating that CR1 also has complement regulatory functions in addition to serving as a receptor (Fearon, D. T., 1979, Proc. Natl. Acad. Sci. U.S.A. 76:5867; Iida, K. I. and Nussenzweig, V., 1981, J. Exp. Med. 153:1138). In the alternative pathway of complement activation, the bimolecular complex C3b,Bb is a C3 enzyme (convertase). CR1 (and factor H, at higher concentrations) can bind to C3b and can also promote the dissociation of C3b,Bb. Furthermore, formation of C3b,CR1 (and C3b,H) renders C3b susceptible to irreversible proteolytic inactivation by factor I, resulting in the formation of inactivated C3b (iC3b). In the classical pathway of complement activation, the complex C4b,2a is the C3 convertase.

CR1 (and C4 binding protein, C4bp, at higher concentrations) can bind to C4b, and can also promote the dissociation of C4b,2a. The binding renders C4b susceptible to irreversible proteolytic inactivation by factor I through cleavage to C4c and C4d (inactivated complement proteins).

CR1 has been shown to have homology to complement receptor type 2 (CR2) (Weis, J.J., et al., 1986, Proc. Natl. Acad. Sci. U.S.A. 83:5639–5643). CR1 is a glycoprotein comprising multiple short consensus repeats (SCRs) arranged in 4 long homologous repeats (LHRs). The most C-terminal LHR called LHR-D is followed by 2 additional SCRs, a transmembrane region and a cytoplasmic region (Klickstein, et al., 1987, J. Exp. Med., 165:1095; Klickstein, et al. 1988, J. Exp. Med., 168:1699–1717). Erythrocyte CR1 appears to be involved in the removal of circulating immune complexes in autoimmune patients and its levels may correlate with the development of AIDS (Inada, et al., 1986, AIDS Res. 2:235; Inada, et al., 1989, Ann. Rheu. Dis. 4:287).

Four allotypic forms of CR1 have been found, differing by increments of 40,000–50,000 daltons molecular weight. The two most common forms, the F and S allotypes, also termed the A and B allotypes, have molecular weights of 250,000 and 290,000 daltons respectively, (Dykman, T. R., et al., 1983, Proc. Natl. Acad. Sci. U.S.A. 80:1698; Wong, W. W., et al., 1983, J. Clin. Invest. 72:685), and two rarer forms have molecular weights of 210,000 and 290,000 daltons (Dykman, T. R., et al., 1984, J. Exp. Med. 159:691; Dykman, T. R., et al., 1985, J. Immunol. 134:1787). These differences apparently represent variations in the polypeptide chain of CR1, rather than glycosylation state, because they were not abolished by treatment of purified receptor protein with endoglycosidase F (Wong, W. W., et al., 1983, J. Clin. Invest. 72:685), and they were observed when receptor allotypes were biosynthesized in the presence of the glycosylation inhibitor tunicamycin (Lublin, D. M., et al., 1986, J. Biol. Chem. 261:5736). All four CR1 allotypes have C3b-binding activity (Dykman, T. R., et al., 1983, Proc. Natl. Acad. Sci. U.S.A. 80:1698; Wong, W. W., et al., 1983, J. Clin. Invest. 72:685; Dykman, T. R., et al., 1984, J. Exp. Ned., 159:691; Dykman, T. R., et al., 1985, J. Immunol. 134:1787). There are four LHRs in the F (or A) allotype of ~250 kD, termed LHR-A, -B, -C, and -D, respectively, 5' to 3' (Wong, et al., 1989, J. Exp. Med. 169:847). While the first two SCRs in LHR-A determine its ability to bind C4b, the corresponding units in LHR-B and -C determine their higher affinities for C3b. The larger S (or B) allotype of ~290 kd has a fifth LHR that is a chimera of the 5' half of LHR-B and the 3' half of LHR-A and is predicted to contain a third C3b binding site (Wong, et al., 1989, J. Exp. Med. 169:847). The smallest F' (or C) allotype of CR1 of ~210 kD, found in increased incidence in patients with systemic lupus erthematosis (SLE) and associated with patients in multiple lupus families (Dykman, et al., 1984, J. Exp. Med. 159:691; Van Dyne, et al., 1987, Clin. Exp. Immunol. 68:570), may have resulted from the deletion of one LHR and may be impaired in its capacity to bind efficiently to immune complexes coated with complement fragments.

A naturally occurring soluble form of CR1 has been identified in the plasma of normal individuals and certain individuals with SLE (Yoon, et al., 1985 J. Immunol. 134:3332–3338). Its structural and functional characteristics are similar to those of erythrocyte (cell surface) CR1, both structurally and functionally. Hourcade, et al. (1988, J. Exp. Med. 168:1255–1270) also observed an alternative polyadenylation site in the human CR1 transcriptional unit that was predicted to produce a secreted form of CR1 containing the C4b binding domain.

Several soluble fragments of CR1 have also been generated via recombinant DNA procedures by eliminating the transmembrane region from the DNAs being expressed (Fearon, et al., International Patent Publication No. WO89/09220, Oct. 5, 1989; Fearon, et al., International Patent Publication No. WO91/05047, Apr. 18, 1991). The soluble CR1 fragments were functionally active, bound C3b and/or C4b and demonstrated factor I cofactor activity, depending upon the regions they contained. Such constructs inhibited in vitro the consequences of complement activation such as neutrophil oxidative burst, complement mediated hemolysis, and C3a and C5a production. A soluble construct sCR1/pBSCR1c, also demonstrated in vivo activity in a reversed passive Arthus reaction (Fearon, et al., 1989, supra; Fearon, et al., 1991, supra; Yeh, et al., 1991 supra), suppressed post ischemic myocardial inflammation and necrosis (Fearon, et al., $^{1989}$, supra; Fearon, et al., 1991, supra; Weismann, et al., 1990, Science, 249:146–151) and extended survival rates following transplantation (Pruitt and Bollinger, 1991, J. Surg. Res. 50:350; Pruitt, et al., 1991, Transplantation 52:868). [Mulligan et al, 1992, J. Immunol. 148:3086–3092 (injury following immune complex deposition). Mulligan, et al., 1992, J. Immunol. 148:1479–1485 (protection from neutrophil mediated tissue injury). Lindsay, et al., 1992, Annals of Surg. 216:677. , Hill, et al., 1992, J. Immunol. 149:1722–1728 (tissue ischemia reperfusion injuries)].

CR2. Complement receptor type 2 (CR2, CD21) is a transmembrane phosphoprotein consisting of an extracellular domain which is comprised of 15 or 16 SCRs, a 24 amino acid transmembrane region, and a 34 amino acid cytoplasmic domain (Moore, et al., 1987, Proc. Natl. Acad. Sci. U.S.A. 84:9194–9198; Weis, et al., 1988, J. Exp. Med. 167:1047–1066). Electron microscopic studies of soluble recombinant CR2 have shown that, like CR1, it is an extended, highly flexible molecule with an estimated contour length of 39.6 nanometers by 3.2 nanometers, in which each SCR appears as a ringlet 2.4 nanometers in length (Moore, et al., 1989, J. Biol. Chem. 34:20576–20582).

By means of recombinant DNA experiments with eukaryotic expression vectors expressing deletion or substitution mutants of CR2 in COS cells, the ligand 30 binding sites of CR2 have been localized to the two N-terminal SCR's of the molecule (Lowell, et al., 1989, J. Exp. Med. 170:1931–1946). Binding by cell surface CR2 of the multivalent forms of C3 ligands such as iC3b and C3dg causes activation of B-cells (Melchers, et al., 1985, Nature, 317:264–267; Bohnsack, et al., 1988, J. Immunol. 141:457–463; Carter, et al., 1988, J. Immunol. 143:1755–1760).

A form of recombinant soluble CR2 has been produced (Moore, et al., 1989, J. Biol. Chem. 264:20576–20582). In analogy to the soluble CR1 system, soluble CR2 was produced in a recombinant system from an expression vector containing the entire extracellular domain of the receptor, but without the transmembrane and cytoplasmic domains. This recombinant CR2 is reported to bind to C3dg in a 1:1 complex with Kd equal to 27.5 mM and to bind to the Epstein-Barr proteins gp350/220 in a 1:1 complex with a Kd of 3.2 nM (Moore, et al., 1989, J. Biol. Chem. 264:20576–20582).

CR3. A third complement receptor, CR3, also binds iC3b. Binding of iC3b to CR3 promotes the adherence of neutrophils to complement-activating endothelial cells during inflammation (Marks, et al., 1989, Nature 339:314). CR3 is also involved in phagocytosis, where particles coated with iC3b are engulfed by neutrophils or by macrophages (Wright, et al., 1982, J. Exp. Med. 156:1149; Wright, et al., 1983, J. Exp. Med. 158:1338).

CR4. CR4(CD11) also appears to be involved in leukocyte adhesion (Kishimoto, et al., 1989, Adv. Immunol. 46:149–82).

DAF. DAF, or decay-accelerating factor, is a membrane protein that appears to have similar action to C4Bp in bringing about a functional-dissociation of C2b from C4b. DAF is linked to membranes via a phosphatidyl inositol glycolipid, and its absence from red blood cells has been shown to be a major causative factor in paroxysmal nocturnal hemoglobinuria. (Encyclopedia of Human Biology, Academic Press, Inc. 1991). DAF binds to C3b/C4b as well as C3 convertases (EP 0512 733 A2).

DAF contains 4 SCRs followed by an O-linked glycosylation region, and is terminated with a glycolipid anchor (EP 0512 733 A2). Cells that express DAF show substantial increases in resistance to complement-mediated cell lysis (Lublin, D. M. et al., 1991, J. Exp. Med. 174:35; Oglesby, T. J., et al., 1991; Trans. Assoc. Am. Phys. CIV:164–172; White, D. J. G., et al., 1992; Transplant Proc. 24:474–476).

MCP. MCP or membrane cofactor protein, like DAF, contains 4 SCRs followed by an O-linked glycosylation region. MCP is terminated witn an extra cytoplasmic segment (whose importance is unknown) a transmembrane region and an intracellular domain (EP 0512 733 A2). Also, like DAF, cells expressing NCP confer substantial increases in resistance to complement-mediated cell lysis. (EP 0512 733 A2 and Lublin, D. M., et al., J. Exp Med (19) 174:35; Oglesby, T. J. et al., Trans Assoc Am Phys (1991) CIV:164–172; White, D. J. G., et al., Transplant Proc (1992) 24:474–476).

FACTOR H. Factor H is a plasma protein that is exclusively or predominantly composed of SCRs (Chung, L. P., et al., 1985, Biochem. J. 230:133; Kristensen, T., et al., 1986, J. Immunol. 136:3407). Factor H is a regulator of the alternative pathway. Factor H binds to C3b and to the C3b portion of C3 convertases (C3b, Bb) (Encyclopedia of Human Biology, supra) accelerating dissociation of Bb from these complexes thereby inactivating them. Factor H also regulates the use of C5 in the classical pathway by competing with C5 for binding to C3b, thus inactivating the activity of the C3/C5 convertase (Encyclopedia of Human Biology, supra).

2.3. SELECTINS AND SELECTIN LIGANDS

Selectins are a group of cell surface glycoproteins which characteristically display a $NH_2$ terminal lectin domain related to the carbohydrate recognition structure described for animal lectins, an epidermal growth factor domain, and a domain consisting of short repeating sequences analogous to those found in the complement regulatory proteins which map to a region of chromosome 1 called the regulators of complement activity (RCA) (Harlan & Liu, Adhesion: Its Role in Inflammatory Disease, W. H. Freeman & Co., 1992). Three independently studied selecting have been characterized and are named according to the cell type upon which each was originally identified. Under the current nomenclature there are the E-selectins, originally identified on cytokine-activated endothelial cells (Bevilacque, M. P. et al., (1985) J. Clin. Invest. 76:2003–2011); P-selectins, discovered on activated platelets (Hsu-Lin, P. E., et al. (1984) J. Biol. Chem. 259:9121–9126); and finally, L-selectins recognized as a cell surface marker on most leukocytes including lymphocytes, neutrophils, and monocytes (Kansas, G. S. et al., (1985) J. Immunol. 134:2995–3002). Each selectin has been implicated as a key factor in important events in cellular adhesion and recognition. As such, their carbohydrate recognition structures at the $NH_2$-terminal portion of the molecule as well as their carbohydrate ligands have been extensively studied.

Selectins, then, are cell adhesion molecules that in inflammatory situations are responsible for the attachment of platelets and leukocytes to vascular surfaces and their subsequent infiltration into the tissue. During a normal inflammatory response the leukocytes, in responding to various signals, enter the tissue and phagocytize invading organisms. In various pathologic inflammatory diseases, such as psoriasis and rheumatoid arthritis, this response may lead to serious organ tissue damage. Similarly, in reperfusion injury, invading leukocytes are responsible for tissue damage. And, aside from their involvement in inflammation, cell adhesion molecules on selecting play a central role in other diseases such as tumor metastasis.

In inflammatory situations, all three selecting are implicated in the recruitment of leukocytes to the site of inflammation. Early events in the inflammatory response include the recruitment of neutrophils to the site of tissue damage. In normal situations, circulating lymphocytes bind to the vascular endothelium with low avidity. Under situations of distress however, as when the body has been invaded by a bacterial pathogen or when tissue damage has occurred, leukocytes interact with the activated endothelium in another manner. First, up regulation of selecting on endothelial cells and platelets occurs to control the localization of leukocytes to the inflamed endothelium. The initial step of attachment of neutrophils to the endothelial cells lining the venules is controlled by selecting and is known as neutrophil "rolling" (von Andrian, U. H. et al., (1991) Proc. Natl. Acad. Sci., U.S.A. 88:7538–7542; Smith, C. W., et al., (1991) J. Clin. Invest., 87:609–618). This "rolling" precedes the firm adhesion of leukocytes, especially neutrophils to the endothelium which is controlled by a different class of receptors known as the integrins. (Lawrence, M. B. and Springer, T. S. (1991) Cell 65: 859–873; von Andrain, U. H. et al., (1991) Proc. Natl. Sci. U.S.A. 88:7538–7542; Larson R. S. and Springer, T. A. (1990) Immunol. Rev. 114:181–217). Extravasation of the cells into the surrounding tissue proceeds after the aforementioned attachment processes have each been accomplished.

One of the selecting, E-selectin (ELAM-1, endothelial cell adhesion molecule, LECCAM-2) is expressed on endothelial cells following induction by cytokines such as interleukin-1β, tumor necrosis factor-α, lymphotoxin, bacterial endotoxins, interferon-γ and the neuropeptide substance-p (Harlan & Liu, supra). The expression of E-selectin on activated endothelium requires de novo synthesis, peaks at 4–6 hours, and persists from 2–48 hours after initial stimulus. Activated endothelia expressing the ELAM-1 receptor have been shown to bind neutrophils (Bevilacque M. P., et al. (1987) Proc. Natl. Acad. Sci. U.S.A. 84:9238–9242); monocytes (Walz, G. et al., (1990) Science 250: 1132–1135): eosinophil (Kyan-Aung (1991) J. Immunol. 146:521–528): and NK cells (Goelz, S. E. (1990) Cell 63:1149–1356). Additionally, activated endothelium binds some carcinoma cells (Rice, G. E. and Bevilacqua M. P. (1989) Science 246:1303–1306; Walz, G. et al., (1990) 250 1132–1135) implicating a role for E-selectins in attachment of tumor cells to blood vessel walls.

P-selectin (CD62, granule membrane protein-140, GMP-140, platelet activation dependent granule external membrane, Padgem, LECCAM-3) is expressed on activated platelets as well as endothelial cells. The P-selectin expression can be mobilized from intracellular stores in minutes after activation. P-selectins bind neutrophils and monocytes, as well as carcinoma cells (Walz, G., et al., (1990) 250:1132–1135).

P-selectin, or CD62 expression does not require de novo synthesis because this selectin is stored in secretory granules, also called Weibel-Palade bodies, in both platelets and endothelial cells. Thus, within minutes of activation of either cell type, for example by thrombin, histamine, or phorbol esters, CD62 is rapidly transported to the surface of the cell where it can bind the ligand found on neutrophils, monocytes, and other cells, These ligand-bearing cells then adhere to the platelet or endothelial cells expressing the CD62 receptor.

Patel et al. have found that endothelial cells also express CD62 in response to low levels of hydrogen peroxide or other oxidizing agents through the production of free radicals (Patel et al., 1991, J. Cell Biol. 112:749–759). While endothelial cells normally reinternalize CD62 within minutes of activation, induction by free radicals produces prolonged expression of the selectin. Because neutrophils release oxidizing agents and free radicals following activation, initial recruitment of neutrophils by transiently expressed CD62 could effectively prolong the expression of CD62 through free radical generation by neutrophils (Harlan & Liu, Adhesion, supra).

L-selectin, (lymphocyte homing receptor, LECCAM-1, Mel-14, Leu-8, TQ-1, Ly-22, LAM-1) is constitute expressed on the cell surface and is shed after activation (Jung. T. M. et al., (1988) J. Immunol., 141:4110–4117).

Recent advancements in the field of adhesion molecules have led to the understanding of the role of protein-carbohydrate interactions. In particular, the ligands for selectins have been recently studied (Bevilaque, M. P. and Nelson, R. M. (1993) J. Clin. Invest. 91: 379–387). Among the ligands identified are the Lewis X blood antigen ($Le^x$) and sialylated Lewis X antigen. The Lewis X antigens have been known for some time, and had been identified as the terminal structures on cell surface glycoproteins and glycolipids or neutrophils and promyelocytic cell lines (Harlan & Liu, Adhesion, supra).

Lowe et al. demonstrated that transfection of a cDNA for the Lewis blood group fucosyl transferase (Galβ1,3/4GlcNAcα1,3 fucosyltransferase) into Chinese hamster ovary (CHO) cells resulted in the expression of the $Le^x$ and $SLe^x$ antigens and the simultaneous ability of the transfected cells to adhere to E-selectins on TNF-α-activated human umbilical vein endothelial cells (HUVECs) (Lowe et al., 1990, Cell 63:475–484). Sialidase treatment of the cells abolished their ability to adhere to activated HUVECs, indicating that a sialylated structure was required for adhesion. Additionally, it was observed that a pre-myelocytic leukemia-60 (HL-60) cell clone which expressed $SLe^x$ bound to HUVECS while another clone that did not express $SLe^x$ did not bind to HUVECS.

Phillips et al. produced CHO glycosylation mutants, which, unlike the wild-type cells, expressed fucosyltransferase activities that synthesized both $Le^x$ and $SLe^x$ (LEC11) or $Le^x$ only (LEC12) as terminal sugar structures on cell surface glycoproteins (Phillips et al., 1990 Science 250:1130–1132). Only LEC11 cells bound to E-selectin on activated HUVECs, and the adhesion was abolished by pretreatment of the LEC11 cells with sialidase, implicating $SLe^x$ as the ligand.

The nucleic acid sequence of an α1,3-fucosyl transferase responsible for adding a fucosyl residue to an appropriate carbohydrate such as ELAM, through an α1,3 glycosidic linkage has been reported (International Patent Publication No. WO91/16900). This report also describes recombinant COS and CHO cells transformed with the transferase.

Other ligands that bind to selectins have also been disclosed. These ligands structurally resemble the Lewis X antigens (International Patent Publication No. WO92/02527 and International Patent Publication No. WO91/19502).

2.4. DISEASES INVOLVING INAPPROPRIATE COMPLEMENT ACTIVITY

Diminished expression of CR1 on erythrocytes of patients with systemic lupus erythematosus (SLE) has been reported by investigators from several geographic regions, including Japan (Miyakawa, et al., 1981, Lancet 2:493–497; Minota, et al., 1984, Arthr. Rheum. 27:1329–1335), the United States (Iida, et al., 1982, J. Exp. Med. 155:1427–1438; Wilson, et al., 1982, N. Engl. J. Med. 307:981–986) and Europe (Walport, et al., 1985, Clin. Exp. Immunol. 59:547; Jouvin, et al., 1986, Complement 3:88–96; Holme, et al., 1986, Clin. Exp. Immunol. 63:41–48). CR1 number has also been found to correlate inversely with serum levels of immune complexes, with serum levels of C3d, and with the amounts of erythrocyte-bound C3dg, perhaps reflecting uptake of complement-activating immune complexes and deposition on the erythrocyte as an "innocent bystander" (Ross, et al., 1985, J. Immunol. 135:2005–2014; Holme, et al., 1986, Clin. Exp. Immunol. 63:41–48; Walport, et al., 1985, Clin. Exp. Immunol. 59:547).

Abnormalities of complement receptor expression in SLE are not limited to erythrocyte CR1. Relative deficiencies of total cellular CR1 of neutrophils and plasma membrane CR1 of B lymphocytes of the SLE patients have been shown to occur (Wilson, et al., 1986, Arthr. Rheum. 29:739747).

The relative loss of CR1 from erythrocytes has also been observed in patients with Human Immunodeficiency Virus (HIV) infections (Tausk, F. A., et al., 1986, J. Clin. Invest. 78:977–982) and with lepromatous leprosy (Tausk, F. A., et al., 1985, J. Invest. Dermat. 85:58s–61s).

Complement activation has also been associated with disease states involving inflammation. The intestinal inflammation of Crohn's disease is characterized by the lymphoid infiltration of mononuclear and polymorphonuclear leukocytes. It was found recently (Ahrenstedt, et al., 1990, New Engl. J. Med. 322:1345–9) that the complement C4 concentration in the jejunal fluid of Crohn's disease patients increased compared to normal controls. Other disease states implicating the complement system in inflammation include thermal injury (burns, frostbite) (Gelfand, et al., 1982, J. Clin. Invest. 70:1170; Demling, et al., 1989, Surgery 106:52–9), hemodialysis (Deppisch, et al., 1990, Kidney Inst. 37:696–706; Kojima, et al., 1989, Nippon Jenzo Gakkai Shi 31:91–7), and post pump syndrome in cardiopulmonary bypass (Chenoweth, et al., 1981, Complement Inflamm. 3:152–165; Chenoweth, et al., 1986, Complement 3:152–165; Salama, et al., 1988, N. Engl. J. Med. 318:408–14). Both complement and leukocytes are reported to be implicated in the pathogenesis of adult respiratory distress syndrome (Zilow, et al., 1990, clin Exp. Immunol. 79:151–57; Langlois, et al., 1989, Heart Lung 18:71–84). Activation of the complement system is suggested to be involved in the development of fatal complication in sepsis (Hack, et al., 1989, Am. J. Med. 86:20–26) and causes tissue injury in animal models of autoimmune diseases such as immune complex-induced vasculitis (Cochrane, 1984, Springer Seminar Immunopathol. 7:263), glomerulonephritis (Couser et al, 1985, Kidney Inst. 29:879), hemolytic anemia (Schreiber and Frank, 1972, J. Clin. Invest. 51:575), myasthenia gravis (Lennon, et al., 1978, J. Exp. Med. 147:973; Biesecker and Gomez, 1989, J. Immunol. 142:2654), type II collagen-induced arthritis (Watson and Townes, 1985, J. Exp. Med. 162:1878), and experimental allergic and hyperacute xenograft rejection (Knechtle, et al., 1985, Heart Transplant 4(5):541; Guttman, 1974, Transplantation 17:383; Adachi, et al., 1987, Trans. Proc. 19(1):1145). Complement activation during immunotherapy with recombinant IL-2 appears to cause the severe toxicity and side effects observed from IL-2 treatment (This, et al., 1990, J. Immunol. 144:2419).

Complement may also play a role in diseases involving immune complexes. Immune complexes are found in many pathological states including but not limited to autoimmune diseases such as rheumatoid arthritis or SLE, hematologic malignancies such as AIDS (Taylor, et al., 1983, Arthritis Rheum. 26:736–44; Inada, et al., 1986, AIDS Research 2:235–247) and disorders involving autoantibodies and/or complement activation (Ross, et al., 1985, J. Immunol. 135:2005–14).

Soluble CR1 has been successfully used to inhibit complement activation In a number of animal models: Moat, B. P., et al., 1992, Amer. Review of Respiratory disease 145:A845; Mulligan, M. S., et al., 1992, J. Immunol. 148:1479–1485; Yeh, C. G. et. al., 1991, J. Immunol. 146 250–256; Weisman, et al., 1990, Science 249:146–51; Pruitt, et al., 1991, Transplantation 52(5):868–73; Pruitt and Bollinger, 1991, J. Surg. Res. 50:350–55; Rabinovici, et al., 1992, J. Immunol. 149:1744–50; Mulligan, et al., 1992, J. Immunol. 148:1479–1485; Lindsay, et al., 1992, Annals of Surg. 216:677.

Studies of Weisman et al (1990, Science 249:146–151) have demonstrated that sCR1 can prevent 90% of the generation of C3a and C5a in human serum activated by the yeast cell wall component zymosan. Weisman, et al. (1990, supra) also utilized sCRI in the rat to inhibit complement activation and reduce the damage due to myocardial infarction. Soluble CR1 also appears to inhibit the complement dependent process of the reverse Arthus reaction (Yeh, et al., 1991, J. Immuno. 146:250–256), and hyperacute xenograft rejection (Pruitt, et al., 1991, Transplantation 52:868–873). Recent data (Moat, et al., 1992, Amer. Rev. Respiratory Disease 145:A845) indicate that sCR1 is of value in preventing complement activation in an experimental model of cardiopulmonary bypass in the pig, a situation where complement activation has been demonstrated.

Citation or identification of any reference of Section 2 of this application shall not be constructed as an admission that such reference is available as prior art to the present invention.

3. SUMMARY OF THE INVENTION

According to the present invention, compositions are provided which comprise, in their broadest aspect, a complement moiety and a carbohydrate moiety. These compositions are useful in treating diseases or disorders involving complement, as well as inhibiting a primary event in the inflammatory response such as blocking interactions between intercellular adhesion molecules and their ligands. In preferred aspects, it is an advantage of the present invention that the compositions comprise a ligand for intercellular adhesion molecules. The complement moiety can be any one of a number of proteins which can bind to a complement component, or which are related to a complement receptor type 1 by virtue of containing an SCR motif. The carbohydrate moiety can be any one of a number of carbohydrates that bind to or prevent interaction with an intercellular adhesion molecule. This construct facilitates localization of the complement protein to the site of injury, and advantageously allows for, inter alia, lower dosage treatment. It is a further advantage of the present invention that the same composition can interrupt an initial event in the inflammatory response. Therefore, the complement protein comprising a cellular adhesion molecule ligand is also useful in treating inflammation mediated by intercellular adhesion, as well as complement related diseases or disorders.

The carbohydrate moiety of the compositions of the invention is attached to the complement moiety by means of an extracellular event such as a chemical or enzymatic attachment, or can be the result of an intracellular processing event achieved by the expression of appropriate enzymes. In certain embodiments, the carbohydrate moiety will specifically bind to intercellular adhesion molecules. In one embodiment, the carbohydrate binds to a particular class of adhesion molecules known as the selectins. Thus, in a preferred aspect, the invention provides for a composition comprising at least one complement moiety and at least one carbohydrate moiety, which composition preferentially binds to a particular selectin. Among the selecting are E-selectin, L-selectin or P-selectin. Particularly preferred embodiments comprise at least one complement moiety and at least one carbohydrate moiety wherein said carbohydrate moiety comprises an N-linked carbohydrate, preferably of the complex type, and more preferably fucosylated and sialylated. In the most preferred embodiments, the carbohydrate is related to the Lewis X antigen, and especially the sialylated Lewis X antigen.

In one embodiment, the complement moiety is a protein that contains at least one short consensus repeat and more preferably binds a component of the complement cascade and/or inhibits an activity associated with complement. In a more preferred embodiment, the complement moiety comprises all or a portion of complement receptor type 1. Preferably the complement protein is soluble complement protein. In a most preferred embodiment, the complement moiety is soluble complement receptor type 1 (sCR1), or a fragment or derivative thereof.

The present invention further provides pharmaceutical compositions comprising at least one complement protein and at least one carbohydrate moiety in admixture with a suitable pharmaceutical carrier. In a preferred embodiment, the complement protein is soluble and particularly sCR1 or fragments or derivatives thereof. In these preferred embodiments, the carbohydrate is an N-linked carbohydrate, and preferably fucosylated and more preferably fucosylated and sialylated. Of these the Lewis X ($Le^x$) antigen or sialyl Lewis X ($sLe^x$) antigens are particularly preferred.

The present invention also provides methods for producing the compositions described herein. In one preferred embodiment, the Invention provides for expressing the complement proteins in a cell which glycosylates the complement protein with a $Le^x$ antigen, or preferably a $SLe^x$ antigen, and recovering the protein. In another embodiment, the invention provides for modifying a complement protein by chemically linking the carbohydrate moiety to the protein, wherein said carbohydrate moiety is preferably a selectin ligand.

In yet another embodiment, the invention provides for treating a subject with a disease involving undesirable or inappropriate complement activity. Such treatment comprises administering to a subject in need of treatment, a pharmaceutical composition in accordance with the present invention, in an amount and for a period of time suitable to regulate said undesirable complement activity. Preferably, the carbohydrate moiety in such pharmaceutical compositions are selectin ligands such as $Le^x$, and more preferably the ligand is $SLe^x$. Treatments with the complement protein comprising the selectin ligand include, but are not limited to, diseases or disorders of inappropriate complement activation, especially inflammatory disorders. Such disorders include but are not limited to postischemic reperfusion conditions, infectious disease, sepsis, immune complex disorders and autoimmune disease.

The compositions of the invention can be used in homing the complement moiety, preferably CR1, and more preferably sCR1, to adhesion molecules such as selectins on activated endothelium, allowing for, inter alia, a lower dose as compared to the use of sCR1 alone or its present glycoforms. The compositions can then persist at the site of inflammation, and thereby prevent further activation. Early neutrophil adhesion events which depend on selectin/ligand interaction may also be blocked, Additionally, the in vivo half life of the sCR1 may be prolonged. In a specific embodiment, a CR1 moiety blocks the convertases C3 and C5 in both the classical and alternative pathways, and thus prevents the release of C5a. Preventing the release of C5a further inhibits, inter alia, neutrophil activation and chemoattraction.

It is yet another advantage that the compositions presented herein may have reduced antigenicity. This may be particularly relevant in the context of the preferred embodiments as described herein, as the carbohydrates relating to Lewis X antigen may be more "natural" in their glycosylation patterning as compared to other carbohydrate structures, e.g. those obtained from non-human host cells and the like.

3.1. ABBREVIATIONS

CR1—Complement receptor one.
CR2—Complement receptor two.
CR3—Complement receptor three.
CR4—Complement receptor four.
DAF—Decay-accelerating factor.
ELAM—Endothelial cell adhesion molecule.
$Le^x$—Lewis X antigen.
LHR—Long Homologous Repeat.
MCP—Membrane cofactor protein.
sCR1—Soluble complement receptor one.
$SLe^x$—Sialyl Lewis X antigen.
SCR—Short consensus repeat.
CD15—Lewis X antigen

4. BRIEF DESCRIPTION OF THE FIGURES

FIG. 1A Shows a coomasie-stained SDS-PAGE gel; Lane 1 is molecular weight standards; Lane 2 is control HL-60 cell lysate; Lane 3 contains sCR1[des-A] produced from DUKX.B11 cells; Lane 4 contains sCR1[des-A] recovered from LEC-11 cells.

Figure 2A:
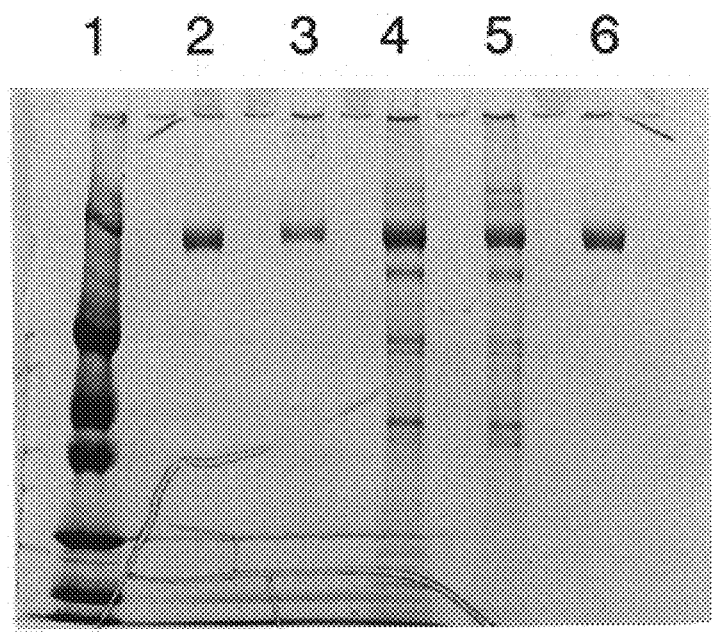

FIG. 2A is a Coomassie Blue stained polyacrylamide gel pattern. The predominant bands at approximately 187 kd in lanes 2, and 4–6 are the sCR1[des-A] protein, lane 2 obtained from DUKX-B11 cells, and lanes 4–6 obtained from LEC-11 cells.

Figure 2B:
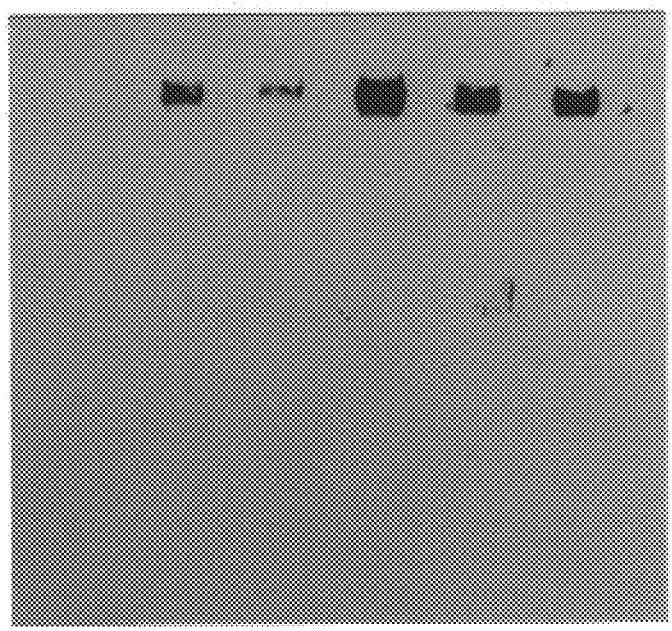

FIG. 2B is the same gel as FIG. 2A, Western blotted and probed with and anti-sCR1[des-A] polyclonal serum. As expected, all lanes containing sCR1-[des-A], whether derived from DUKX-B11cells or LEC-11 cells are poitive for sCR1[des-A].

Figure 2C:
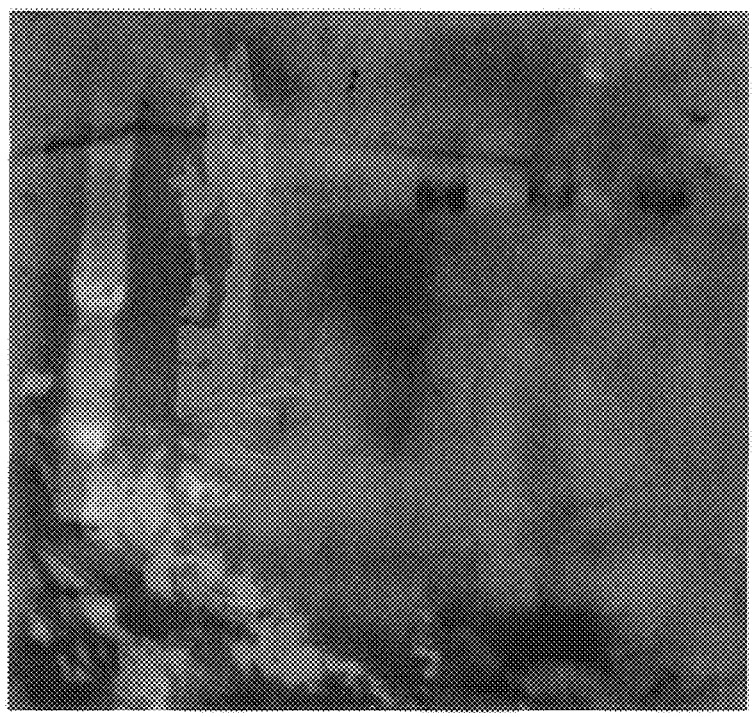

FIG. 2C is the same blot as FIG. 2B stripped and reprobed with an antibody specific for the sialy-diLewis x antigen (FH6) represented by the shorthand notation NeUNAc$\alpha$2-3Gal$\beta$1-4(Fuc$\alpha$1-3)GlcNAc$\beta$1-3Gal$\beta$1-4(Fuc$\alpha$1-3GlcNAc. As expected, only lanes 4–6 containing sCR1[des-A]sLex obtained from LEC-11 cells are positive for the appropriate carbohydrate structure.

Figure 3:
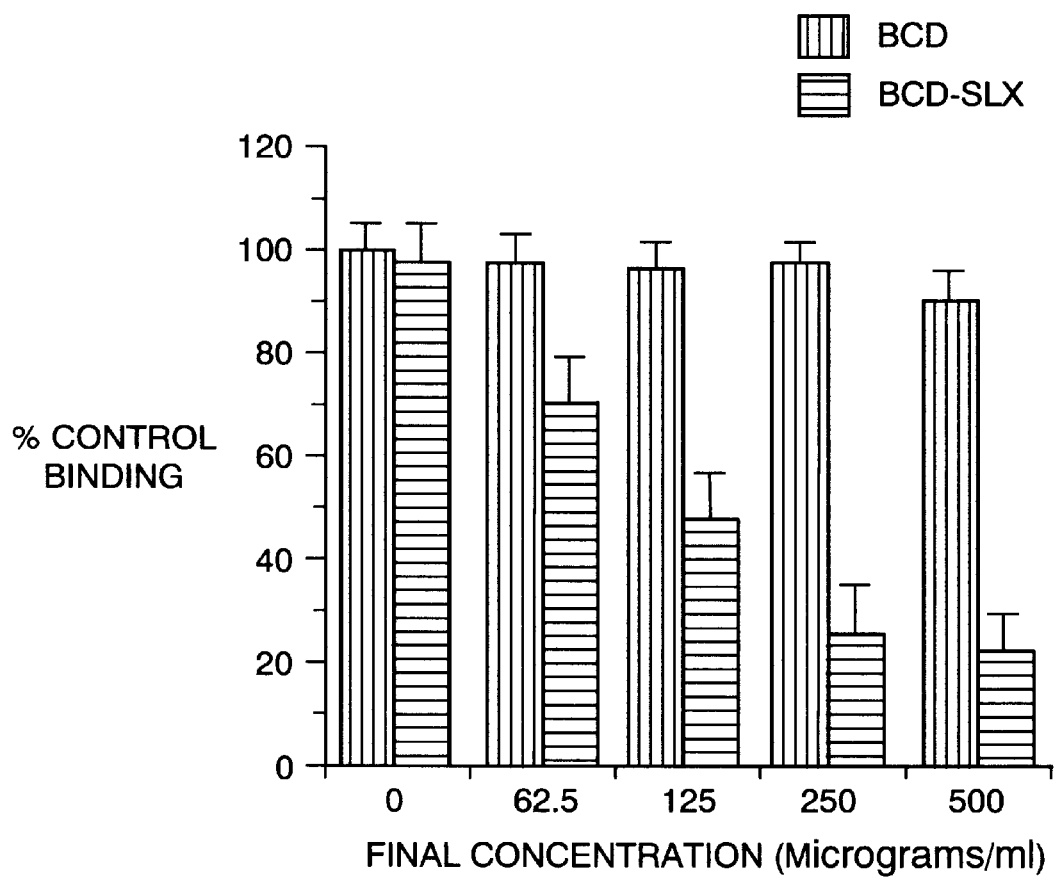

FIG. 3 shows the results of a static adhesion binding assay. The black bars represent the sCR1[des-A] material obtained from DUKX-B11 cells. The bars with horizontal lines represent sCR1[des-A]sLex material obtained form LEC-11 cells. The sCR1[des-A]sLex material inhibited binding of U937 cells to activated aortic endothelial cells in a concentration dependent manner.

Figure 4:
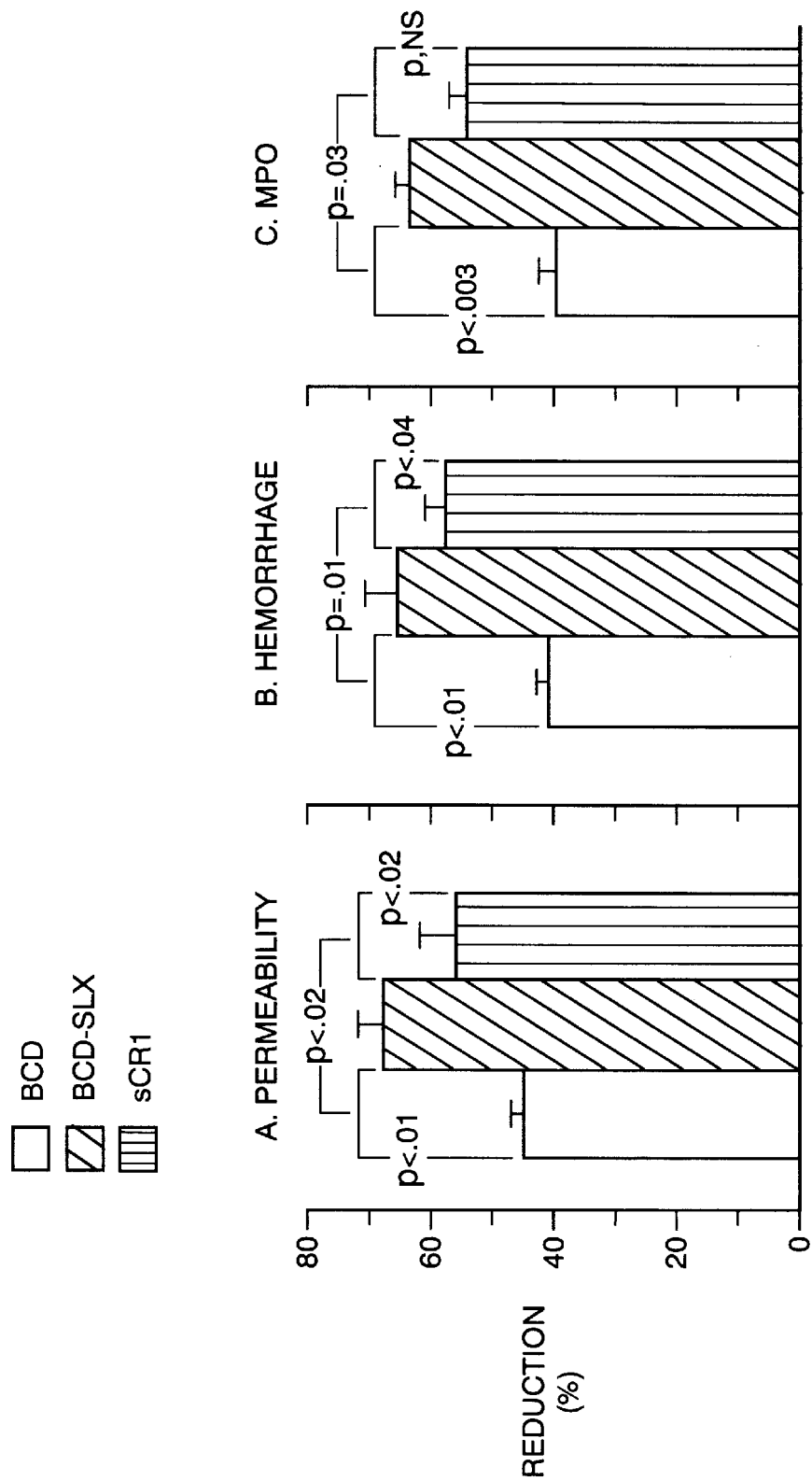

FIG. 4 describes the protective effects of sCR1, sCR1 [des-A], and sCR1[des-A]sLex from lung injury induced by CVF. A. is permeability, a measure of radiolabelled protein leakage from the blood vessels of the lung. B. is the measurement of the reduction over control of hemorrhage as measured by a radiolabelled red blood cell leakage into the lung from the blood vessel. C. is a measure of the accumulation of neutrophils in the lung as estimated by measurement of myeloperoxidase activity.

5. DETAILED DESCRIPTION

The present invention is directed to compositions comprising at least one complement moiety and at least one carbohydrate moiety. The compositions of the invention interact on a cellular level with cells expressing appropriate receptors. In certain preferred embodiments, the carbohydrate moiety of the compositions will bind to a selectin.

For the sake of clarity, the present invention is described in detail in sections relating to the various components of the compositions, methods of producing such compositions as well as pharmaceutical preparations thereof, functional assays for measurement of activity of the compositions, and methods of diagnosis, treatment and prophylaxis using the compositions.

5.1. COMPLEMENT PROTEINS

"Complement moiety" within the scope of this invention means any protein that contains all or a portion of any protein associated with the complement cascade, or a protein that contains at least a portion of a short consensus repeat. Certain useful complement proteins are described in detail in Sections 2.1 and 2.2 of the Background of the Invention, and preferably include but are not limited to complete proteins or any fragment of: complement receptor type 1 (CR1), which is the receptor for complement components C3b and C4b; complement receptor type 2 (CR2), which is the receptor for C3d; complement receptor type 3 (CR3), the receptor for iC3b; complement receptor type 4 (CR4), which is specific to iC3b; complement receptor type 5 (CR5), which is specific for the C3d portion of iC3b, C3dg, and C3d; the C5a receptor (C5a-R); and receptors for C3a and C4a. In a preferred aspect, the invention is meant to include those members of the family of complement regulatory proteins that contain the conserved short consensus repeat (SCR) motif. SCR motifs are found in complement receptor type 1 and in several other C3/C4-binding proteins, most notably CR2, factor H, C4-binding protein (C4-BP), membrane cofactor protein (MCP), and decay accelerating factor (DAF). The genes for factor H, C4-BP, CR2, and DAF map to a region on chromosome 1 which has been designated "regulators of complement activation" (RCA) (Hourcade, D., et al., 1989, Advances in Immunol., 45:381–416). Particular analogues of these regulators of complement activation are found in Atkinson, et al., EPO Publication No. 0 512 733 A2, published on Nov. 11, 1992. Thus, in a preferred embodiment, the complement protein contains at least one SCR and is able to bind to a component of complement. Such complement proteins will, in one embodiment, bind to C3b or C4b or a fragment of C3 or C4, such as those proteins described above.

CR1 has been extensively studied, and a structural motif of 60–70 amino acids, termed the short consensus repeat (SCR) has been discovered. The SCR motif is tandemly repeated 30 times in the F-allotype of CR1, and additional repeat cycles occur in other allotypes. The consensus sequence of the SCR includes 4 cysteines, a glycine and a tryptophan that are invariant among all SCRs. Sixteen other positions are conserved, with the same amino acid or a conservative replacement being found in over half of the other 30 SCRs (Klickstein, et al., 1987, J. Exp. Med. 165:1095–1112; Klickstein et al, 1988, J. Exp. Med., 168:1699–1717; Hourcade et al., 1988, J. Exp. Med. 168:1255–1270). The dimensions of each SCR are estimated to be approximately 2.5–3.0 nm×2 nm×2 nm.

Tandem repeats of SCRs (the same invariant residues and similar spacing between cysteines) have been identified in 12 additional proteins of the complement systems (Ahearn et al., 1989, Adv. Immunol. 46:183–219). These proteins share a capacity for interacting with C3, C4, or C5, the set of homologous complement proteins that are subunits of the alternative and classical C3–C4 convertases and the membrane attack complex, respectively. Complement-related proteins containing SCRs may have activating functions (Clr, Cls, Factor B and C2), negative regulatory roles (Factor H, C4-BP, DAF, MCP, and CR1), serve as cellular receptors capable of eliciting functions of phagocytes and lymphocytes (CR1 and CR2) or promote the formation of the complement channel-forming membrane attack complex (C6 and C7). Thus, the SCR is one of the most characteristic structures of the complement system. The finding of SCR's in non-complement proteins, such as in an interleukin-2 receptor $\alpha$ chain, $\beta$2-glycoprotein 1, and factor XIII does not necessarily indicate a complement-related function, although this possibility has not been excluded.

It is within the scope of the invention that the compositions comprise one or more of the aforementioned SCRs, in any combination suitable to obtain a desired result. As additional criteria, those forms of the complement protein or fragments thereof that are readily absorbed by tissues, that are protected from rapid metabolism and/or that provide for prolonged half life, are preferentially selected in producing the compositions of the invention. One skilled in the art may also effect modifications of the protein formulation, to effect absorption. These modifications include, but are not limited to, use of a prodrug and chemical modification of the primary structure (Wearley, L. L., 1991, Crit. Rev. in Ther. Drug Carrier Systems, 8(4):333). In minimizing metabolism of the complement protein and thereby increasing the effective amount of protein, such modifications include but are not limited to chemical modifications and covalent attachment to a polymer (Wearley, L. L., 1991, supra).

The compositions of the present invention may be part of a delivery system such as liposomes. Delivery systems involving liposomes are discussed in International Patent Publication No. WO 91/02805 and International Patent Publication No. WO 91/19501, as well as U.S. Pat. No. 4,880,635 to Janoff et al. These publications and patents provide useful descriptions of techniques for liposome drug delivery.

The genes for the complement related proteins are readily available, for instance the nucleic acid sequences and/or genes encoding the complement proteins of the present invention are known as, for instance; DAF, International Patent Publication No. WO89/01041 published Feb. 9, 1989; MCP, Lublin M. D., et al., 1988, J. Exp. Med. 168:181–194; and, CR2, Weis, J. J., et al., 1988, J. Exp. Med. 168:1047–1066. The CR1 gene and its encoded protein are provided for in International Patent Publication No. WO89/09220 published Oct. 5, 1989 and entitled "The Human C3b/C4b Receptor (CR1)". Once the gene and its encoded protein are available, any number of techniques known in the art can be used to modify the gene itself or its encoded proteins. The invention is meant to include such complement protein-related fragments, derivatives, and analogues. The complement protein-related fragments, derivatives, and analogues for use in the composition and formulations of the invention can be produced by various methods known in the art. The manipulations which result in their production can occur at the gene or protein level, or by methods of chemical synthesis. For example, a cloned complement gene can be modified by any of numerous strategies known in the art (Maniatis, T., 1982, Molecular Cloning, A Laboratory Manual, Cold Spring Harbor Laboratory, Cold Spring Harbor, N.Y.). The complement protein gene sequence can be cleaved at appropriate sites with restriction endonuclease(s) followed by further enzymatic modification if desired, isolated, and ligated In vitro. In the production of the gene encoding a derivative, analogue, or peptide related to a complement protein, care should be taken to ensure that the modified gene remains within the same translational reading frame as the native complement protein gene, uninterrupted by translational stop signals, in the gene region where the desired complement inhibitory-specific activity is encoded.

Additionally, the complement protein gene can be mutated In vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551), use of TABX linkers (Pharmacia), and the like methods.

Manipulations of the complement protein sequence may also be made at the protein level. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, and the like.

In a particular embodiment in which the complement protein is CR1, for example, specific modifications of the nucleotide sequence of CR1 can be made by recombinant DNA procedures that result in sequences encoding a protein having multiple LHR-B sequences. See, e.g., International Patent Publication No. WO91/05047, published Apr. 18, 1991. Such valency modifications alter the extent of C3b binding which may be important for disorders associated with such functions, such as immune or inflammatory disorders. For example, full-length CR1 or fragments thereof and related molecules which exhibit the desired activity can have therapeutic uses in the inhibition of complement by their ability to act as a factor I cofactor, promoting the irreversible inactivation of complement components C3b or C4b (Fearon, D. T., 1979, Proc. Natl. Acad. Sci. U.S.A. 76:5867; Iida, K. and Nussenzweig, v., 1981, J Exp. Med. 153:1138), and/or by the ability to inhibit the alternative or classical C3 or C5 convertases.

In another embodiment, specific portions of the sequences of CR1 that contain specific, well defined combinations of LHRs or SCRs can also be generated. The activities of these compounds can be predicted by choosing those portions of the full-length CR1 molecules that contain a specific activity. The resulting fragments should, but need not contain, at least one of the functions of the parent molecule. Such functions include but are not limited to the binding of C3b and/or C4b, in free or in complex forms; the promotion of phagocytosis, complement regulation, immune stimulation; the ability to act as a factor I cofactor; promoting the irreversible inactivation of complement components C3b or C4b, (Fearon, D. T., 1979, Proc. Natl. Acad. Sci. U.S.A. 76:5867; Iida, K. and Nussenweig, V., 1981, J. Exp. Med. 153:1138); effecting immune complex clearance and/or by the ability to inhibit the alternative or classical C3 or C5 convertases. In a specific embodiment, the CR1 includes LHR's B, C and D and does not include LHR A.

In addition, analogues and peptides related to complement proteins can be chemically synthesized. For example, a peptide corresponding to a portion of complement protein which mediates the desired activity (e.g., C3b and/or C4b binding, immune stimulation, complement regulation, etc.) can be synthesized by use of a peptide synthesizer.

In particular embodiments of the present invention, such complement proteins, including derivatives, analogues or fragments thereof, whether produced by recombinant DNA techniques or by chemical synthetic methods, include but are not limited to those containing, as a primary amino acid sequence, all or part of the amino acid sequence of the native complement protein including altered sequences in which functionally equivalent amino acid residues are substituted for residues within the sequence, resulting in a silent change. For example, one or more amino acid residues within the sequence can be substituted by another amino acid of a similar polarity which acts as a functional equivalent, resulting in a silent alteration. Nonconservative substitutions can also result in functionally equivalent proteins.

In one embodiment, substitutes for an amino acid within the complement protein sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a particular embodiment, nucleic acid sequences encoding a fusion protein, consisting of a molecule comprising a portion of a complement protein sequence plus a non-complement protein sequence, can be produced. See, e.g., International Patent Publication No. WO91/05047. For example, further modifications of complement proteins containing LHRs or SCRs include the generation of chimeric molecules containing portions of the LHR and/or SCR sequences attached to other molecules whose purpose is to affect solubility, pharmacology or clearance of the resultant chimeras. Such chimeras can be produced either at the gene level as fusion proteins or at the protein level as chemically produced derivatives. Chimeric molecules comprising portions of immunoglobulin chains and complement protein can contain Fab or (Fab')$_2$ molecules, produced by proteolytic cleavage or by the introduction of a stop codon after the hinge region in the heavy chain to delete the $F_c$ region of a non-complement activating isotype in the immunoglobulin portion of the chimeric protein to provide $F_c$ receptor-mediated clearance of the complement activating complexes. Other molecules that may be used to form chimeras include, but are not limited to, other SCR containing proteins, proteins such as serum albumin, heparin, or immunoglobulin, polymers such as polyethylene glycol or polyoxyethylated polyols, or proteins modified to reduce antigenicity by, for example, derivatizing with polyethylene glycol. Suitable molecules are known in the art and are described, for example, in U.S. Pat. Nos. 4,745,180, 4,766, 106 and 4,847,325 and references cited therein. Additional molecules that may be used to form derivatives of the biological compounds or fragments thereof include protein A or protein G (International Patent Publication No. WO87/ 05631 published Sep. 24, 1987 and entitled "Method and means for producing a protein having the same IgG specificity as protein G"; Bjorck, et al., 1987, Mol. Immunol. 24:1113–1122; Guss, et al., 1986, EMBO J. 5:1567–1575; Nygren, et al., 1988, J. Molecular Recognition 1:69–74). Constructs comprising a plurality of short consensus repeats having a complement binding site, said constructs attached to an immunoglobulin chain or a soluble, physiologically compatible macromolecular carrier, are also suitable as the complement moiety taught herein. Preparation of these constructs is disclosed in International Patent Publication No. WO91/16437, herein incorporated by reference.

Isolation and recovery of encoded proteins may be effected by techniques known in the art. The complement proteins may be isolated and purified by standard methods including chromatography (e.g., ion exchange, affinity, and sizing column chromatography, high performance liquid chromatography), centrifugation, differential solubility, or by any other standard technique for the purification of proteins. If the complement protein is exported by a cell that is producing it, a particularly efficacious method for purification of the protein is as follows: the cell culture medium containing protein is subject to the sequential steps of a) cationic exchange chromatography, b) ammonium sulfate precipitation, c) hydrophobic interaction chromatography, d) anionic exchange chromatography, e) further cationic exchange chromatography and f) size exclusion chromatography.

In a more preferred embodiment, the instant invention relates to soluble CR1 molecules. As used herein, the term soluble CR1 molecules means portions of the CR1 protein, which, upon expression, are not located in the cell surface as membrane proteins. As a particular example, CR1 molecules which substantially lack the transmembrane region are soluble CR1 molecules. In a specific emmbodiment of the invention, an expression vector can be constructed to encode a CR1 molecule which lacks the transmembrane region (e.g., by deletion of the carboxyl-terminal to the Aspartate encoded by the most C-terminal SCR), resulting in the production of a soluble CR1 fragment. In one embodiment, such a fragment can retain the ability to bind C3b and/or C4b, in free or in complex forms. In a particular embodiment, such a soluble CR1 protein may no longer exhibit factor I cofactor activity.

Soluble constructs carrying some or all of the binding sites of CR1 are also envisioned. Such constructs will in certain preferred embodiments, inhibit activation of complement and the complement dependent activation of cells. For example, in a specific embodiment, a soluble CR1 molecule can be used which retains a desired functional activity, as demonstrated, e.g., by the ability to inhibit classical complement-mediated hemolysis, classical C5a production, classical C3a production, or neutrophil oxidative burst in vitro. In one embodiment, such a fragment can retain the ability to bind C3b and/or C4b, in free or in complex form. The sCR1 molecule so produced can contain the LHR-A, LHR-B, LHR-C, LHR-D, SCR29, SCR30, up to and including the first alanine residue of the transmembrane region. In a preferred aspect of the invention, the soluble CR1 protein has the characteristics of the protein expressed by a Chinese hamster ovary cell DUX B11 carrying plasmid pBSCR1/ pTCSgpt as deposited with the ATCC and assigned accession number CRL 10052.

In a further specific embodiment, a CR1 molecule can be produced that lacks the LHR-A region of the CR1 molecule. To this end, an expression vector can be constructed to encode a CR1 molecule which lacks the transmembrane region and SCRs 1–7, resulting in the production of a soluble CR1 fragment that would be expected to preferentially inhibit the alternative pathway. The expression vector so constructed would be expected to contain sites for primarily C3b binding. Therefore, such a construct would be expected to preferentially inhibit the alternative complement pathway as assessed by the in vitro hemolytic assays described herein.

In yet another embodiment, an expression vector can be constructed to contain only SCR's 1–18 of the complement receptor type 1. Such a construct would be expected to have the full function associated with complement receptor type 1 by virtue of containing sites for binding C3b and C4b. Such a product would be expected to inhibit the classical and alternative pathways of complement as assessed by the in vitro assays described herein. In yet another embodiment the construct may contain only SCR's 15–18. Such a construct would be expected to bind C3b primarily, and preferentially inhibit the alternative pathway of complement.

These constructs, as well as the other constructs of the application can have advantages due to differences in glycosylation. Such differences are expected to affect such parameters as the in vivo half-life of the molecule. One skilled in the art will recognize the potential sites for N-linked glycosylation will vary with the products of such constructs. Differences in glycosylation can be assessed by the functional assays described herein for their ability to block the binding of the natural ligand for the particular cellular adhesion molecule.

The complement proteins of the invention can be assayed by techniques known in the art in order to demonstrate their complement-related activity. Such assays include but are not limited to the following In vitro tests for the ability to interact with complement proteins, to inhibit complement activity, or to selectively inhibit the generation of complement-derived peptides:

(i) measurement of inhibition of complement-mediated lysis of cells, for instance, red blood cells (IH50 assay)(International Patent Publication No. WO92/10096)

(ii) measurement of ability to inhibit formation of complement activation products such as, C5a and C5a des Arg and/or measurement of ability to inhibit formation of C3a or C3a des Arg, or measurement of ability to inhibit formation of C5b-9, or sC5b-9 (International Patent Publication No. WO92/10096)

(iii) measurement of ability to serve as a cofactor for factor I degradation of, for instance, C3b or C4b (Makrides et al., (1992) 267:24754–24761, Weisman, H. F., et al. (1990) Science, 244:146–151).

(iv) measurement of ability to bind to C3b or other C3 derived proteins, or binding of C4b or other C4b derived proteins (Makrides et al, supra, Weisman et al, supra)

(v) measurement of inhibition of alternative pathway mediated hemolysis (AH50 assay)(International Patent Publication No. WO92/10096)

Any complement protein or fragment, derivative or analog thereof, in particular a CR1 protein, that has any one of the activities associated with complement receptors is within the scope of this invention as the complement moiety of the compositions provided herein.

Activities normally associated with complement receptor type 1 are well documented in the art. For example, for soluble CR1 proteins, such activities include the abilities in vitro to inhibit neutrophil oxidative burst, to inhibit complement-mediated hemolysis, to inhibit C3a and/or C5a production, to bind C3b and/or C4b, to exhibit factor I cofactor activity, and to inhibit C3 and/or C5 convertase activity. A representative disclosure of activities and assays are described inter alia in International Patent Publication No. PCT/US89/01358, published Oct. 5, 1989 as WO89/09220, supra; and entitled Weissman, et al., 1990, Science 249:146–151; Fearon, D. T. and Wong, W. W., 1989, Ann. Rev. Immunol. 1:243; Fearon, D. T., 1979, Proc. Natl. Acad. Sci. U.S.A. 76:5867; Iida, K. and Nussenzweig, V., 1981, J. Exp. Med. 153:1138; Klickstein et al., 1987, J. Exp. Med., 165:1095; Weiss, et al., 1988, J. Exp. Med., 167:1047–1066; Moore, et al., 1987, Proc. Natl. Acad. Sci. 84:9194; Moore, et al, 1989, J. Biol. Chem. 264:205–76).

5.2. CARBOHYDRATE STRUCTURES COMPRISING SELECTIN LIGANDS

The carbohydrate moiety of the compositions of the present invention may be selected from a variety of carbohydrate structures. In preferred embodiments, this moiety is responsible for binding the complement moiety to particular cell adhesion molecules, such as a selectin. Section 2.3 of the Background of the Invention details several selectins that the carbohydrate moiety suitably binds to. Carbohydrate moieties that bind to intercellular adhesion molecules, including selecting, are well known in the art. For instance, International Patent Publication No. WO91/19502 published Dec. 26, 1991 and entitled "Intercellular Adhesion Mediators"; International Patent Publication No. WO92/02527 published Feb. 20, 1992 and entitled "New Carbohydrate-Based Anti-Inflammatory Agents"; International Patent Publication No. WO92/19735 published Nov. 12, 1992 and entitled "GLYCAM-1(Spg 50), A Selectin Ligand"; International Patent Publication No. WO92/01718 published Feb. 6, 1992 and entitled "Functionally Active Selectin-derived Peptides and Ligands for GMP-140"; International Patent Publication No. WO91/19501 published Dec. 26, 1991 and entitled "Intercellular Adhesion Mediators" all present disclosure of carbohydrate molecules useful in the present invention: the published patent applications are herein incorporated by reference. The synthesis and processing of carbohydrates is also well known in the art (Hubbard, S. C. and Ivatt, R. J. (1981) Ann. Rev. Biochem. 50:555–83 and the references cited therein; Goochee, C. F., (1991) Biotechnology, 9:1347–1355, and the references cited therein; Kobata, A. (1992) Eur. J. Biochem. 209, 483–501, and the references cited therein). Accordingly, the carbohydrate moiety of the instant invention can efficiently interact with cell adhesion molecules.

Particular ligands for selectins have also been described (Howard, D. R., et al., (1987) J. Biol. Chem. 262:16830–16837, Phillips, M. L., et al., (1990) Science 250:1130–1132, Walz, G. et al., (1990) Science, 250:1132–1135, Stanley, P., and Atkinson, P., (1986) J. Biol. Chem. 263:11374–11381; Butcher, E., (1991) Cell, 67:1033–1036). The Lewis X and sialyl Lewis X oligosaccharides have been shown to be particularly important in selectin binding. Recent studies have further characterized the ligand structures for selectins and note that modifications of the Lewis X and sialyl Lewis X oligosaccharide may enhance the interactions between the oligosaccharides and the selectins (Bevilacqua, M. P. and Nelson, R. M. (1993) J. Clin. Invest. 91:379–387, Nelson, R. M., et al., (1993) J. Clin. Invest. 91:1157–1166, Norgard, K. E. et al., (1993) Proc. Natl. Acad. Sci., U.S.A. 90:1068–1072; Imai, Y. et al., (1993) Nature 361:555–557).

The carbohydrate moiety of the present invention will now be described with reference to commonly used nomenclature for the description of oligosaccharides. A review of carbohydrate chemistry which uses this nomenclature is found in, Hubbard and Ivatt (1981) supra. This nomenclature includes, for instance, Man, which represents mannose; GlcNAc, which represents 2-N-acetyl glucosamine; Fuc, which represents fucose; Gal, which represents galactose; and Glc, which refers to glucose. In preferred embodiments, the carbohydrate moiety comprises sialic acid residues. Two preferred sialic acid residues are described in shorthand notation by "NeuNAc", for 5-N-acetylneuraminic acid, and "NeuNGc" for 5-glycolyl neuraminic acid. (J. Biol. Chem., 1982, 257:3347; J. Biol. Chem., 1982, 257:3352).

This method of describing carbohydrates, as will be readily understood by one skilled in the art, includes notations for the various glycosidic bonds relevant to naming carbohydrates. Therefore, in describing a bond linking two or more monosaccharides to form an oligosaccharide, a β glycosidic bond between the C-1 of galactose and the C-4 of glucose is commonly represented by Galβ1-4Glc. The notation β and α are meant to represent the orientation of the bond with respect to the glycosidic ring structure. For the D-sugars, for instance, the designation β means the hydroxyl attached to the C-1 is above the plane of the ring. Conversely, for the D-sugars, the designation a means the hydroxyl group attached to the C-1 is below the plane of the ring. The carbohydrate moiety will be described with reference to this shorthand notation.

In its broadest aspects, carbonydrate structures useful in the present invention may be selected from a wide range of structures. Preferably, the carbohydrate will interact at some level with an adhesion molecule. For example, such moiety will bind to, or prevent the binding of a natural ligand to a cellular adhesion molecule, or even displace an endogenously occurring ligand. As is well understood in the art, interaction between a particular ligand and its receptor is generally described by affinity constants. "Binding affinity" is generally measured by affinity constants for the equilibrium concentrations of associated and dissociated configurations of the ligand and its receptor. The present invention contemplates such an interaction between a carbohydrate ligand and its endothelial cell adhesion molecule receptor. In general, the binding of the carbohydrate moiety should occur at an affinity of about $k_a=10^4 M^{-1}$ or greater to be useful for the present invention, with greater than about $10^8 M^{-1}$ being more preferable, and most preferably between about $10^8 M^{-1}$ and about $10^4 M^{-1}$.

In a particular embodiment, the carbohydrate structure of the present invention is a ligand for the class of cell adhesion molecules known as selecting. Selectins have been shown to bind to a variety of carbohydrate structures which can broadly be classified into three groups. The first group includes the N-linked and O-linked carbohydrates. N-linked and O-linked carbohydrates differ primarily in their core structures. The N-linked carbohydrates all contain a common Manα1-6(Manα1-3)Manβ1-4GlcNAcβ1-4GlcNAcβ-R core structure. Of the N-linked carbohydrates, the most important for the present invention are the complex N-linked carbohydrates. Such complex N-linked carbohydrates will contain several antennary structures. Thus, the mono-, bi-, tri-, tetra-, and penta-antennary outer chains are important. Such outer-chain structures provide for additional sites for the specific sugars and linkages that comprise the carbohydrates of the present invention. N-linked glycosylation refers to the attachment of the carbohydrate moiety via GlcNAc to an asparagine residue in the peptide chain. Therefore, in the core structure described, R represents an asparagine residue. The peptide sequences of the complement moiety, asparagine-X-serine, asparagine-X-threonine, and asparagine-X-cysteine, wherein X is any amino acid except proline are possible recognition sites for enzymatic attachment of the N-linked carbohydrate moiety of the invention. O-linked carbohydrates, by contrast, are characterized by a common core structure, which is the GalNAc attached to the hydroxyl group of a threonine or serine.

The N-linked glycans are formed by a series of complex steps occurring intracellularly by a series of enzymes with the addition of appropriate sugars. Alternatively, the enzymatic synthesis of the core structures can be accomplished extracellularly by chemical and enzymatic steps to produce the appropriate carbohydrates. These chemical and enzymatic syntheses have been described in the art, for instance in International Patent Publication No. WO91/19502 and the references described therein, which is incorporated herein by reference.

Specific glycosyltransferases are important for the final outer chain structures of the complex carbohydrates. These glycosyltransferases are highly specific for the appropriate monosaccharides. Of particular importance to the invention are the enzymes involved in sialylation and fucosylation of the Galβ1-4GlcNAc group found in the N-linked and O-linked oligosaccharides. It will be understood by one skilled in the art that terminal glycosylation sequences differ. Among the various structures found in the outer chain moieties of the complex oligosaccharide chains are the carbohydrates moieties that are known to bind to particular selectins.

Particularly preferred within the context of the present invention are the sialylated, fucosylated N-acetylglucosamines which have both a sialic acid and a fucose residue in specific position and linkage. Therefore, the oligosaccharides related to the Lewis X (Le$^x$) carbohydrate (Galβ1-4(Fucα1-3)GlcNAc) are especially useful. Structures of the general formula I are particularity relevant:

Especially significant among this group are the sialylated Lewis X carbohydrate determinant (sLe$^x$) Neu5Acα2-3Galβ1-4(Fucα1-3)GlcNAc and closely related structures, including as well, sLe$^a$, a structural isomer of sLe$^x$, Neu5Acα2,3Galβ1,3(Fucα1,4)GlcNAc. Therefore, in a particularly preferred embodiment the carbohydrate structure is represented by the general formula II:

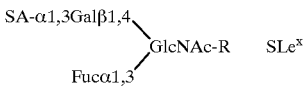

where R represents the remaining carbohydrate structure and SA represents a sialic acid. In a preferred embodiment, the sialic acid is 5-N-acetylneuraminic acid. In another embodiment, the sialic acid is 5-glycolyl neuraminic acid.

Additional examples of specific carbohydrate structures useful in the compositions of the invention are disclosed in International Patent Publication No. WO92/02527 and can be expressed as follows:

NeuNAcα2-3Galβ1-4(Fucα1-3)GlcNAc

NeuNAcα2-6 Galβ1-4(Fucα1-3)GlcNAc

NeuNAcα2-3Galβ1-4GlcNAcβ1-3Galβ1-4(Fucα1-3) GlcNAc

NeuNAcα2-6 Galβ1-4GlcNAcβ1-3Galβ1-4(Fucα1-3) GlcNAc

NeuNAcα2-3Galβ1-4(Fucα1-3)GlcNAcβ1-3Galβ1-4 (Fucα1-3)GlcNAc

NeuNAcα2-6 Galβ1-4(Fucα1-3)GlcNAcβ1-3Galβ1-4 (Fucα1-3)GlcNAc

NeuNAcα2-3Galβ1-4(Fucα1-3)GlcNAcβ1-3Galβ1-4Glc

NeuNAcα2-6 Galβ1-4(Fucα1-3)GlcNAcβ1-3Galβ1-4Glc

NeuNAcα2-3Galβ1-4GlcNAcβ1-3Galβ1-4(Fucα1-3) GlcNAcβ1-3Galβ1-4Glc

NeuNAcα2-6Galβ1-4GlcNAcβ1-3Galβ1-4(Fucα1-3) GlcNAcβ1-3Galβ1-4Glc

NeuNAcα2-3Galβ1-4(Fucα1-3)GlcNAcβ1-3Galβ1-4 (Fucα1-3)GlcNAcβ1-3Galβ1-4Glc

NeuNAcα2-6Galβ1-4(Fucα1-3)GlcNAcβ1-3Galβ1-4 (Fucα1-3)GlcNAcβ1-3Galβ1-4Glc

NeuNAcα2-3Galβ1-4(Fucα1-3)GlcNAcβ1-3galβ1-4 (Fucα1-3)Glc

NeuNAcα2-3Galβ1-4(Fucα1-3)GlcNAcβ1-3galβ1-4 (Fucα1-3)Glc

NeuNAcα2-3Galβ1-4GlcNAcβ1-3Galβ1-4(Fucα1-3) GlcNAcβ1-3Galβ1-4(Fucα1-3)Glc

NeuNAcα2-6Galβ1-4GlcNAcβ1-3Galβ1-4(Fucα1-3) GlcNAcβ1-3Galβ1-4(Fucα1-3)Glc

NeuNAcα2-3Galβ1-4(Fucα1-3)GlcNAcβ1-3Galβ1-4 (Fucα1-3)GlcNAcβ1-3Galβ1-4(Fucα1-3)Glc

NeuNAcα2-6Galβ1-4(Fucα1-3)GlcNAcβ1-3Galβ1-4
(Fucα1-3)GlcNAcβ1-3Galβ1-4(Fucα1-3)Glc
NeuNAcα2-3Galβ1-3(Fucα1-4)GlcNAc
NeuNAcα2-6Galβ1-3(Fucα1-4)GlcNAc
NeuNAcα2-3Galβ1-3GlcNAcβ1-4Galβ1-4(Fucα1-3)
GlcNAc
NeuNAcα2-6Galβ1-3GlcNAcβ1-4Galβ1-4(Fucα1-3)
GlcNAc
NeuNAcα2-3Galβ1-3(Fucα1-4)GlcNAcβ1-3Galβ1-4
(Fucα1-3)GlcNAc
NeuNAcα2-6Galβ1-3(Fucα1-4)GlcNAcβ1-3Galβ1-4
(Fucα1-3)GlcNAc
NeuNAcα2-3Galβ1-3(Fucα1-4)GlcNAcβ1-3Galβ1-4Glc
NeuNAcα2-6Galβ1-3(Fucα1-4)GlcNAcβ1-3Galβ1-4Glc
NeuNAcα2-3Galβ1-3GlcNAcβ1-4Galβ1-4(Fucα1-3)
GlcNAcβ1-3Galβ1-4Glc
NeuNAcα2-6Galβ1-3GlcNAcβ1-4Galβ1-4(Fucα1-3)
GlcNAcβ1-3Galβ1-4Glc
NeuNAcα2-3Galβ1-3(Fucα1-4)GlcNAcβ1-3Galβ1-4
(Fucα1-3)GlcNAcβ1-3Galβ1-4Glc
NeuNAcα2-6Galβ1-3(Fucα1-4)GlcNAcβ1-3Galβ1-4
(Fucα1-3)GlcNAcβ1-3Galβ1-4Glc
NeuNAcα2-3Galβ1-3(Fucα1-4)GlcNAcβ1-3Galβ1-4
(Fucα1-3)Glc
NeuNAcα2-6Galβ1-3(Fucα1-4)GlcNAcβ1-3Galβ1-4
(Fucα1-3)Glc
NeuNAcα2-3Galβ1-3GlcNAcβ1-4Galβ1-4(Fucα1-3)
GlcNAcβ1-3Galβ1-4(Fucα1-3)Glc
NeuNAcα2-6Galβ1-3GlcNAcβ1-4Galβ1-4(Fucα1-3)
GlcNAcβ1-3Galβ1-4(Fucα1-3)Glc
NeuNAcα2-3Galβ1-3(Fucα1-4)GlcNAcβ1-3Galβ1-4
(Fucα1-3)GlcNAcβ1-3Galβ1-4(Fucα1-3)Glc
NeuNAcα2-6Galβ1-3(Fucα1-4)GlcNAcβ1-3Galβ1-4
(Fucα1-3)GlcNAcβ1-3Galβ1-4(Fucα1-3)Glc
NeuNAcα2-3Galβ1-4GlcNAcβ1-3Galβ1-3(Fucα1-4)
GlcNAc
NeuNAcα2-6Galβ1-4GlcNAcβ1-3Galβ1-3(Fucα1-4)
GlcNAc
NeuNAcα2-3Galβ1-4(Fucα1-3)GlcNAcβ1-3Galβ1-3
(Fucα1-4)GlcNAc
NeuNAcα2-6Galβ1-4(Fucα1-3)GlcNAcβ1-3Galβ1-3
(Fucα1-4)GlcNAc
NeuNAcα2-3Galβ1-4GlcNAcβ1-3Galβ1-3(Fucα1-4)
GlcNAcβ1-3Galβ1-4Glc
NeuNAcα2-6Galβ1-4GlcNAcβ1-3Galβ1-3(Fucα1-4)
GlcNAcβ1-3Galβ1-4Glc
NeuNAcα2-3Galβ1-4(Fucα1-3)GlcNAcβ1-3Galβ1-3
(Fucα1-4)GlcNAcβ1-3Galβ1-4Glc
NeuNAcα2-6Galβ1-4(Fucα1-3)GlcNAcβ1-3Galβ1-3
(Fucα1-4)GlcNAcβ1-3Galβ1-4Glc
NeuNAcα2-3Galβ1-4(Fucα1-3)GlcNAcβ1-3Galβ1-3
(Fucα1-4)Glc
NeuNAcα2-6Galβ1-4(Fucα1-3)GlcNAcβ1-3Galβ1-3
(Fucα1-4)Glc
NeuNAcα2-3Galβ1-4GlcNAcβ1-3Galβ1-3(Fucα1-4)
GlcNAcβ1-3Galβ1-4(Fucα1-3)Glc
NeuNAcα2-6Galβ1-4GlcNAcβ1-3Galβ1-3(Fucα1-4)
GlcNAcβ1-3Galβ1-4(Fucα1-3)Glc
NeuNAcα2-3Galβ1-4(Fucα1-3)GlcNAcβ1-3Galβ1-3
(Fucα1-4)GlcNAcβ1-3Galβ1-4(Fucα1-3)Glc
NeuNAcα2-6Galβ1-4(Fucα1-3)GlcNAcβ1-3Galβ1-3
(Fucα1-4)GlcNAcβ1-3Galβ1-4(Fucα1-3)Glc

Methods of chemically and enzymatically synthesizing the carbohydrate structure are well known in the art and can be found in International Patent Publication No. WO91/19502 which is incorporated herein by reference. Additionally, these structures may be obtained by the methods described infra.

As will be described in detail in subsequent sections, these structures may be provided on the complement moiety by a variety of mechanisms including but not limited to the transfection of the particular complement expressing cell with appropriate fucosyltransferase enzymes. Alternatively, the structures may be chemically synthesized using appropriate fucosyltransferases and sialyltransferases and chemically linked to the complement moiety. Such transferases are generally available as described below.

As noted earlier, specific modifications of the selectin ligand may enhance the interaction between the carbohydrate determinant and particular selecting. Nelson et al. studied the binding interaction of a series of oligosaccharides based on the $SLe^x$ and $SLe^a$ ($sLe^a$ may be especially significant in tumor metastasis due to its significant expression on certain cancer cells) structures (Nelson, et al., (1993) J. Clin. Invest. 91:1157–1166). Nelson suggests that both the sialic acid and the fucose in specific position and linkage enhance E-selectin recognition (Nelson, supra). Both the $SLe^a$ and $SLe^a$ contain a terminal sialic acid (Neu5Ac) linked in an α2-3 linkage to the galactose (Gal), which is in turn linked to N-acetylglucosamine (GlcNAc). Both structures also contain a fucose coupled to the sub terminal GlcNAc. This characteristic structure is generally a part of larger glycoproteins. Accordingly, in certain preferred embodiments, the carbohydrate is modified to contain at least one sialic acid in conformation with at least one fucose residue.

E-selectin may also bind to oligosaccharides related to $SLe^x$ and $SLe^a$ which lack the terminal sialic acid but instead have a sulfate group (Yuen, C. T. et al., (1992) Biochemistry 31:9126–9131). Modification of this primary structure may have selective advantage of homing the carbohydrate moiety to a particular selectin. Therefore, within the scope of the present invention are the carbohydrates which lack the terminal sialic acid but instead have a sulfate group. Additionally, sulphation of glycoproteins may enhance ligand binding to L-selectins (Imai, Y, Lasky, L. A., and Rosen, S. D. (1993) Science 361:555–557). In this regard, Yuen at al., (1992) Biochemistry 31:9126–91341 is instructive and is hereby incorporated by reference.

Selective oxidization of the sialic acid residues, without affecting the underlying oligosaccharide, enhances the interaction with L-selectins as described by Norgard et al., (1993) Proc. Natl. Acad. Sci. U.S.A 90:1086–1072, which is incorporated herewith by reference. Other modifications of the primary structure which may result in enhanced binding or selective binding of the carbohydrate bearing complement protein are also within the scope of this invention.

Carbohydrate moieties within the scope of the present invention may also include carbohydrates that by virtue of structural modifications are indicated to provide a stabilized carbohydrate moiety having a structure more resistant to metabolic degradation than the corresponding naturally occurring carbohydrate moiety. Such modified structures may also exhibit a high affinity for the particular targeted cell adhesion molecule. Thus, the carbohydrate moiety within the scope of the present invention may also encompass carbohydrates specifically designed to gain affinity for particular intercellular adhesion molecules. Such carbohydrates can be structurally modified carbohydrate or a mimetic of a carbohydrate structure such that the structural variant or mimetic has about the same or better selectin binding activity, immunogenicity, and antigenicity as the corresponding naturally occurring carbohydrate structure. Accordingly, any modification to a carbohydrate structure that enhances interactions dependent on carbohydrate structures for recognition and adhesion are within the scope of the present invention. Certain carbohydrate and carbohydrate mimetics that are structural and functional variants of the naturally occurring carbohydrates are found for instance in International Publication No. WO 93/23031, published Nov., 29, 1993, by Toyokuni, et al. Those skilled in the art of carbohydrate chemistry and carbohydrate mimetics will also recognize those structures which are suitable within the context of the present invention based on the teachings herein.

The second group of carbohydrates that interact with selectins and that are included in the present invention, are the phosphorylated mono and polysaccharides such as mannose-6-phosphate. This phosphorylated monosaccharide, as well as the high molecular weight yeast derived phosphomannon (PPME), appear to exclusively bind partners of the L-selectins, as P-selectins and E-selectins do not bind these molecules (Bevilacqua, M. P. and Nelson, R. N. (1993) J. Clin. Invest. 91:379–387).

Finally, some sulfated polysaccharides such as heparin bind to selecting (Nelson, R. M. et al., (1993) J. Clin. Invest. 91:1157–1166).

The present invention contemplates at least one discrete carbohydrate unit attached to a portion of the complement moiety. One skilled in the art will recognize that a complement protein within the scope of the invention may contain several sites of N-linked or O-linked glycosylation for the attachment of sugar moieties. Therefore, the invention is meant to include one or many carbohydrate units attached to any given complement moiety. Within a particular carbohydrate side chain of the carbohydrate moiety of the compositions, there will often be several sites for the particular primary structures to occur. For instance, the N-linked complex carbohydrates contain one or more antennary structures that are possible locations for attachment of the specific carbohydrate structures of the invention to the complement moiety, and therefore, the amount of glycosylation of a particular complement moiety may vary greatly in accordance with the biological activity one is attempting to achieve with the overall composition.

Differences in glycosylation patterns of the complement moieties are advantageous in aiding one to assess a particular composition based on its in vivo activity. Accordingly, various factors such as half-life and absorption may be assessed, and a particular composition chosen, based on these properties. Conditions that affect glycosylation include but are not limited to such parameters as media formulation, cell density, oxygenation, pH, and the like. Alternatively, one may wish to amplify a particular enzyme, such as those specific transferases involved in adding the carbohydrate residues in the appropriate position and linkage.

Several methods known in the art for glycosylation analysis are useful in the context of the present invention. Such methods provide information regarding the identity and the composition of the oligosaccharide attached to the peptide. Methods for carbohydrate analysis useful in the present invention include but are not limited to: lectin chromatography; HPAEC-PAD, which uses high pH anion exchange chromatography to separate oligosaccharides based on charge; NMR,; mass spectrometry; HPLC; GPC; monosaccharide compositional analyses; sequential enzymatic digestion. Additionally, three main methods can be used to release oligosaccharides from glycoproteins. These methods are 1) enzymatic, which is commonly performed using peptide-N-glycosidase F/endo-β-galactosidase; 2) β-elimination using harsh alkaline environment to release mainly O-linked structures; and 3) chemical methods using anhydrous hydrazine to release both N-and O-linked oligosaccharides.

Several methods presented here and known in the art are useful in determining the affinity of the molecules for the particular selectin. Generally, a number of methods can be used to assay the ability of the compositions of the inventions to inhibit intercellular adhesion mediated by selecting. The competition assays described in the Example Section, for instance, disclose specific methods. For instance, the ability of the carbohydrate-bearing complement protein to inhibit adhesion of the natural cellular ligands to the cells expressing the particular selectin can be used. Typically, the complement protein of the invention is incubated with the selectin bearing cells in the presence of the natural ligand-bearing cells, wherein the selectin-bearing cells having been immobilized on a solid support. Inhibition of the cellular adhesion is then assessed by either calculating the amount of the bound complement moiety or assessing the displaced cells. In this regard, HL-60 cells and activated human platelets and endothelial cells are especially useful.

In a preferred embodiment, the complement moiety comprises all or a portion of the complement receptor type 1, and especially any soluble fragment of complement receptor type 1 as described in Section 5.1 infra. In a particularly preferred embodiment, the complement moiety comprises sCR1. This protein, in its full-length form, has 25 sites for N-linked glycosylation. In this embodiment, carbohydrate side chains are provided on the sCR1 molecule, which chains comprise one or more carbohydrate structures that can bind to or prevent the binding of a particular ligand for an endothelial cell receptor. In particular, these carbohydrate moieties are ligand.s for selectins. In a particularly preferred embodiment, these carbohydrate moieties are the Lewis X oligosaccharides sialylated Lewis X oligosaccharides or a combination of both. One skilled in the art will understand that the amount of glycosylation may be varied from complete saturation of the available glycosylation sites to just a few of such sites.

5.3 PRODUCTION OF COMPLEMENT PROTEINS COMPRISING A SELECTIN LIGAND

The present invention provides various methods for production of the compositions disclosed and claimed herein, methods for preparation of complement protein having selectin binding activity, i.e. comprising a selectin ligand such as $Le^x$, or more preferably $SLe^x$.

5.3.1. COTRANSFECTION

As used herein, the term "cotransfection" refers to introduction of a nucleic acid encoding at least one complement moiety and at least one nucleic acid encoding an enzyme capable of transferring fucose to a lactosamine sequence. This results in co-expression of at least one complement moiety and the enzyme in the cells. Useful enzymes include the α1,3 fucosyltransferases. These enzymes useful in adding the appropriate sugars in the appropriate linkage include, but are not limited to α1,3 fucosyl transferase, α2,3 sialyl transferase, α2,6 sialyl transferase, α2,6 sialyl transferase, β1,4 galactosyl transferase, β1,3 galactosyl transferase, and β1,4 N-acetyl glucosyl transferase. These may be readily obtained from Genzyme, Inc., Cambridge, Mass., Sigma, St. Louis, Mo., the Albert Einstein College of Medicine, New York, N.Y., Biogen, Inc., Cambridge, Mass., or the like sources. Genes for such transferases are continuously being cloned and more are expected to be readily available in the future.

In a preferred method, a 1,3-fucosyl transferase has been found particularly useful for this purpose. The term "α1,3-fucosyl transferase" as used herein refers to any enzyme that is capable of forming the $Le^x$ determinant, e.g., capable of transferring fucose to the lactosamine sequence. In particular, the α1,3-fucosyl transferase of the invention can demonstrate any one of the known substrate specificities (see Harlan and Liu, Adhesion, supra). Preferably, the cell is a mammalian cell, such as COS or Chinese hamster ovary (CHO) cells.

Genes which express α1,3-fucosyl transferase can be obtained from a variety of sources (see Kukowska—Latallo et al., 1990, Genes Dev. 4:1288–1303; International Patent Publication No. WO91/16900; and Paulson & Colley, 1989, J. Biol. Chem 264:17615–17618).

The nucleic acid coding for at least one complement protein and the nucleic acid coding for the α1,3-fucosyl transferase protein can be inserted into an appropriate expression vector, or in two vectors. As used herein, the term "expression vector" refers to a vector which contains the necessary elements for the transcription and translation of the inserted protein-coding sequences. The necessary transcriptional and translational signals can be supplied by the native genes and/or their flanking regions.

A variety of host-vector systems may be utilized to express the protein-coding sequence, as long as the system provides for glycosylation of the complement moiety(ies) using the co-transfected enzyme system. Potential host-vector systems include but are not limited to mammalian cell systems infected with virus (e.g., vaccinia virus, adenovirus, etc.); insect cell systems infected with virus (e.g., baculovirus); or microorganisms such as yeast containing yeast vectors. The expression elements of vectors vary in their strengths and specificities. Depending on the host-vector system utilized, any one of a number of suitable transcription and translation elements may be used.

In one embodiment, the expression vector or vectors contains a replication origin. In an alternative embodiment, the vector or vectors, which include at least one complement moiety and at least one enzyme, are expressed chromosomally, after integration of the complement protein and the enzyme (e.g. the α1,3-fucosyl transferase) coding sequence into the chromosome by recombination. One skilled in the art will understand that it may be desirable to insert multiple genes encoding various transferase enzymes or other enzymes to ensure that at least one of the enzymes so inserted will be optimal for purposes described herein. Thus, the insertion of a multiplicity of genes encoding enzymes demonstrating a differential ability to glycosylate may be preferable to insertion of only one such gene. Also, one may desire to cotransfect more than one gene encoding a complement related protein to vary the constructs of this portion of the compositions of the invention.

Any method known in the art for the insertion of DNA fragments into a vector may be used to construct an expression vector or vectors containing at least one gene for expression of a complement protein and at least one gene for expression of an appropriate enzyme, and appropriate transcriptional/translational control signals. These methods may include in vitro recombinant DNA and synthetic techniques and in vivo recombinants (genetic recombination).

Expression of additional nucleic acid sequences encoding complement proteins or peptide fragments may be regulated by an additional nucleic acid sequence so that the complement proteins or peptides and the gene for the enzyme is expressed in a host transformed with the recombinant DNA molecule. For example, expression of a complement protein and an α1,3-fucosyl transferase may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a preferred embodiment, at least one complement protein with at least one gene for a transferase is expressed in mammalian cells and more preferably in Chinese hamster ovary (CHO) cells (See, e.g. Stanley et al., 1990, J. Biol Chem. 265:1615–1622).

In a specific embodiment, genomic DNA from cells and plasmid DNA are prepared by standard methods (Maniatis) and dissolved in Tris-EDTA (10:1) buffer. If polybrene transfection is used, the cellular genomic DNA is sheared. The cells can be transfected by either the polybrene or the calcium phosphate method (See, e.g. Stanley et al., 1990, supra).

The cotransfection can also be accomplished using the DEAE-dextran procedure (see Lowe et al., 1990, Cell 63:475–484; Davis et al., Basic Methods in Molecular Biology, Elsevier Publishing Co., 1986).

An expression vector or vectors containing at least one complement moiety and at least one nucleic acid insert for any appropriate enzyme, can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted complement protein and α1,3-fucosyl transferase gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In a specific example, if a complement protein or an α1,3-fucosyl transferase gene are inserted within the marker gene sequence of the vector, recombinants containing the inserts can be identified by the absence of the marker gene function. In the fourth approach, recombinant expression vectors can be identified by assaying for the activity of the gene product expressed by the recombinant. Such assays can be based, for example, on the physical or functional properties of the gene products in vitro assay systems, e.g., complement inhibitory activity, or binding with antibody or a selectin (see Section 5.1, supra, and Section 5.3 infra).

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; and plasmid and cosmid DNA vectors, to name but a few.

In addition, a host cell strain may be chosen which modulates the expression of the inserted sequences in addition to adding the carbohydrate moiety (e.g. a selectin ligand) or modifies and processes the gene product in the specific fashion desired. Expression from certain promoters can be elevated in the presence of certain inducers; expression of the genetically engineered complement moiety and the enzyme product may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign proteins expressed.

A vector or vectors containing at least one complement protein and at least one nucleic acid sequence encoding an appropriate enzyme are introduced into the desired host cells by methods known in the art,. e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Both cDNA and genomic sequences can be cloned and expressed.

Once a recombinant which expresses the complement protein gene or genes with the appropriate enzyme gene or genes is identified, the gene products should be analyzed. This can be achieved by assays based on the physical, immunological, or functional properties of the product.

Recovery of the expressed protein product comprising the compositions of the invention may be achieved by standard methods of isolation and purification, including chromatography (e.g., ion exchange, affinity, and sizing column chromatography, high pressure liquid chromatography), centrifugation, differential solubility, or by any other standard technique for the purification of proteins.

Any human cell can potentially serve as the nucleic acid source for the molecular cloning of the complement moiety gene or genes and the enzyme gene or genes. Isolation of the genes involve the isolation of those DNA sequences which encode a protein displaying complement protein associated structure or properties, e.g., binding of C3b or C4b or immune complexes, modulating phagocytosis, immune stimulation or proliferation, and regulation of complement. The DNA may be obtained by standard procedures known in the art from cloned DNA (e.g., a DNA "library"), by chemical synthesis, by cDNA cloning, or by the cloning of genomic DNA, or fragments thereof, purified from the desired human cell (See, for example, Maniatis et al., 1982), Molecular Cloning, A Laboratory Manual, Cold Spring Harbor Laboratory, Cold Spring Harbor, N.Y.; Glover, D. M. (ed.), 1985, DNA Cloning: A Practical Approach, NRL Press, Ltd., Oxford, U.K. Vol. I, II). Cells which can serve as sources of nucleic acid for cDNA cloning of the genes include but are not limited to monocytes/macrophages, granulocytes, B cells, T cells, splenic follicular dendritic cells, and glomerular podocytes. Clones derived from genomic DNA may contain regulatory and intron DNA regions in addition to coding regions; clones derived from cDNA will contain only exon sequences. Whatever the source, the genes should be molecularly cloned into a suitable vector for propagation of the gene.

In a preferred embodiment, the C3b/C4b receptor (CR1) protein and the Lewis X antigen are used. In a more preferred embodiment, the CR1 protein and the sialyl Lewis X antigen is used. The CR1 gene and its encoded protein are provided for in International Patent Publication No. WO89/09220 published Oct. 5, 1989 and entitled "The Human C3b/C4b Receptor (CR1)". A suitable enzyme is α1,3-fucosyl transferase, whose gene and encoded protein are provided for in Lowe et al., 1992, J. Biol. Chem. 267:4152–4160. Other genes capable of expressing α1,3-fucosyl transferases are described in International Patent Publication No. WO91/16900 Kukowska- Latallo et al., 1990, Genes Dev. 4:1288–1303, and Paulson et al., 1989, J. Biol. Chem. 264:17615–17618.

In this preferred embodiment, selection of the cells co-transfected with α1,3-fucosyl transferase that are capable of glycosylating proteins with the appropriate carbohydrate molecule can proceed by panning the cells with the CD15 structure over platelets activated with thrombin. Platelets activated with for instance, thrombin, ADP, collagen, or epinephrine, express the selectin receptors CD62/PADGEM/GMP140. Bound cells are removed in the presence of a chelating agent such as EDTA since the selectin/carbohydrate interaction is dependant on Ca++ and Mg++. These released cells are then cloned and screened for the appropriate activity. In another embodiment, the cells under consideration can be assayed for selectin binding activity in a competitive assay for binding of HL60 or U937 cells to activated platelets.

Assays for directly screening for α1,3-fucosyl transferase activity can be accomplished by a variety of means. For example, an assay can test the ability of the α1,3-fucosyl transferase to link radioactively labelled fucose to an acceptor molecule (See International Patent Publication No. WO91/16900). Assays which test for α1,3-fucosyl transferase activity are also known in the art (see Stanley et al., J. Biol Chem., 1987, 262:16830–16837, Lowe et al., 1992, J. Biol Chem. 267:4152–4160; Stanley et al., 1990, J. Biol Chem 265:1615–1622).

5.3.2. MUTAGENESIS

This invention also encompasses the use of chemical mutagenesis, by well known methods in the art, of an appropriate cell line that expresses a complement protein to yield a cell line capable of producing a composition in accordance with the present invention and preferably a composition, comprising a complement protein and selectin ligand, such as the $Le^x$ antigen, and more preferably a $SLe^x$ antigen. One suitable method envisioned in this invention is production of cell lines that express a suitable enzyme, such as α1,3-fucosyl transferase, using ethyl methane sulfonate (Stanley et al., 198:3, Somatic Cell Genetics 9:593–608).

Parental cell lines, such as CHO, which express the desired complement protein can be mutagenized at 34° C. and 38.5° C. with ethyl methane sulfonate (EMS; Eastman Chemical Co., Rochester, N.Y.) at a concentration of 100 μg/ml. Any cell line, preferably a mammalian cell line, which expresses the desired complement protein can be used, provided that mutagenesis can potentially induce one or more enzymes, such as the α1,3-fucosyl transferases, to glycosylate the complement protein. For example, cells which endogenously express the complement protein can be used, as well as transfected cells which are competent in expressing the desired complement protein. See Example Section 6.4.1. for a specific embodiment.

Other methods of mutagenesis are well known in the art and can also be used (Maniatis, Ad, supra). Additionally, the cells may be subject to irradium and mutagenized cells selected in the techniques described herein.

Methods for screening for mutagenized cells that express the compositions of the invention are known in the art and are described in Section 5.2 and the sections following this one.

5.3.3. TRANSFECTION OF CELLS HAVING APPROPRIATE ENZYME ACTIVITY WITH A COMPLEMENT PROTEIN

Cells expressing transferase enzymatic activity can be obtained from many sources. For example, cells can be used which endogenously express an appropriate enzyme such as α1,3-fucosyl transferase, or cells can be transfected with genes encoding such enzymes by the methods taught in Section 5.3.1 supra. Also, cells which have been previously mutagenized to express enzymes necessary for glycosylation with a carbohydrate moiety, such as α1,3-fucosyl transferase can be used (See Section 5.3.2 supra). or, previously transfected cells can also be used. Once cells expressing the appropriate enzyme are obtained they are transfected with the complement protein gene by methods known in the art. In particular, complement proteins are described in Section 5.1, supra; methods of introducing nucleic acids encoding such proteins into a suitable host cell that already expresses an appropriate enzyme activity are described in Section 5.3.1. , supra.

In particular, it is envisioned that a nucleic acid encoding a complement protein can be introduced into cell lines, which may then express the compositions of the invention, and especially the HL-60 (ATCC #CCL-240) and K562 (ATCC #CCL-243) cell lines.

5.3.4. CELL FUSION

Another method for obtaining the compositions of the invention is by cell fusion. The necessary competent cell lines which express an appropriate enzyme and a complement protein, i.e., as described in Section 5.3.1. through 5.3.3. supra, can be fused with each other using standard cell fusion techniques (see Current Protocols in Molecular Biology, Greene and Wiley-Interscience (1989)).

In a specific embodiment, cells that express a complement protein are fused with cells that have the enzymatic activity. A specific example of this embodiment is presented in the Example Sections below.

Preferably, when preparing the hybrid cells in accordance with such cell fusion techniques, one cell should be selected or engineered, e.g. via mutagenesis, to lack the hypoxanthine-guanine phosphoribosyl transferase gene. These cells will lack the activity to recycle purine via the salvage pathway which utilizes PRPP. These cells should be provided in excess so that fusion events will be unlikely to yield hybrid cell-lines which do not contain the mutant cells. Either cell line, e.g. the one which expresses α1,3-fucosyl transferase or the cell line which expresses complement protein, may be mutagenized. The cells which were not mutagenized will maintain the ability to utilize the salvage pathway. Therefore, only the few hybrid cell-lines which do not contain the mutagenized cell line will survive in the HAT medium (due to the presence of the aminopterin). By overwhelming the fusion with the mutagenized cells, most of the non-mutagenized cells ("normal" cells) will fuse with the mutagens, only a few of the normal cells will not have fused with the mutagens. All of the cells which result in a fusion of mutagen: mutagen will soon die off since these cells will have no means of utilizing the purine salvage pathway. Thus, this negative selection will yield hybrid cell-lines which express α1,3-fucosyl transferase activity and complement protein.

5.3.5. IN VITRO MODIFICATIONS

The necessary competent cell lines which express an appropriate complement protein as described supra, can be used as a source of the complement protein for subsequent post-production modification, modification of the existing carbohydrate structures may be accomplished using any of the appropriate enzymes described supra, at, for instance, Section 5.3.1. In a particular embodiment post-production modification occurs in vitro under the appropriate conditions using GDP-fucose and the appropriate α1,3 fucosyl transferase. Such transferases are described supra. The modification described would be expected to yield a fucosylated oligosaccharide on an existing core carbohydrate structure such as Galβ1-4 GlcNAc. The appropriate sialyl transferase along with the appropriate sialic acids would be expected to add the terminal sialic acid residues to the appropriate core structures such as Galβ1-4GlcNAc or Galβ1-4(Fucα1-4) GlcNAc. The resulting carbohydrates can be analyzed by any method known in the art including those described herein.

5.3.6. CHEMICAL MODIFICATION

The present invention further contemplates preparing the compositions of the invention by covalently coupling a carbohydrate moiety to the complement moiety using chemical synthesis techniques well known in the art.

Thus, complement protein of this invention can be glycosylated with the carbohydrate ligand by chemical modification. This modification can result in a glycoprotein in which the complement protein is directly linked to the carbohydrate ligand or, in an alternative embodiment, an inert protein that has binding activity can be covalently cross-linked to the complement protein, whereby the inert protein bridges to the carbohydrate. If such an inert protein is used, it is preferably a short consensus repeat (SCR) since the SCR is a structural motif found on many complement proteins (see Section 5.1. supra), and therefore is likely to minimally affect the structure and function of the complement protein.

As can be appreciated by one of ordinary skill in the art, a carbohydrate moiety can be purified and collected from natural sources. An example of this process is disclosed for $Le^x$ and $sLe^x$ in Stanley et al., J. Biol Chem. 263:11374 (1988), and see WO 91/19502 (PCT/US91/04284) and WO 92/02527 (PCT/US91/05416). Purified complement protein can also be obtained, as described in Section 5.1, supr. Alternatively, the carbohydrate moiety can be prepared synthetically (see Wong et al., 1992, J. Am. Chem. Soc. 114:9283, C. F. Borman, 1992, C & EN Dec. 7; p25).

The carbohydrate moiety from any source can be conjugated to the complement protein from any source, to obtain the compositions of this invention using chemical synthesis techniques. En particularly preferred embodiments, the carbohydrate moiety is Lewis X, and more preferably it is sialyl Lewis X. Preferably, the complement protein is CR1, and more preferably, soluble CR1.

The chemical cross-linking of the selectin ligand to the complement protein can proceed using a traditional cross-linking agent, such as, but not limited to molecules having one functional group that can react more than one time in succession, such as formaldehyde (although formaldehyde is not indicated for use due to its potential carcinogenicity), as well as molecules with more than one reactive group. As used herein, the term "reactive group" refers to a functional group on the cross-linker that reacts with a functional group on the complement protein so as to form a covalent bond between the cross-linker and protein. The cross-linker should have a second functional group for reacting with the carbohydrate moiety. The term "functional group" retains its standard meaning in organic chemistry. Preferably the cross-linking agent of the invention is a polyfunctional molecule, i.e., it includes more than one reactive group. The polyfunctional molecules that can be used are biocompatible linkers, i.e., they are non-carcinogenic, nontoxic, and substantially non-immunogenic in vivo. Polyfunctional cross-linkers such as those known in the art and described herein can be readily tested in animal models to determine their biocompatibility.

The polyfunctional molecule is preferably bifunctional. As used herein, the term "bifunctional molecule" refers to a molecule with two reactive groups. The bifunctional molecule may be heterobifunctional or homobifunctional Preferably, the bifunctional molecule is heterobifunctional, allowing for vectorial conjugation of the carbohydrate moiety and the complement moiety. Typically, the polyfunctional molecule covalently bonds with an amino or a sulfhydryl group on the complement protein and a hydroxyl group, an amino an aldehyde or a carboxylic acid on the carbohydrate moiety. However, polyfunctional molecules reactive with other functional groups on the complement protein, such as carboxylic acids or hydroxyl groups, are contemplated in the present invention.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde (Poznansky et al., 1984, Science 223:1304–1306) and subaraldehyde. Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionated), and their soluble bis-sulfonic acid and bis-sulfonate salts such as their sodium and potassium salts. These chemicals homobifunctional reagents are available from Pierce Chemicals, Rockford, Ill.

When a reactive group of a hetero-bifunctional molecule forms a covalent bond with an amino group, the covalent bond will usually be an amido or more particularly an imido bond. The reactive group that forms a covalent bond with amino groups may, for example, be an activated carboxylate group, a halocarbonyl group, or an ester group. The preferred halocarbonyl group is a chlorocarbonyl group. The ester groups are preferably reactive ester groups such as, for example, an N-hydroxy-succinimide ester group or that of N-maleimido-6-aminocaproyl ester of 1-hydroxy-2-nitrobenzene-4-sulfonic acid sodium salt (Mal-Sac-HNSA; Bachem Biosciences, Inc.; Philadelphia, Pa.).

Another functional group on the complement protein typically is either a thiol group, a group capable of being converted into a thiol group, or a group that forms a covalent bond with a thiol group. Free sulfhydryl groups can be generated from the disulfide bonds of a complement protein (or peptide) that contains one or more disulfides. This is accomplished by mild reduction of the protein molecule. Mild reduction conditions are preferred so that the secondary and tertiary structure of the protein is not significantly altered so as to interfere with the protein function. Excessive reduction could result in denaturation of the protein. Such reactive groups include, but are not limited to, disulfides that can react with a free thiol via disulfide transfer, e.g., pyridyl disulfide, p-mercuribenzoate groups and groups capable of Michael-type addition reactions (including, for example, maleimides and groups of the type described in Mitra and Lawton, 1979, J. Amer. Chem. Soc. 101:3097–3110). The covalent bond will usually be a thioether bond or a disulfide. The reactive group that forms a covalent bond with a thiol group may, for example, be a double bond that reacts with thiol groups or an activated disulfide. A reactive group containing a double bond capable of reacting with a thiol group is the maleimido group, although others, such as acrylonitrile, are also possible. A reactive disulfide group may, for example, be a 2-pyridyldithio group or a 5,5'-dithio-bis-(2-nitrobenzoic acid) group.

According to the present invention, for attachment to sulfhydryl groups of reduced proteins, the substrate linkers can be modified by attaching a maleimide or disulfide group to one end of the linker. The unmodified site on the linker is covalently attached to a functional group on the carbohydrate moiety. For instance, the substrate linkers which are ester or amide linked to compounds as described (Partis et al., 1983, J. Pro Chem. 2:263; Means and Feeney, 1990 Bioconjugate Chem. 1:2–12).

Some examples of heterobifunctional reagents containing reactive disulfide bonds include N-succinimidyl 3-(2-pyridyl-dithio)propionate (Carlsson, et al., 1978, Biochem J., 173:723–737), sodium S-4-succinimidyloxycarbonyl-alpha-methylbenzylthiosulfate, and 4-succinimidyloxycarbonyl-alpha-methyl-(2-pyridyldithio)toluene. Some examples of heterobifunctional reagents comprising reactive groups having a double bond that reacts with a thiol group include succinimidyl 4-(N-maleimidomethyl)cyclohexane-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, and maleimidobenzoyl-N-hydroxy-succinimide ester. Many of the above-mentioned heterobifunctional reagents and their sulfonate salts are available from Pierce Chemicals, (supra). Additional information regarding how to make and use these as well as other polyfuctional reagents that may be obtained are well known in the art. For example, methods of cross-linking are reviewed by Means and Feeney, 1990, Bioconjugate Chem. 1:2–12.

The reactive groups of the cross-linking agent can be spaced via an alkyl (including saturated and unsaturated) group, a cyclic alkyl group, a substituted alkyl or cyclic alkyl group, or an equivalent spacer group, including a peptide sequence. In a specific embodiment, the cross-linking reactive groups are spaced from 0 to about 20 atoms from each other, although spaces of more than 20 atoms are also contemplated.

In another embodiment, carbohydrate side chains of complement glycoproteins may be selectively oxidized to generate aldehydes (see, e.g., Jackson, 1944, Organic Reactions 2:341; Bunton 1965, *Oxidation in organic Chemistry*, Vol. 1 (Wiberg, ed.), Academic Press, New York, p. 367; (Cooper, et al., 1959, J. Biol. Chem. 234:445–448). This is preferred when the carbohydrate side chains are not selectin ligands. The resulting aldehydes may then be reacted with amine groups (e.g., ammonia derivatives such as a primary amine, hydroxylamine, hydrazide, hydrazide, thiohydrazide, phenylhydrazine, semicarbazide or thiosemicarbazide) to form a Schiff base or reduced Schiff base (e.g., imine, oxime, hydrazone, phenylhydrazone, semicarbazone or thiosemicarbazone, or reduced forms thereof).

Hydrazide cross-linking agents can be attached to a selectin ligand, e.g., $Le^x$ or $SLe^x$, via an ester or amide link or a carbon-carbon bond, and then reacted with an oxidized complement glycoprotein, containing an oxidized carbohydrate. This results in hydrazone formation and the covalent attachment of the compound to the carbohydrate side chain of the glycoprotein via a cross-linker group.

Alternatively, a glycoprotein form of a complement protein can be reacted with an α1,3-fucosyl transferase in the presence of fucose to yield a fucosylated form of the complement inhibitory glycoprotein.

5.4. FUNCTIONAL ACTIVITY

The present invention further provides assays for evaluating the functional activity of the compositions of the invention. In particular, the invention provides certain useful functional assays for a CR1 molecule comprising a selectin ligand such as $Le^x$, or preferably $SLe^x$. As used herein, the term "functional activity" refers to immunological binding in addition to biological functions of a molecule. Physical-chemical assays are also envisioned for determining the nature of the complement moiety and the carbohydrate moiety of the compositions of the invention.

In one embodiment, the activities of the complement moiety and the carbohydrate moiety can be evaluated separately. Thus, a complement protein comprising a carbohydrate moiety in accordance with the teachings herein may have similar or identical electrophoretic migration, isoelectric focusing behavior, proteolytic digestion maps, C3b and/or C4b and/or immune complex binding activity, complement regulatory activity, effects on phagocytosis or immune stimulation, or antigenic properties as known for the complement inhibitory protein, e.g., as described in Section 5.1, supra. Similarly, the functional activity of the carbohydrate moiety can be assayed directly, e.g., as described in Section 5.2, supra, and in International Patent Publication No. WO91/19502.

A number of currently available monoclonal antibodies can be used according to the present invention to inhibit intercellular adhesion mediated by selecting. For instance, CSLEX-1 (see, Campbell et al., J. Biol. Chem. 259:11208–11214 (1984)), VIM-2, which recognizes a sequence slightly different from $SLe^x$ (see, Macher et al., supra), FH6 (described in U.S. Pat. No. 4,904,596) (all references are incorporated herein by reference) or $SH_3$ and $SH_4$ generated by Dr. S. Hakomori of the Biomembrane Institute in Seattle, Wash.

In another embodiment, the functional activities or physical-chemical properties of the complement moiety and the carbohydrate moiety are evaluated in the same assay. For example, in a specific embodiment, the molecular weight of a complement inhibitory protein comprising a selectin ligand can be estimated by PAGE, an increase in the apparent molecular weight indicating attachment of the selectin ligand, such as $Le^x$, or preferably $SLe^x$, to the protein. In another embodiment, a sandwich immunoassay can be used to assay the functional activity. For example, by using antibodies to a complement inhibitory protein and a selectin ligand, the composition may be identified. In a specific embodiment, infra, an antibody specific for CR1 is adsorbed to an assay plate. The putative soluble CR1 comprising the selectin ligand $SLe^x$ or $Le^x$ is added to the plate under conditions that allow antibody binding. The presence of bound soluble CR1 comprising $SLe^x$ or $Le^x$ is detected by adding a $CSLE^x$ antibody or anti-CD15 antibody, respectively, labelled with FITC, followed by an anti-FITC antibody labelled with horseradish peroxidase. As will be readily understood by one of ordinary skill in the art, such sandwich immunoassay can be configured with the $CLSE^x$ antibody or anti-CD15 antibody on the solid phase, or as a direct rather than an indirect assay. In yet a further embodiment, a Western Blot assay can be used to show that the product includes a complement protein comprising a selectin ligand. In one aspect, the apparent molecular weight of a protein detected in one lane with an antibody to the complement protein and in another lane with an antibody to the selectin ligand can be compared. Results showing identical molecular weight are indicative of a positive identification of the molecule. In another aspect, the protein can be purified by affinity chromatography, either on an anti-complement protein column or an anti-selectin ligand column, and the purified protein detected on Western blotting with the alternative protein.

As can be readily appreciated by one of ordinary skill in the art, any affinity binding partner of a complement inhibitory protein or a selectin ligand of high enough affinity can be used in assays in place of specific antibody molecules.

One skilled in the art will also understand that there may be other ways the activity of the individual components of the compositions may be assayed, or the overall activity of the compositions as a whole may be assayed. These types of assays are informational with respect to achieving the desired overall functions of the compositions in a desired setting, such as the therapeutic arena. Accordingly, this Section, as well as the Examples Section, is meant to be exemplary of certain well-accepted techniques.

5.5. THERAPEUTIC COMPOSITIONS AND USES

One major advantage of the compositions of the present invention is that the carbohydrate moiety "homes" to inflamed endothelium, and thus localizes the composition to the site of tissue damage, thereby potentiating its anti-complement activity and also blocking neutrophil-endothelial cell interactions such as neutrophil rolling and extravasation. By providing for the homing of the complement protein to the site of injury, resulting in its persistence there, the claimed compositions advantageously allow for lower dosage treatment than would be possible when dosing with either of the constituents alone. The compositions of the invention may also demonstrate an increased half life in vivo and/or a great bioavailability.

Expression of selecting participates in the recruitment of cells to sites of inflammation. It is well-documented that multiple adhesion proteins and their ligands are required for the process of leukocyte adhesion to and extravasation across endothelial cells. For example, based on studies performed with known activators of the expression of ELAM-1 (inflammatory cytokines, endotoxin) and CD62 (thrombin, histamine, etc.), their expression is thought to represent inflammatory and hemostatic responses to tissue injury.

Leukocyte traffic across the vessel walls to extravascular vascular tissue is necessary for host defense against microbial organisms or foreign antigens and repair of tissue damage. Under some circumstances, however, leukocyte-endothelial interactions may have deleterious consequences for the host. During the process of adherence and transendothelial migration, leukocytes may release products such as oxidants, proteases, or cytokines that directly damage endothelium or cause endothelial damage by releasing a variety of inflammatory mediators (Harlan & Liu, supra). Some of these mediators, such as the oxidants, can directly activate complement which then feeds back to further activate the neutrophils through C3a and C5a. This leads to further tissue damage. Intervention of this process by a complement inhibitory protein "homed" into the endothelial microenvironment by its selectin interaction, could help to stop or slow down this process.

Finally, sticking of single leukocytes within the capillary lumen or aggregation of leukocytes within larger vessels may lead to microvascular occlusion and may produce ischemia. Leukocyte-mediated vascular and tissue injury has been implicated in the pathogenesis of a wide variety of clinical disorders. Inhibition of leukocyte adherence to endothelium-"anti-adhesion" therapy-represents a novel approach to the treatment of those inflammatory and immune disorders in which leukocytes contribute significantly to vascular and tissue injury. Studies in vitro indicate that close approximation of the leukocyte to the endothelial cell forms a protected microenvironment at the interface of the leukocyte and endothelial cell that is inaccessible to plasma inhibitors. Highly reactive oxidants, proteases, and phospholipase products released by adherent leukocytes at the interface can react with and damage the endothelium. Inhibition of such firm adherence prevents formation of a protected microenvironment, and thereby reduces this type of "innocent bystander" injury to endothelium. Inhibition of leukocyte adherence to endothelium will also prevent emigration to tissue, and, consequently, reduce tissue damage produced by emigrated leukocytes. Finally, inhibition of leukocyte adherence to endothelium or homotypic aggregation will prevent microvascular occlusion.

The pharmaceutical compositions of the present invention can be used to block or inhibit cellular adhesion associated with a number of disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Example of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of PMN leukocytes at sites of bacterial infection, e.g., pulmonary infiltrates in bacterial pneumonias and pus formation in abscesses).

Additionally, the pharmaceutical compositions of the present invention can be used to eliminate or block the complement injury occurring in transplanted organs. Organs prepared for transplant can be perfused with the compositions of the present invention. Alternatively, organs for transplantation may be stored in solutions containing the compositions of the present invention. Such storage can occur during, for instance, transportation. In a further embodiment, the compositions may be used to flush the area from which transplant organs are removed, as from a cadaver. Subsequent perfusion and/or storage are also envisioned.

Other treatable disorders include, e.g., rheumatoid arthritis, post-ischemic leukocyte-mediated tissue damage (reperfusion injury), frost-bit injury or shock, acute leukocyte-mediated lung injury (e.g., adult respiratory distress syndrome), asthma, traumatic shock, septic shock, nephritis, vasculitis and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma. In these embodiments, the complement moiety portion of the compositions act almost as a carrier protein.

Compositions of the invention find particular use in treating the secondary effects of septic shock or disseminated intravascular coagulation (DIC). Leukocyte emigration into tissues during septic shock or DIC often results in pathological tissue destruction. Furthermore, these patients may have widespread microcirculatory thrombi and diffuse inflammation. The therapeutic compositions provided herein inhibit leukocyte emigration at these sites and mitigates tissue damage.

The inhibitors of selectin-ligand interaction, coupled with anti-complement action, also are useful in treating traumatic shock and acute tissue injury associated therewith. Because the selectins play a role in recruitment of leukocytes to the sites of injury, particularly ELAM-1 in cases of acute injury and inflammation, inhibitors thereof may be administered locally or systemically to control tissue damage associated with such injuries. Moreover, because of the specificity of such inhibitors for sites of inflammation, e.g., where ELAM-1 receptors are expressed, these compositions will be more effective and less likely to cause complications when compared to traditional anti-inflammatory agents.

The compositions of the invention can be administered to a subject in need thereof to treat the subject by either prophylactically preventing a disease state or relieving it after it has begun. The pharmaceutical compositions of the invention may be administered in any suitable manner, including parental, topical, oral, or local (such as aerosol or transdermal) or any combination thereof. The compositions are preferably administered with a pharmaceutically acceptable carrier, the nature of the carrier differing with the mode of administration, for example, oral administration, usually using a solid carrier and I.V. administration a liquid salt solution carrier.

The compositions of the present invention include pharmaceutically acceptable components that are compatible with the patient and the protein and carbohydrate moieties of the compositions of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" preferably means approved by a regulatory agency of the Federal or a state government or listed in the U.S. Pharmacopeia or other generally recognized pharmacopeia for use in animals, and more particularly in humans.

The formulation of choice can be accomplished using a variety of the aforementioned buffers, or even excipients including, for example, pharmaceutical grades of mannitol, lactose, starch, magnesium stearate, sodium saccharin cellulose, magnesium carbonate, and the like. "Peglation" of the compositions may be achieved using techniques known to the art (see for example International Patent Publication No. WO92/16555, U.S. Pat. No. 5,122,614 to Enzon, and International Patent Publication No. WO92/00748). Oral compositions may be taken in the form of solutions, suspensions, tablets, pills, capsules, sustained release formulations, or powders. Particularly useful is the administration of the compositions directly in transdermal formulations with permeation enhancers such as DMSO. Other topical formulations can be administered to treat dermal inflammation.

A sufficient amount bf the compositions of the invention should be administered to the patient to ensure that a substantial portion of the selectin ligand expected to cause or actually causing inflammation is regulated, as well as to ensure that an optimal concentration of the complement moiety is also delivered to the site, to combat inappropriate complement-related activity. In this way, inflammation can either be prevented or ameliorated. The selection of compositions, frequency of administration, and amount of composition so administered will be in accordance with the particular disease being treated and its severity, the overall condition of the patient, and the judgement of the treating physician. Typical dosing regions will be analogous to treatment of these disease states by the use of antibodies and other biologicals. Typically, the compositions of the instant invention will contain from about 1% to about 95% of the active ingredient, preferably about 10% to about 50%. Preferably, the dosing will be between about 1–10 mg/kg. About 1 mg to about 50 mg will be administered to a child, and between about 25 mg and about 1000 mg will be administered to an adult. Other effective dosages can be readily determined by one of the ordinary skill in the art through routine trials establishing dose response curves.

In determining the dosage of compositions to be administered, it must be kept in mind that one may not wish to completely block all of the selectin receptors, or may wish to completely block such receptors for only a limited amount of time (i.e. only a few hours postischemic event). In order for a normal healing process to proceed, at least some of the white blood cells or neutrophils must be brought into the tissue in the areas where the wound, infection or disease state is occurring. Thus, amount of the composition administered as a blocking agent must be adjusted carefully based on the particular needs of the patient while taking into consideration a variety of factors such as the type of disease that is being treated. For example, one may never desire that the neutrophils reoccur in an arthritic joint, but would expect such reoccurrence at some point after a myocardial infarct, tissue crush injury, and the like.

In a preferred embodiment, the present invention contemplates pharmaceutical compositions comprising a complement inhibitory protein capable of binding to a selectin. Preferably, the pharmaceutical composition comprises a soluble CR1 molecule comprising a selectin ligand such as Le$^x$, or most preferably SLe$^x$. In one aspect, such a soluble CR1 molecule has LHRs A, B, C and D. In another aspect, such a soluble CR1 has LHRs B, C and D.

Accordingly, it is envisioned that the pharmaceutical compositions of the invention will be delivered to achieve elevation of plasma levels of the protein to treat diseases or disorders that involve inappropriate complement activity, whether or not inflammatory activity is also involved. Diseases or disorders involving complement that require systemic or circulating levels of complement regulatory proteins are detailed in Section 2.2; supra and in Table I that follows.

TABLE I

Systemic Diseases and Disorders Involving Complement

Neurological Disorders multiple sclerosis
    stroke
    Guillain Barre Syndrome
    traumatic brain injury
    Parkinson's Disease Disorders of Inappropriate or Undesirable complement Activation hemodialysis complications
    hyperacute allograft rejection
    xenograft rejection
    interleukin-2 induced toxicity during IL-2 therapy Inflammatory Disorders inflammation of autoimmune diseases
    Crohn's disease
    adult respiratory distress syndrome
    thermal injury including burns or frostbite Post-Ischemic Reperfusion Conditions mylyocardial infarction
    balloon angioplasty
    post-pump syndrome in cardiopulmonary bypass or renal bypass
    hemodialysis
    renal ischemia
    mesenteric artery reperfusion after aortic reconstruction
    transplant organ reperfusion Infectious Disease or Sepsis
Organ Preservation
Immune Complex Disorders and Autoimmune Diseases rheumatoid arthritis
    systemic lupus erythematosus (SLE)
    SLE nephritis
    proliferative nephritis
    glomerulonephritis
    hemolytic anemia
    myasthenia gravis In particular, those disorders with may be treated by systematic administration are described in section 2.2 supra.

In specific embodiments, disorders associated with extended zones of tissue destruction due to burn or myocardial infarct-induced trauma, and adult respiratory distress syndrome (ARDS), also known as shock syndrome, can be treated by parenteral administration of an effective amount of a complement inhibitory protein comprising a selectin ligand in accordance with the teachings herein.

Thus, an effective amount of a composition in accordance with the present invention is an amount effective to inhibit complement activity, in addition to its other effects.

In a preferred embodiment, the use of a complement inhibitory protein with selectin binding activity should be particularly helpful in anti-inflammatory therapy. Since the selectin ligand will home the complement inhibitory protein to the site of injury, it will prevent neutrophil rolling. This is because the selectin ligand will bind to selectins on the blood vessel wall, thus preventing the adhesion of leukocytes, particularly neutrophils.

For example, in a particularly preferred embodiment, by adding the $SLe^x$ moiety, the sCR1 activity is localized to and the site of tissue damage, thus potentiating its anti-C activity and also blocking neutrophil-endothelial cell interactions such as neutrophil rolling and extravasation.

In addition, the compositions can be used in the homing of CR1 to its ligand (the selectins) on activated endothelium, rendering lower doses more efficacious as compared to administration alone of sCR1 alone or and its present glycoforms. Heightened persistence of the $SLe^x$-sCR1 at the site of inflammation is also achieved, thereby preventing further activation. Early neutrophil adhesion events which depend on selectin/ligand interaction are also blocked. Finally, the in vivo half life and/or bioavailability of the sCR1 is prolonged.

5.6. APPLICATION IN THE DIAGNOSTIC FIELD

The compositions of the present invention can be used to constitute detection reagents capable of binding to released or shed, or circulating complexes comprising a cellular adhesion molecule. Such released, or shed or circulating adhesion molecules may be present a result of activation of a particular cell comprising a cellular adhesion molecule. It is well known that, for instance, L-selectins are constitute expressed on the surface of cells and are rapidly shed following activation (Bevilacqua, M. P., and Nelson, R. N. (1993) supra). Thus, selectins appear to be controlled by their appearance and disappearance from the surface of cells. Circulating receptors that are shed upon activation may be assayed by techniques well known to those skilled in the art. An example of such assays is found in International Patent Publication No. WO87/03600, published on Jun. 18, 1987 which is incorporated herein by reference. Such cellular adhesion molecules may be physically distinct from the receptors present on the surface of the cell as, for instance, the product of an alternative splicing event that results in a receptor that lacks certain domains necessary for attachment to the cell membrane. Alternatively, such receptors may be fragments or portions of the natural receptor, or may be associated with larger membrane fragments. Further, such receptors may be present on intact cells.

The compositions of the present invention may be useful in detecting the presence or absence of the receptors in the circulation, as in, for instance, a serum sample or other sample from a patient suspected of expressing the receptor. Alternatively, the compositions may be detectably labelled and used in in vitro or in vivo diagnostic imaging for the presence of the cellular adhesion receptors.

In certain inflammatory conditions such as reperfusion injury, septic shock, and other chronic inflammatory diseases (such as for example, psoriasis and rheumatoid arthritis), the inflamed endothelium participates in the recruitment of cells to the site of injury. Accordingly, the compositions and methods of the present invention are useful in detecting the presence or absence of such inflammatory conditions by virtue of their demonstrated ability to bind to the activated cells and displace or prevent the binding of the natural ligand. In this embodiment, the composition of the present invention are detectably labelled by techniques well known in the art.

In a further embodiment, the compositions of the present invention are immobilized on a solid support and the presence or absence of certain cellular adhesion molecules is detected by measuring or calculating thd amount of binding that occurs. In this embodiment, certain monoclonal antibodies well known in the art may be used in conjunction with the compositions.

The compositions can also be used to study inflammatory and complement mediated diseases or disorders by. virtue of their direct interaction with mediators of inflammation as described herein. In particular, the compositions can be used in either In vitro or in vivo methods. In in vitro methods the samples may be fluid specimens or tissue specimens and can include enzyme-linked assays, such as immunoperoxidase assays or staining of tissue samples.

The compositions of the invention can be used as part of a kit, especially a diagnostic kit. Such a kit may include, for instance, the compositions of the invention, as well as, components that are detectably labelled, as for instance, monoclonal antibodies to the particular cellular adhesion molecule. In one embodiment, the kit includes one or more compositions, along with the appropriate dilution and incubation buffers, a detectably labelled binding partner suitable for use in a sandwich assay format, and a substrate reagent.

6. EXAMPLE 1
6.1. GENERATION OF A SOLUBLE DELETION MUTANT OF COMPLEMENT RECEPTOR 1

The following experiments detail the generation of several soluble deletion mutants of complement receptor type 1 useful in the present invention.

6.2 GENERATION OF A SOLUBLE DELETION MUTANT OF CR1 (SCR1[DES-A]) LACKING LHR-A

Plasmid pBSABCD is described in International Patent Publication No. WO89/09220 "The Human C3b/C4b Receptor (CR1)" by Fearon, D. T., et al., published Oct. 5, 1989; (see also, Klickstein, L. B., et al., (1988) J. Exp. Med 168:1699–1717). This plasmid harbors a full-length cDNA for human CR1 inserted as a 6.86-kilobase (kb) EcoRI-EcoRV piece in the EcoRI-SmaI sites of pBluescript KS+ (Stratagene, La Jolla, Calif.); thus, the EcoRV and SmaI sites did not regenerate. pBSABCD was further modified by introducing a translational stop codon at the junction of the extracellular and transmembrane regions to yield pBL-sCR1 capable of expressing a soluble CR1 protein lacking the transmembrane and cytoplasmic domains. (International Patent Publication No. WO89/09220 "The Human C3b/C4b Receptor (CR1)" by Fearon, D. T., et al., published Oct. 5, 1989; Weisman, H. F., et al., (1990) Science 249:146–151).

pBL-SCR1 was digested with ClaI and BalI, and the resulting fragments (3.96 and 5.9 kb) were purified from low melting temperature agarose gel. Plasmid pBR322 was digested with ClaI and BalI, and the 2.9-kb fragment was purified from agarose gel and ligated to the 5.9-kb fragment from pBL-sCR1. The ligation mix was transformed into competent E. coli DH5α cells (GIBCO BRL), and the resulting plasmid, pBR8.8, was purified and digested with XbaI, generating two fragments of 7.45 and 1.35 kb. The 7.45-kb fragment was purified and religated into a circular form. The resulting plasmid, pBR7.45, was digested with ClaI and BalI, and the 4.5-kb fragment containing the CR1 cDNA was ligated to the 3.96-kb fragment from pBL-sCR1 generating pBL-sACD lacking LHR-B.

Digestion of pBL-CR1c2, also referred to as pBL-sACD (Makrides et al., (1992) *J. Biol. Chem.* 267:24754–24761) with NarI and NsiI removed 76 bp from the 3' end of the leader, the entire LHR-A, and 57 bp from the 5' end of LHRC; the 7.07 kb fragment was purified from agarose gel and ligated to two synthetic double-stranded oligonucleotides (Operon Technologies, Alameda, Calif.), 68 and 66 bp in length having the following sequence:

```
1.  5'-  CG CCC GGT CTC CCC TTC TGC TGC GGA GGA TCC
    3'-     GGG CCA GAG GGG AAG ACG ACG CCT CCT AGG

CTG CTG GCG GTT GTG GTG CTG CTT GCG GTG
         GAC GAC CGC CAA CAC CAC GAC GAA CGC GAC

CCG GTG           -3'  [SEQ ID NO. 1]
         GGC CAC CGG ACC   -5'  [SEQ ID NO. 2]

2.  5'-  GCC TGG GGT CAA TGT CAA GCC CCA GAT CAT
    3'-            CCA GTT ACA GTT CGG GGT CTA GTA

TTT CTG TTT GCC AAG TTG AAA ACC CAA ACC
         AAA GAC AAA CGG TTC AAC TTT TGG GTT TGG

AAT GCA -3'  [SEQ ID NO. 3]
         TT      -5'  [SEQ ID NO. 4]
```

(Operon Technologies, Alameda, Calif.). These oligonucleotides restored the missing sequences from both the leader and LHR-C, respectively. In addition, a single nucleotide change was designed in one of the oligonucleotides, such that the first codon of LHR-C in SCR 15 coded for glutamine, instead of the native histidine. The rationale for this modification was two-fold: (1) to ensure that the junction between the leader peptide and the coding region of the mature protein would be the same as in the native sCR1 (i.e. Glycine/Glutamine) thus avoiding potential difficulties with cleavage of the leader by signal peptidases; (2) to ensure that the N-terminal amino acid in the processed protein would be the same as in the native CR1 (Klickstein et al., (1988) J. Exp. Med. 168: 1699–1717) thus minimizing the potential for immunogenicity. The ligation mix was transformed into *Escherichia coli* strain DH5α (Gibco BRL, Gaithersburg, Md.) to produce plasmid pBL-CR1c8 containing the leader, LHR-C and LHR-D.

pBL-CR1c8 was linearized with NsiI and dephosphorylated using bacterial alkaline phosphatase (Gibco BRL) according to the manufacturer's instructions. pBL-CR1c, also referred to as pBL-sCR1 [Weisman et al., (1990) Science 249:146–151] was digested with NsiI and the 1.35 kb fragment containing most of LHR-B and the first 56 nucleotides from LHR-C was purified from agarose gel, and ligated to the linearized pBL-CR1c8. This effected the assembly of pBL-CR1c6A containing LHRs B, C, and D. The correct orientation of the BCD insert was determined by restriction digestion analysis.

The insert was excised by digestion with XhoI, and purified from agarose gel. The expression plasmid pTCSgpt (International Patent Publication No. WO89/09220 "The Human C3b/C4b Receptor (CR1)" by Fearon, D. T. et al., published Oct. 5, 1989; Carson et al., (1991) J. Biol. Chem. 266: 7883–7887) was digested with XhoI, dephosphorylated using bacterial alkaline phosphatase, and ligated to the BCD fragment. The ligation mix was transformed into *E. coli* DH1, generating plasmid pT-CR1c6A. The correct insert orientation was determined by BglI restriction digestion, and pT-CR1c6A was prepared on large scale. pT-CR1c6A is a plasmid which harbors the coding sequence for the soluble deletion mutant of CR1 lacking the LHR-A as well as the transmembrane and cytoplasmic domains. The resulting soluble deletion mutant is termed sCR1[des-A] containing LHR's B, C, and D.

7. EXAMPLE 2

7.1 CONSTRUCTION OF A SOLUBLE DELETION MUTANT OF CR1 CONTAINING SCR'S 15–18

A DNA fragment composed of the CR1 leader and Short Consensus Repeats (SCR) 15 through 18 was PCR-synthesized using pBL-CR1c8 as template [Makrides et al. (1992) *J. Biol. Chem.* 267, 24754–24761]. The 5' "sense" primer hybridized to the pBluescript polylinker region upstream of the CR1 leader, and contained an XhoI restriction site, underlined:

5'-CCCCCC<u>CTCGAG</u>GTCGACGGTATCGATAAGC-3' [SEQ ID NO. 5]

The 3' "antisense" primer contained restriction enzyme recognition sequences for BglII and NotI sites, underlined:

5'-TATCAAATG<u>CGGCCGC</u>TAAGAATACCCT <u>AGATCT</u>GGAGCAGCTTGGTAACTCTGGC-3' [SEQ ID NO. 6]

The resulting 980-bp fragment was digested with XhoI and NotI, and ligated into pBluescript KS(+) (Stratagene, La Jolla, Calif.) previously restricted with XhoI and NotI. The ligation mix was transformed into *E. coli* DH5α competent cells (GibcoBRL, Gaithersburg, Md.) to yield plasmid pB-CR1(15–18) (3.86 kb). This was linearized at the 3' terminus of SCR 18 using BglII, and blunt-ended with mung bean nuclease (New England Biolabs, Beverly, Mass.) used according to the manufacturer's recommendations. The linearized plasmid was ligated to a synthetic double-stranded oligonucleotide (Operon Technologies, Inc., Alameda, Calif.) composed of the following two complementary strands:

5'-GATGAACTAGTCTCGAGAG-3' [SEQ ID NO. 7]
5'-CTCTCGAGACTAGTTCATC-3' [(SEQ ID NO. 8]

The double-stranded oligonucleotide restored the missing base-pairs from the 3' terminus of SCR 18, and introduced a translational stop codon, followed by SpeI and XhoI restriction sites. The Ligation mix was transformed into *E. coli* DH5α competent cells yielding plasmid pB-CR1 (15–18A) (3.88 kb).

The DNA fragment composed of the CR1 leader and SCR 15–18 was excised from pB-CR1(15–18A) by digestion with XhoI, purified from agarose gel using the Geneclean Kit (BIO 101, La Jolla, Calif.), and ligated to the expression vector pTCSgpt [Carson et al., (1991) *J. Biol. Chem.* 266, 7883–7887] previously restricted with XhoI and dephosphorylated with calf intestinal alkaline phosphatase (Boehringer Mannheim, Indianapolis, Ind.). Transformation of the ligation mix into *E. coli* DH1 competent cells yielded plasmid pT-CR1c12 (8.52 kb).

7.2 TRANSFECTION AND SELECTION OF STABLE CELL LINES pT-CR1c12 was linearized by FspI digestion, phenol-extracted, ethanol-precipitated and resuspended in sterile water. 30 µg of recombinant plasmid was cotransfected with 3 µg pTCSdhfr [Carson et al., (1991) *J. Biol. Chem.* 266, 7883–7887] into CHO DUKX-B11 cells deficient in dihydrofolate reductase [Urlaub and Chasin (1980) *Proc. Natl. Acad. Sci. USA* 77, 4216–4220] using electroporation with the Gene Pulser (Bio-Rad) at 960 µF and 230 V. The transfected cells were transferred to non-selective α-Minimum Essential Medium (α-MEM) supplemented with 10% heat-inactivated fetal bovine serum, 1% penicillin-streptomycin, 50 μg/ml gentamicin, 4 mM glutamine (Gibco BRL), 10 μg/ml each of thymidine, adenosine, and deoxyadenosine (Sigma, St. Louis, Mo.). After two days the cells were selected in α-MEM supplemented with 10% dialyzed fetal bovine serum, 1% penicillin-streptomycin, 50 μg/ml gentamicin, 4 mM glutamine, 20 mM HEPES pH 7.0, 6 μg/ml mycophenolic acid, 250 μg/ml xanthine, and 15 μg/ml hypoxanthine (Sigma). Clones secreting SCR 15–18 were identified by enzyme immunoassay (Cellfree® CD35; T Cell Sciences, Inc.), and the complement inhibitory activity of the proteins was confirmed using hemolytic assays [Yeh et al., (1991) *J. Immunol.* 146, 250–256]. High-expressing clones were selected in growth media containing methotrexate (Lederle, Pearl River, N.Y.).

8. EXAMPLE 3
8.1 CONSTRUCTION OF A SOLUBLE DELETION MUTANT OF CR1 LACKING LHR D (sCR1[des-D])

Plasmid pBSABCD was obtained from Dr. Douglas Fearon [Klickstein et al., (1988) *J. Exp. Med.* 168, 1699–1717]. This plasmid harbors a full-length cDNA for human CR1 inserted as a 6.86 kilobase (kb) EcoR1-EcoRV piece in the EcoR1-SmaI sites of pBluescript KS+ (Stratagene, La Jolla, Calif.); thus, the EcoRV and SmaI sites did not regenerate. pBSABCD was further modified as described [Weisman et al., (1990) *Science* 249, 146–151] to yield pBL-sCR1 capable of expressing a soluble CR1 protein lacking the transmembrane and cytoplasmic domains.

An unique NruI restriction site was introduced in pBL-sCR1 at position 4200 basepair (bp), i.e., at the junction of LHR-C and -D. The enzyme site was engineered by site-directed mutagenesis [Kunkel (1985) *Proc. Natl. Acad. Sci. USA* 82, 488–492] using the Muta-gene Phagemid Kit (Bio-Rad Laboratories, Melville, N.Y.). The 40-base phosphorylated mutagenic oligonucleotide (New England Biolabs, Beverly, Mass.) had the following sequence:

3'CGACACTTGAAAGACAAGC<u>GC</u>
<u>TACCAGTGACA</u>TTTTGGGG5' [SEQ ID NO. 9]

The underlined bases are those which differ from the wild-type sequence. DNA templates were sequenced by the dideoxynucleotide chain termination method [Sanger et al., (1977) *Proc. Natl. Acad. Sci. USA* 74, 5463–54673] using the Sequenase kit (U.S. Biochemical, Cleveland, Ohio).

The mutagenized plasmid pBL-sCR1N (9.8 kb) was digested with NruI and BglII, and the 7.8 kb fragment was isolated from agarose and ligated to a double-stranded synthetic oligonucleotide composed of the following complementary strands:

5'-CGCTTAAGCTCGA-3' [SEQ ID NO. 10]
5'-GATCTCGAGCTTAAGCG-3' [SEQ ID NO. 11]

The double-stranded synthetic oligonucleotide restored the missing base pairs from the 3' terminus of SCR 21 (LHR C), and introduced a translational stop codon followed by XhoI and BglII restriction sites. The resulting plasmid pBL-CR1c7 (7.8 kb) was digested with XhoI, and the insert was ligated into the expression vector pTCSgpt [Carson et al., (1991) *J. Biol. Chem.* 266, 7883–7887] previously restricted with XhoI and dephosphorylated with bacterial alkaline phosphatase (GibcoBRL, Gaithersburg, Md.) used according to the manufacturer's recommendations. Transformation of the ligation mix into *E. coli* DH1 competent cells yielded plasmid pT-CR1c7.

Transfection and Selection of Stable Cell Lines.

pT-CR1c7 was linearized by FspI digestion, phenol-extracted, ethanol-precipitated and resuspended in sterile water. 30 μg of recombinant plasmid was cotransfected with 3 μg pTCSdhfr [Carson et al., (1991) *J. Biol. Chem.* 266, 7883–7887] into CHO DUKX-B11 cells deficient in dihydrofolate reductase [Urlaub and Chasin (1980) *Proc. Natl. Acad. Sci. USA* 77, 4216–4220] using electroporation with the Gene Pulser (Bio-Rad) at 960 μF and 230 V. The transfected cells were transferred to non-selective α-Minimum Essential Medium (α-MEM) supplemented with 10% heat-inactivated fetal bovine serum, 1% penicillin-streptomycin, 50 μg/ml gentamicin, 4 mM glutamine (Gibco BRL), 10 μg/ml each of thymidine, adenosine, and deoxyadenosine (Sigma, St. Louis, Mo.). After two days the cells were selected in α-MEM supplemented with 10% dialyzed fetal bovine serum, 1% penicillin-streptomycin, 50 μg/ml gentamicin, 4 mM glutamine, 20 mM HEPES pH 7.0, 6 μg/ml mycophenolic acid, 250 μg/ml xanthine, and 15 μg/ml hypoxanthine (Sigma). Clones secreting sCR1[desD] LHR's A, B, and C were identified by enzyme immunoassay (Cellfree® CD35; T Cell Sciences, Inc.), and the complement inhibitory activity of the proteins was confirmed using hemolytic assays [Yeh et al., (1991) *J. Immunol.* 146, 250–256]. High-expressing clones were selected in growth media containing methotrexate (Lederle, Pearl River, N.Y.).

9. EXAMPLE 4
9.1 GENERATION OF SOLUBLE CONSTRUCTS OF CR1 CONTAINING THE SLEX CARBOHYDRATE MOIETY

Any of the foregoing soluble deletion mutants of CR1 or other complement moiety as defined herein can be manipulated to contain a carbohydrate moiety useful within the scope of the present invention. The following examples describe the generation of sCR1[des-A]sLe$^x$ a soluble deletion mutant of CR1 lacking LHR-A and containing the sLex carbohydrate moiety.

9.1.1. TRANSFECTION OF THE sCR1[des-A] CONSTRUCT INTO LEC-11 CELLS

Following linearization by FspI restriction digestion, pT-CR1c6A (Example 1, Section 6.2, Supra) was cotransfected into LEC11 cells (Campbell, C., and Stanley, P., 1984, *J. Biol. Chem.* 259:11208–11214) with FspI-linearized pTCSdhfr* containing an altered mouse dihydrofolate reductaise, cDNA that displays an abnormally low affinity for methotrexate (Simonsen, C. C. and Levinson, A. D. (1983) Proc. Natl. Acad. Sci. USA 80: 2495–2499). Clones secreting sCR1[desA]sLe$^x$ were identified by enzyme immunoassay (Cellfree CD35; T Cell Diagnostics, Inc.), and the complement inhibitory activity of the protein was confirmed using hemolytic assays (Yeh et al., (1991) J. Immunol. 146: 250–256). High-expressing clones were selected in growth media containing methotrexate (Lederle, Pearl River, N.Y.).

9.1.2 Cell Culture Droduction of sCR1[des-A]sLe$^x$.

CHO DUKX-B11 cells secreting sCR1[desLHR-A] or CHO LEC-11 cells secreting sCR1[desLHR-A]sLe$^x$ were grown in T-225 flasks in 1:1 Dulbecco's modified Eagle's medium with high glucose/Ham's nutrient mixture F12 without hypoxanthine and thymidine (JRH Biosciences, Lenexa, Kans.) supplemented with 2.5% heat-inactivated fetal bovine serum (Hyclone, Logan, Utah). The pH of the media was adjusted to 7.8 to using sodium bicarbonate to minimize sialidase activity present in the conditioned medium. The conditioned medium from these cultures was harvested three times a week by decanting, filtered, and frozen at −70° C. until purification. Productivity was monitored by ELISA.

9.1.3 Purification of sCR1[desA]sLe$^x$.

Filtered cell culture supernatants containing sCR1[desA] sLe$^x$ or SCR1[des-A] were buffer exchanged and concentrated by cross-floaw ultrafiltration (30,000 molecular weight cut-off), filtered again, applied to a S-Sepharosa Fast Flow cation exchange column, and eluted with a high salt concentration (0.5 M sodium chloride). The cation exchange eluant was precipitated with ammonium sulfate, separated by centrifugation, resuspended in PBS, and filtered. The filtrate was adjusted to 0.8 M ammonium sulfate, loaded on a Butyl-Toyopearl 650M column and eluted with a step to 0.09 M ammonium sulfate. The eluant was concentrated using Centriprep-30 concentrators (Amicon), subjected to size exclusion chromatography on a Toyopearl HW55F column, again concentrated using Centriprep-30 concentrators, sterile filtered, and stored frozen at −70° C. The purification process was monitored by absorbance at 280 nm and by ELISA. Protein purity was examined by SDS-PAGE with either Coomassie Blue or silver staining and scanning densitometry. Endotoxin levels were determined using the Limulus Amebocyte Lysate assay (Associates of Cape Cod, Inc., Woods Hole, Mass.).

10. EXAMPLE 5
10.1 IN VITRO COMPLEMENT REGULATORY ACTIVITY OF SCR1[des-A]SLEX AND SCR1[des-A]

The in vitro regulatory activities of sCR1[des-A]sLe$^x$ were compared to those of sCR1[des-A], which is the same protein except lacking sLe$^x$ glycosylation and which has been shown to selectively inhibit alternative complement activation in vitro. sCR1[desA]sLe$^x$ was constructed and expressed in LEC11 cells, and purified from cell culture supernatants as described in the previous examples. sCR1 [des-A] was constructed as described above and expressed in CHO DUKX-B11 cells as described above for sCR1[des-A]sLex except that pT-CR1c6a was cotransfected into DUKX-B11 with FspI-linearized pTCSdhfr. sCR1[des-A] was purified from cell culture supernatants as described above for sCR1[des-A]sLex.

sCR1[desA]sLe$^x$ and sCR1[des-A] competed equally for the binding of dimeric C3b to erythrocyte CR1. sCR1[des-A]sLe$^x$ and sCR1[des-A] were equivalent in their capacity to serve as a cofactor in the factor I mediated degradation of the C3b α-chain. sCR1[des-A]sLe$^x$ and sCR1[des-A] were equivalent in their capacity to inhibit alternative complement mediated erythrocyte lysis using C4-deficient guinea pig serum as a complement source. sCR1[des-A]sLe$^x$ and sCR1[des-A] were equivalent inhibitors of complement mediated erythrocyte lysis under conditions which allow classical pathway activation. Both, however, were significantly less effective inhibitors of classical pathway mediated hemolysis than sCR1, a soluble recombinant protein containing the entire extracellular sequence of CR1. Thus, sCR1[desA]sLe$^x$, like sCR1[des-A], is a selective inhibitor of alternative complement pathway in vitro.

10.1.1 Complement Proteins and Antibodies.

Human C4, C3, C3b, and chemically cross-linked dimeric C3b (C3b2) were prepared as described previously (Makrides et al., 1992, Scesney et al., Eur. J. Immunol., 1996, 26:1729–1735). C4 was treated with methylamine to produce C4ma, a C4b-like form of the protein (Makrides et al., 1992; Law and Levine, 1980). C3b, C3b$_2$, and C4ma were radiolabeled with $^{125}$I using Iodo-beads (Pierce Chemical Co.) according to the manufacturer's recommendations. C4 deficient guinea pig serum was obtained commercially (Sigma).

10.1.2 C3b$_2$ Binding Studies.

The binding of sCR1[desA]sLe$^x$ and sCR1[des-A] to $^{125}$I-C3b$_2$ was assessed by competition with native CR1 on human erythrocytes (Weisman et al., 1990; Makrides et al., 1992). Human erythrocytes were diluted with an equal volume of Alsever's solution (113 mM dextrose, 27 mM sodium citrate, 2.6 mM citric acid, 72 mM sodium chloride, pH 7) and stored at 4° C. until use. There was no difference in C3b$_2$ binding to freshly drawn erythrocytes and those stored in Alsever's solution. Immediately prior to use, erythrocytes were washed three times with PBS, 0.1% BSA, and 0.01% sodium azide. $^{125}$I-C3b$_2$ (0.55 nM) was incubated with erythrocytes (4×10$^9$ cells/ml) for 60 min on ice (0° C.) in the presence of varying concentrations of sCR1, sCR1[des-A], sCR1[des-A]sLex C3b$_2$, or C3b. Bound and free $^{125}$I-C3b$_2$ were separated by centrifugation through dibutyl phthalate. Nonspecific binding was determined in the presence of 0.71 mg/ml purified rabbit anti-sCR1 antibody.

RESULTS

C3b$_2$ Binding Studies.

The competition of sCR1[des-A], sCR1[des-A]sLex and sCR1 with $^{125}$I-C3b$_2$ binding to erythrocyte CR1 was assessed. From the concentration of competitor required to inhibit maximal $^{125}$I-C3b$_2$ binding by 50%, apparent dissociation constants ($K_{d,app}$) for sCR1, C3b$_2$, and C3b were estimated to be 2×10$^{-9}$ M, 3×10$^{-8}$ M, and 6×10$^{-7}$ M, respectively, values which are similar to results obtained in earlier studies (Weisman et al., 1990; Wong and Farrel, 1991; Makrides et al., 1992). sCR1[des-A]sLe$^x$ or sCR1 [des-A] compete equally for $^{125}$I-C3b$_2$ binding to erythrocyte CR1.

10.1.3 Cofactor Activity for Proteolysis of Fluid Phase C3b or C4ma by Factor I.

The capacity of sCR1[desA]sLe$^x$ or sCR1[des-A] to promote the specific proteolysis of the C3b or C4ma α-chain was assessed on SDS-PAGE (Wong et al., 1985; Weisman et al., 1990; Scesney et al., Eur. J. Immunol., 1996, 26:1729–1735). $^{125}$I-C3b (6.8×10$^{-9}$ M) or $^{125}$I-C4ma (5.6× 10$^{-8}$ M) was incubated in PBS with factor I (0.25 μM) and varying concentrations of either sCR1[des-A]sLe$^x$ or sCR1 [des-A] for 20 min at 37° C. followed by 5 min on ice (0° C.). Under these conditions the proteolysis of the C4ma C3b α-chain was dependent on the concentration of cofactor. The remaining intact C3b α-chain was separated on reduced SDS-PAGE and the bands were cut out and measured in a γ-counter.

RESULTS

Cofactor Activity for the Factor I Proteolysis of the C3b α-chain and of the C4ma α-chain.

The specific proteolysis of $^{125}$I-C3b or $^{125}$I-C4ma by factor I was monitored on SDS-PAGE under conditions in which the extent of α-chain cleavage was dependent on the concentration of cofactor, either sCR1[des-A]sLe$^x$ or sCR1 [des-A]. The loss of the band representing the intact C3b α-chain required similar concentrations of either sCR1[des-A]sLe$^x$ or sCR1[des-A]. The loss of the band representing the intact C4ma α-chain also required similar concentrations of either sCR1[des-A]sLe$^x$ or sCR1[desLHR-A]. It can be concluded that sCR1[des-A]sLe$^x$ and sCR1[des-A] were equivalent in their capacity to serve as a cofactor in the Factor I mediated degradation of the C3b α-chain.

10.1.4 Hemolytic Assay for Inhibition of Classical and of Alternative Complement Activation.

The inhibition of complement activation was assessed as previously described (Weisman et al., 1990; Yeh et al., 1991). Sheep erythrocytes sensitized with rabbit anti-sheep erythrocyte antibodies (Diamedix, Miami, Fla.) were lysed using human serum as a complement source in 100 mM HEPES, 150 mM sodium chloride, 0.1% BSA, pH 7.4. Sensitized sheep erythrocytes ($10^7$ cells/ml), normal human serum (1 in 400 dilution), and varying concentrations of sCR1[des-A] or sCR1[des-A]sLe$^x$ were incubated for 60 min at 37° C. in V-bottom microtiter plates, the cells pelleted by centrifugation, and the supernatants transferred to a flat bottom microtiter plate and the absorbance at 405 nm determined in order to guantitate released hemoglobin. Samples were paired with identical controls lacking human serum (complement-independent lysis). Both samples and controls were run in triplicate. Control values were subtracted from sample values and the fractional inhibition was determined relative to the uninhibited (no added sCR1[des-A]sLe$^x$ or sCR1[des-A]) sample.

The inhibition of alternative pathway hemolysis was assessed using the modified method of Platts-Mills and Ishizaka (1974). Rabbit erythrocytes were lysed using C4 deficient guinea pig serum as complement in 100 mM HEPES, 0.15 N sodium chloride, 0.1% bovine serum albumin, pH 7.4 with added EGTA and $Mg^{2+}$ to 8 mM and 5 mM, respectively. Rabbit erythrocytes ($1.2 \times 10^7$ cells/ml), C4 deficient guinea pig serum (1 in 8 dilution), and sCR1[des-A]sLe$^x$ or sCR1[des-A] were incubated 60 min at 37° C. in a V-bottom microtiter plate, and released hemoglobin was determined as before.

Inhibition of Heinolysis by the Alternative Complement Pathway Using C4-deficient Guinea Pig Serum.

To rule out interference from either pre-existing or newly generated C4b, the alternative pathway lysis of rabbit erythrocytes was examined using C4-deficient guinea pig serum as a complement source. Equivalent concentrations of sCR1, sCR1[des-A], or sCR1[desA]sLe$^x$ were required to inhibit alternative complement-mediated erythrocyte lysis.

Inhibition of Hemolysis Initiated by the Classical Complement Pathway.

The inhibition of complement lysis of antibody-sensitized sheep erythrocytes required approximately equivalent concentrations of sCR1[desA]sLe$^x$ or sCR1[desLHR-A]. These concentrations, however, were approximately 50-fold higher than those required for inhibition by sCR1 which contains LHR's A, B, C, and D.

11. EXAMPLE 6
11.1 ANALYSIS of sCR1[des-A]sLex

In this Example the the purified proteins sCR1[des-A] and sCR1[des-A]sLex are compared in Western blot analysis.

11.1.1 ANTIBODIES sCR1 was prepared as previously described (Weisman et al., 1990; Yeh et al., 1991). Polyclonal rabbit anti-sCR1 antibodies were prepared and purified as described (Makrides et al., 1992). CSLEX-1 (anti-sialyl Lewis$^x$) was obtained from Becton Dickinson. FH6 (anti-sialyl di-Le$^x$) was obtained from Dr. S. Hakomori (Biomembrane Institute, Seattle Wash.). DREG-56 (anti-E-selectin) was obtained from Endogen, Cambridge, Mass.; anti-CD15 (anti-Lex)was obtained from AMAC (Westbrook, Me.

11.1.2 Western Blot Analysis of sCR1[desA]sLe$^x$.

Western Blot analysis was conducted acccording to the following procedure:

a) glycoproteins obtained from the transfection of LEC-11 cells with the sCR1[des-A] construct described above were run subjected to SDS polyacrylamide gel electrophoresis under reducing and non-reducing conditions with appropriate controls and standards.

b) the glycoprotein bands were transferred to solid support membranes (Immobilon™) via semi-dry electrophoretic transfer (Integrated Separation Systems)

c) the membranes containing the transferred glycoproteins were blocked with 1% non-fat dry milk proteins for 2 hrs., (or overnight) or other blocking reagents such as bovine serum albumin (at about 2.0%) and gelatin (at about 0.3%). The latter blocking reagents are preferable to avoid complications due to potential SLe$^x$ glycosylated proteins present in the milk solution (such as IgA).

d) the replicate membranes were then reacted with antibodies to CR1 and/or sCR1[des-A], antibodies to Lex (DAKO, AMAC, CD15), antibodies to SLe$^x$(CSLEX-1, available from ATCC, and from Becton Dickinson), and isotype matched control antibodies for 2hrs.

e) the membranes were washed in wash buffer(PBS-tween) 4 times for about 10–15 minutes each.

f) the membranes were then reacted with HRP-labelled anti-murine antibodies or anti-rabbit antibodies (all available from various vendors such as Bio-rad, Southern Biotech, Tago) for 2 hrs.

g) the membranes were washed as in (e).

h) the membranes are developed with HRP subtrate (Bio-rad, Sigma) to visualize the glycoprotein bands reactive with each primary antibody, or, a chemilumincescent method referred to as "ECL" (Enhanced Chemiluminescence, Amersham).

RESULTS
11.2 Western Blot Analysis.

The above-described technique using the ECL Western Blot procedure from Amersham and antibodies to SLe$^x$ (CSLEX1) and antibodies to CR1 (rabbit polyclonal antibodies) was performed using the material derived from LEC-11 cells transfected with the complement moiety termed sCR1[des-A] obtained through the method described above to yield sCR1[desA] sLe$^x$. The results of this Western Blot analysis clearly demonstrated that sCR1[desA]sLe$^x$ derived from LEC-11 cells (Pamela Stanley, Albert Einstein College of Medicine) bears sLe$^x$ moieties as determined by staining with CSLEX1 antibodies, (ATCC HB 8580, see U.S. Pat. No. 4,752,569) while material derived from transfection of the sCR1[des-A] construct into DUKX.B11 CHO cells does not.

Figure 1A:
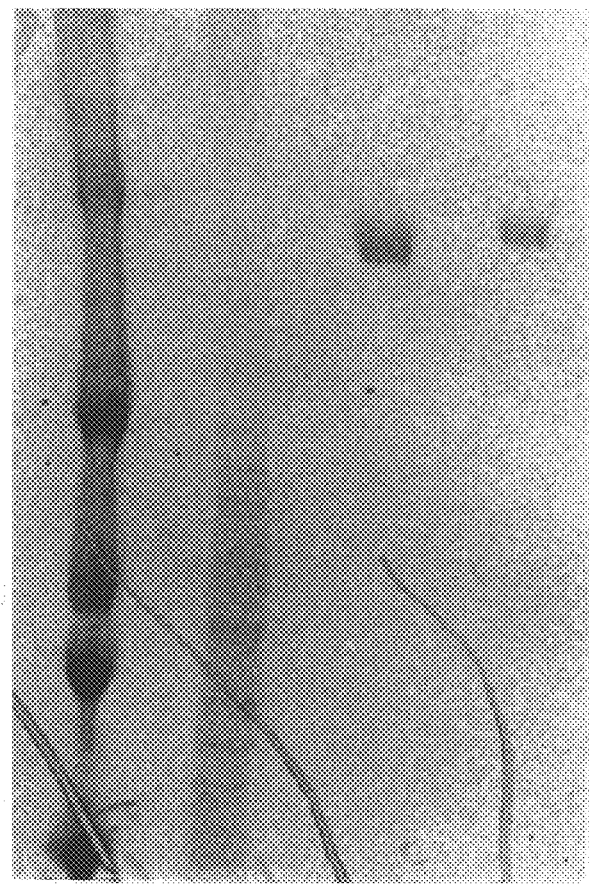
FIG. 1B Shows a chemiluminescence Western blot of the same gel as described in A probed with CSLEX1, an antibody that reacts with the sLe$^x$ carbohydrate determinant. Lane 4 (which contains a soluble form of sCR1 containing LHR's BC and D (sCR1[des-A]sLex recovered from LEC-11 cells) shows two distinct bads representing different glycosylation forms of the sCR1[des-A]sLex.
FIG. 1C Is the same gel described in Figure B, stripped and probed with affinity purified rabbit polyclonal antibody to CR1. The blot shows that the two glycosylation forms of sCR1[des-A] from Gel B above are also reactive with the anti-complement receptor type 1 antibodies.
Figure 1B:
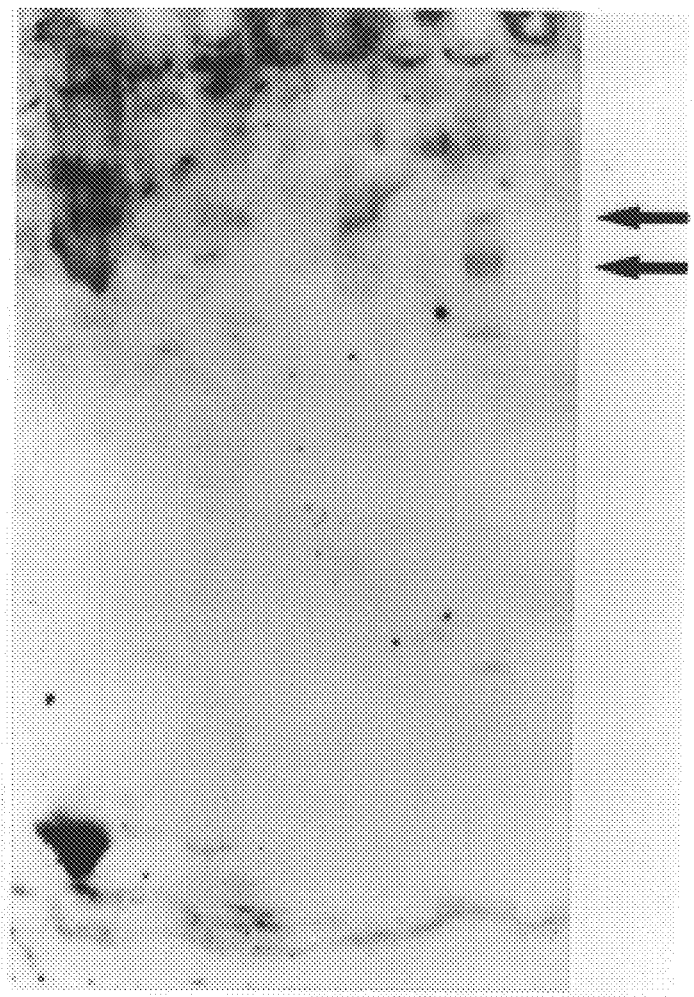
Figure 1C:
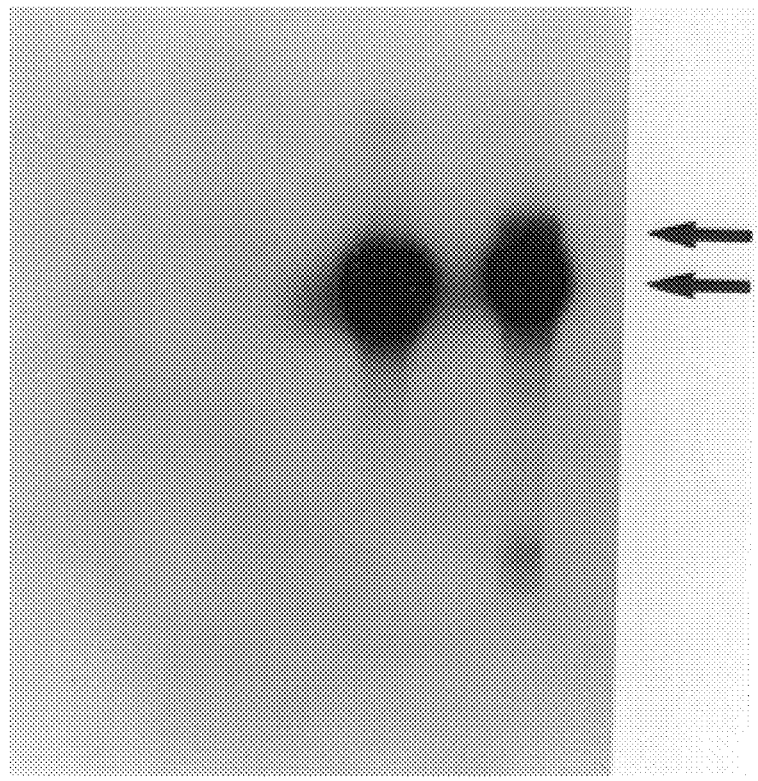

FIG. 1B shows the results of this analysis, the first lane with material in it contains molecular weight standards. The second lane contains lysate derived from HL-60 cells (positive control for CSLEX1 mAb). The third lane contains sCR1[des-A] material derived from DUKX.B11 CHO cells and the fourth lane contains sCR1[des-A]sLe$^x$ material derived from LEC-11 cells. Of the two lanes containing the sCR1[des-A] material, only that lane derived from LEC-11 cells (Lane 4) was identified by the CSLEX1 mAb as demonstrated by two clear bands consistent with two glycosylation forms of sCR1[des-A]. Both lanes containing sCR1[des-A] (Lane 3 from DUX.B11, and Lane 4 from LEC-11) reacted with a polyclonal antibody to sCR1[des-A] as expected (FIG. 1C). FIG. 1A is a coomasie-blue stained SDS-PAGE gel in the same material.

11.3 SECOND WESTERN BLOT ANALYSIS

In a separate experiment sCR1[desLHR-A] and sCR1 [desA]sLe$^x$ were subjected to SDS-PAGE using a 4–20% gel (ISS) and non-reducing conditions. The gels were blotted onto a membrane (Immobilon-P) using a semi-dry transblotting apparatus (ISS). The membranes were blocked overnight at room temperature in a solution of tris buffered saline (TBS) containing 2% BSA, 1% normal goat serum, 0.05% sodium azide. The blot was probed with FH6 (anti-sialyl di-Le$^x$, Hakomori supernatant, diluted 1:1 in TBS blocking buffer) for 2 h at room temperature. After extensive washing in PBS with 0.05% Tween-20, the blot was probed with horseradish peroxidase (HRP) conjugated goat anti-mouse IgM (Tago, 1 ug/ml in blocking buffer) for 1 h at room temperature. After extensive washing in PBS with 0.05% Tween-20, the blot was incubated with a chemi-luminescent substrate (ECL kit, Amersham) for 1 minute, exposed to x-ray film for 30–120 s, and the film developed. The blot was then stripped and re-probed with rabbit polyclonal anti-sCR1 (1:2000 in blocking buffer) for 1 h, washed extensively, probed with HRP conjugated anti-rabbit Ig (Amersham), washed and detected as before.

RESULTS OF THE SECOND WESTERN BLOT ANALYSIS

In the second western blot analysis both CSLEX-1, a monoclonal antibody that reacts with sLe$^x$ oligosaccharides, and FH60, a monoclonal antibody that reacts with sialyl di-Le$^x$, bound to sCR1[desA]sLe$^x$ but not to sCR1[desA]. Both oligosaccharide structures have been shown to be ligands for selectins (Goelz, S. et al., J. Biol. Chem. (1994) 269:1033–1040). Parekh et al. (1992) J. Biochem. (Tokyo) 16d,137, identified the carbohydrate strucures responsible for binding to an E-selectin affinity column to be sialyl di-Le$^x$. No insight into the number of N-linked glycosylation sites used, or how many of those terminate in sLe$^x$, can be derived from this experiment.

FIGS. 2A through 2C detail the results of the second Western blot experiment. FIGS. 2A through 2C are an analysis of the same polyacrylamide gel. In lane 1 of each Figure are the molecular weight standards. Lane 2 of each Figure is the purified sCR1[des-A] material obtained from DUKX-B11 cells. Lane of 3 each is an irrelevant control material. Lanes 4, 5 and 6 of each gel are sCR1[des-A]sLex at varying stages during the purification procedure.

FIG. 2A is a coomassie blue stained polyacrylamide gel pattern. The predominant bands at approximately 187 kd in lanes 2, and 4–6 are the sCR1[des-A] protein, lane 2 obtained from DUKX-B11 cells and lanes 4–6 obtained from LEC-11 cells. FIG. 2B is the same gel as FIG. 2 Western blotted and probed with and anti-sCR1[des-A] polyclonal serum. As expected, all lanes containing sCR1-[des-A], whether derived from DUKX-B11 cells or LEC-11 cells are positive for sCR1[des-A]. FIG. 2C is the same blot as FIG. 2B stripped and reprobed with an antibody specific for the sialyl di-Lewis x antigen represented by the short-hand notation NeuNAcα2-3Galβ1-4(Fucα1-3)GlcNAcβ1-3Galβ1-4(Fucα1-3)GlcNAc. As expected, only lanes 4–6 containing sCR1[des-A]sLex obtained from LEC-11 cells are positive for the appropriate carbohydrate structure.

12. EXAMPLE 7
12.1 MONOSACCHARIDE COMPOSITION OF SCR1 [DES-A] IS CONSISTANT WITH SLE$^x$ GLYCOSYLATION

The monosaccharide composition of the glycans comprising the carbohydrate moiety of the sCR1[des-A]sLex were analyzed using gas-liquid chromatography (GLC) following the procedure of Reinhold, V. (1972), Methods in Enzymology, 25:244–249. The conditions of cleavage, derivitization and GLC provided for a quantitative determination of the monocaccarides comprising the the glycoproteins sCR1[des-A] and sCR1[des-A]sLex.

The CHO line utilized for the expression of sCR1 and sCR1[desLHR-A], CHO DUKX-B11, lacks α(1,3)fucosyl transferase activity and is thus incapable of sLex glycosylation. Stanley and colleagues have generated a mutant CHO cell line, LEC11, which transcribes endogenous alpha(1–3) fucosyltransferases and can synthesize carbohydrates with fucosylated terminal structures, including sLe$^x$.

In this example, LEC11 cells capable of sLe$^x$ glycosylation have been transfected with the plasmid encoding sCR1 [desLHR-A] to produce sCR1[desA]sLe$^x$. The sCR1[des-A] sLe$^x$ was compared to sCR1[des-A] produced in DUKX-B11 cells. When the two glycoproteins where analyzed for monosaccharide composition the results presented in Table I below were obtained:

TABLE I

|      | sCR1[des-A] |     | sCR1[des-A]sLex |     |
| ---- | ----------- | --- | --------------- | --- |
|      | % Wt        | MR  | % Wt            | MR  |
| Fuc  | 1.4         | 1.1 | 2.7             | 1.9 |
| Man  | 4.1         | 3.0 | 4.7             | 3.0 |
| Gal  | 3.6         | 2.6 | 4.7             | 3.0 |
| GlcN | 7.5         | 4.4 | 8.9             | 4.6 |
| NA   | 2.7         | 1.1 | 4.5             | 1.7 |

The values presented in Table I for % Wt are the percentage of the particular sugar relative to the total protein. The MR is the molar ratio normalized to mannose. Fuc = fucose, Man = mannose, Gal = galactose, GlcN = N-acetyl-glucosamine, NA = sialic acid.

It can be concluded from Table I that the fucose and sialic acid content of the sCR1[des-A]sLex are consistent with the expectation that the Lec 11 cell line is adding the appropriate carbohydrates necessary for the sialylated Lewis x antigen as well as the sialylated di-Lewis x antigen.

sLe$^x$ is the carbohydrate ligand for both P- and E-selectin and thereby mediates leukocyte adherence at vascular sites of inflammation. sCR1[desA]sLe$^x$ thus combines the anti-inflammatory potential of both a complement regulatory protein and an adhesion molecule.

13. EXAMPLE 8
13.1 MASS SPECTROSCOPY OF THE OLIGOSACCHARIDES FROM SCR1[DES-A]SLEX IS CONSISTANT WITH SLEX GLYCOSYLATION

Mass spectroscopy confirmed the presence of fucose and sialic acid containing carbohydrates consistent with sLex glycosylation. Electron microspray (Fenn et al., (1989) Science, 246:64–71) followed by mass spectroscopy provided an assessment of the N-acetylneuraminic acid groups (sialic acid), fucosylation, and partial insight into antenna extensions and branching. In this Example sCR1[des-A] sLex was endo-H deglycosylated and an ES-MS "fingerprint" was obtained and compared to a similar "fingerprint" obtained from an endo-H deglycosylated sCR1[des-A] glycoprotein.

Carbohydrates were grouped into bi- tri- and tetra antennary structures each having the typical trimannose core structure.

In the resulting ion profile each ion was accounted for by reference to composition-mass tables compiled for each monosaccharide. The ion m/z 1062.8 found in the sCR1 [des-A]sLex "fingerprint", for instance, represents a biantennary structure consistant with a preferred sLex carbohydrate moiety and can be accounted for as fucosylated sialylated Lewis x antigen of the following structure:

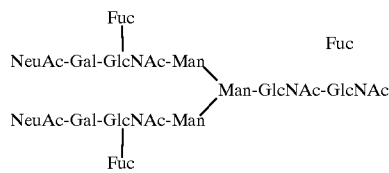

The corresponding structure with equivalent m/z is absent in the "fingerprint" analysis of sCR1[des-A].

The data in Table II represents the percent mole ratio of each of the particular carbohydrate structures present in the sCR1[des-A] and sCR1[des-A]sLex compostions.

TABLE II

| Glycoform* | sCR1 | sCR1[des-A] | sCR1[des-A]sLex |
|---|---|---|---|
| BiNA$_0$ | 49.6 | 31.9 | 8.4 |
| BiNA$_0$F$_1$ | — | — | 3.6 |
| BiNA$_0$F$_2$ | — | — | 1.7 |
| BiNA$_1$ | 19.6 | 27.0 | 15.8 |
| BiNA$_1$F$_1$ | — | — | 10.9 |
| BiNA$_1$F$_2$ | — | — | 4.6 |
| BiNA$_2$ | 4.0 | 13.0 | 9.0 |
| BiNA$_2$F$_1$ | — | — | 9.6 |
| BiNA$_2$F$_2$ | — | — | 4.8 |
| TriNA$_0$ | 7.4 | 5.4 | 1.6 |
| TriNA$_0$F$_1$ | — | — | <1 |
| TriNA$_0$F$_2$ | — | — | <1 |
| TriNA$_1$ | 4.0 | 3.8 | 4.1 |
| TriNA$_1$F$_1$ | — | — | 1.9 |
| TriNA$_1$F$_2$ | — | — | <1 |
| TriNA$_2$ | 1.7 | 2.7 | 4.3 |
| TriNA$_2$F$_1$ | — | — | 3.5 |
| TriNA$_2$F$_2$ | — | — | <1 |
| TriNA$_3$ | 1.1 | 2.7 | 2.7 |
| TriNA$_3$F$_1$ | — | — | 2.0 |
| TriNA$_3$F$_2$ | — | — | <1 |
| TetraNA$_0$ | 1.8 | 1.3 | — |
| TetraNA$_1$$^\#$ | 1.8 | 1.6 | 1.2 |
| TetraNA$_2$$^\#$ | <1 | 1.3 | 1.9 |
| TetraNA$_3$$^\#$ | <1 | <1 | 1.6 |
| TetraNA$_4$$^\#$ | <1 | <1 | 1.3 |
| BiNA$_0$-(Gal) | 5.5 | 4.8 | 1.9 |
| BiNA$_1$-(Gal) | <1 | 1.8 | <1 |
| BiNA$_0$-(Fuc) | 1.7 | 1.5 | <1 |

*core fucosylated; approx. 3% are non-fucosylated
including sialyl lewis(x) in TP18

ES-MS analisys of sCR1[desA]sLe$^x$-derived oligossaccharide structures is consistent with sLe$^x$ glycosylation.

14. EXAMPLE 9
14.1 FUNCTIONAL ACTIVITY OF sCR1[des-A]sLex IN VITRO

In this Example the functional activities of the purified proteins sCR1[des-A] and sCR1[des-A]sLex are compared in vitro. sCR1[desA]sLe$^x$ inhibited E-selectin mediated binding of U937 cells to activated human aortic endothelial cells in a concentration-dependent manner in vitro. In this static adhesion assay, sCR1[desA]sLe$^x$ inhibited binding of U937 cells by 50% at a final concentration of 250 ug/ml.

14.1.1 Static Adhesion Blocking Assay.

Aortic endothelial cells (Clonetics), confluent in 96-well microtiter plates, were stimulated with TNF (100 U/ml) for 4 h at 37° C. The cells were then washed twice with DNEN supplemented with 1% FBS. Serial dilutions of sCR1[desA]sLe$^x$ and sCR1[desLHR-A] were made to achieve final concentrations of 500, 250, 125, 62.5, and 0 ug/ml. To each well, 5×10$^5$ U937 (obtained from ATCC) cells in 20 μl of DMEM were added and incubated for 20 min at 37° C. The wells were filled with media, sealed, and centrifuged inverted at low speed (150×g) for 5 min. The seal was removed, the plates blotted, and the number of bound cells in three microscope fields was determined.

14.2 RESULTS

Using this in vitro static adhesion assay, sCR1[desA]sLe$^x$ inhibited E-selectin mediated adhesion in a concentration-dependent manner. Human aortic endothelial cells were stimulated with TNF to induce cell surface expression of E-selectin. Surface expression of E-selectin was determined using DREG-56 (a monoclonal antibody specific for E-selectin) in an immunocytochemical staining protocol. U937 cells, shown to have surface sLe$^x$ by flow cytometric analysis with CSLEX-1, were shown to adhere to the activated endothelial cells. The adherence phenomenon between the activated aortic endothelial cells and U937 cells was shown to require the presence of calcium, a hallmark of selectin-mediated adhesion. The E-selectin dependent adhesion of U937 cells to activated endothelial cells was inhibited by sCR1[desA]sLE$^x$ in a concentration dependent manner.

FIG. 3 details the results of this experiment. The black bars represent the sCR1[des-A] material obtained from DUKX-B11 cells. The bars with horizontal lines represent sCR1[des-A]sLex material obtained form LEC-11 cells. The sCR1[des-A]sLex material inhibited binding of U937 cells to activated aortic endothelial cells in a concentration dependent manner.

15. EXAMPLE 10
15.1 IN VIVO FUNCTIONAL ACTIVITY OF sCR1[des-A]sLex

Endothelial upregulation of selecting, to which oligosaccharides such as sialyl Lewis$^x$, and sialyl di-Lex bind, are important adhesion promoting molecules for neutrophils. The soluble complement receptor 1 (sCR1), which is a potent inhibitor of complement, has been expressed in a truncated form, with and without decoration with SLe$^x$ (sCR1[desA]sLe$^x$ and sCR1[desA], respectively). Both compounds have substantial complement-blocking activity in vitro as demonstrated above. In a rat model of P-selectin-dependent acute lung injury, the rank order of protective activity for these inhibitors is: sCR1[desA]sLe$^x$>sCR1≧sCR1[desA]. By taking advantage of oligosaccharide decoration of sCR1[desA] to cause binding to the activated endothelium at sites of selectin expression, the complement inhibitor can be "targeted" to an inflammatory site.

The inhibitor preparations were employed in vivo in the CVF model of rat lung injury. Four separate groups of rats (n=5 each) were pretreated intravenously with 0.4 ml sterile saline, sCR1, sCR1[desA] or sCR1[desA]sLe$^x$ (each at 15 mg/kg body weight) and injected intravenously 5 min before intravenous infusion of CVF. Also, a negative control group (infused with sterile saline in the absence of CVF) was employed (n=5). Thirty min. after infusion of CVF or sterile saline, animals were killed with an overdose of ketamine and 1.0 ml blood obtained from the inferior vena cava (a).

As shown by the data in FIG. 4, treatment of animals with sCR1[desA], sCR1[desA]sLe$^x$ or sCR1 reduced (as a percentage) MPO content in lung by 40±3, 64±3 and 55±4, respectively (FIG. 4C). FIG. 4C is a measure of the accumulation of neutrophils in the lung as estimated by measurement of myeloperoxidase activity (MPO). When compared statistically, sCR1[desA]sLe$^x$ and sCR1 were more effective than sCR1[desA] in reducing MPO content.

FIG. 4B also describes the protective effects of sCR1, sCR1[des-A], and sCR1[des-A]sLex from hemorrhagic lung injury induced by CVF. FIG. 4B is the measurement of the reduction over control of hemorrhage as measured by a radiolabelled red blood cell leakage into the lung from the blood vessel. sCR1[des-A]sLex reduced hemorrhage approximately 65 percent over control. Permeability is a measure of radiolabelled protein leakage from the blood vessels of the lung. sCR1[des-A] reduced permeablity approximately 60 5 over control in this experiment. Thus, sCR1[desA]sLe$^x$ appears to be the most effective of the three complement inhibitors in reducing injury in this inflammatory model.

At the time of sacrifice (30 min after intravenous infusion of CVF), plasma was obtained and evaluated for the concentration of sCR1[desA] antigen using an ELISA sandwich technique. Plasma from CVF infused animals that were otherwise untreated revealed <50 ng/ml measurable sCR1 [desA] antigen, while plasma antigenic levels of sCR1 [desA] in the sCR1[desA] and sCR1[desA]sLe$^x$ treated animals (injected with CVF) were 267±28.2 and 154±33.9 µg/ml, respectively. These data would be consistent with an accelerated selectin-dependent removal of sCR1[desA]sLe$^x$ from the vascular compartment.

These data demonstrate that, in the P-selectin-dependent model of acute lung injury occurring after CVF-induced systemic activation of complement, the complement inhibitor, sCR1[desA] decorated with sLex groups provides the most effective protection (as compared to sCR1[desA] or sCR1) in this model of neutrophil-dependent injury. Reduced MPO content in lung suggests that sCR1[desA] sLe$^x$ more effectively blocked P-selectin-dependent adhesion of neutrophils to the activated endothelium, which is known to be upregulated for P-selectin. Each of three complement inhibitors had protective effects that were associated with diminished buildup of lung MPO.

By reducing the amount of endothelial activation (upregulation of P-selectin) and diminishing neutrophil activation (resulting in generation of toxic oxygen products), complement blockage interferes with injury-promoting interactions between neutrophils and the endothelium. In this model of lung injury it is known that both neutrophils and toxic oxygen products are required for full development of injury. The close proximity between neutrophils and the endothelium is required for the most effective action of toxic oxygen products (from neutrophils) on the endothelium. These adhesive interactions can be blocked with antibodies to P-selectin or leukocytic β2 integrins, ox by infusion of sLe$^x$. In all cases the protective effects of these interventions are associated with diminished levels of tissue MPO. The enhanced inhibitory activity of sCR1[desA]sLe$^x$ would be consistent with the interpretation that, as CVF-induced complement activation occurs (thus causing endothelial upregulation of P-selectin), sCR1[desA]sLe$^x$ can selectively bind to endothelial P-selectin, providing localized protection against further complement activation. Localization of sCR1 [desA]sLe$^x$ to areas of activated endothelium is supported by the immunostaining data and could also explain why residual plasma levels of sCR1[desA] antigen at 30 min were nearly 50% lower in sCR1[desA]sLe$^x$ treated animals than those treated with sCR1[desA].

The ability to "target" complement inhibitors to the endothelium based on the ability of sLex to cause binding of sCR1[desA]sLe$^x$ to P-selectin (or to E-selectin) provides a unique strategy to optimize the protective effects of these inhibitors. Since ischemia-reperfusion injury to the myocardium appears to be P-selectin-dependent, it is possible that in humans treatment of ischemia-reperfusion injury would benefit from the use of such inhibitors, as well as other conditions in which selectin and complement activation molecules participate in outcomes leading to injury.

16. EXAMPLE 11

16.1 GENERATION OF A SOLUBLE COMPLEMENT RECEPTOR TYPE 1 WITH SELECTIN BINDING ACTIVITY

We describe herein another soluble form of complement receptor type 1 with selectin binding activity. This bifunctional molecule is a valuable tool in modulating the inflammatory response.

16.1.1. CELL LINES

The cell line K562 was supplied by Dr. Lloyd Klickstein, Center for Blood Research, 200 Longwood Avenue, Boston, Mass. 02115, and is generally available for the American Type Culture collection (Rockville, Md.). HL-60 cells were obtained from the ATCC.

16.1.2. MONOCLONAL ANTIBODIES

Rabbit polyclonal antiserum specific for CR1 can be obtained by standard techniques known in the art by immunizing rabbits with human complement receptor type 1. Monoclonal antibodies to CD15 are commercially available and can be obtained from Dako, California and for instance, clone 28 may be obtained from AMAC, Inc., Maine. Murine monoclonal antibody 3C6. D11 was obtained from a standard fusion using the method originally described by Kohler and Milstein (1975, Nature 256:495–497). Balb/c mice were immunized at 3–4 week intervals with purified recombinant complement receptor type 1 i.p. in Freunds adjuvant. Four weeks after the third immunization, mice were boosted intravenously with 10 µg CR1 and the spleen was removed four days later. Splenocytes were fused with NSO myeloma cells by addition of 1 ml of 50% PEG-1500 (Boehringer Mannheim, Indianapolis Ind.), then diluted with 20 ml of OPTI-MEM media (GIBCO). After fusion, the cells were plated into wells of 96 well flat bottomed plates and selected in medium containing HAT (GIBCO). Wells positive for growth were screened for the production of anti CR1 mAbs using a CR1 capture antibody. Control antibodies were murine IgM and murine IGg1, commercially available from Becton Dickinson, Franklin Lakes, N.J., and Tago, Calif.

16.1.3. TRANSFECTION

K562 cells expressing complement receptor type 1 (CR1) can be obtained by transfecting host cells by electroporation with full length CR1 obtained from construct piABCD (Klickstein, et al., 1988, 168:1699). Approximately five million K562 cells suspended in 0.8 ml medium are mixed with approximately 20 µg plasmid DNA, linearized with SpeJ, and subjected to 200 volts, 960 µF using a genepulser electroporation apparatus (BioRad). After several days in culture cells expressing the soluble CR1 gene product can be selected for the expression of soluble CR1 using the CELL-FREE® CD35 Bead Assay Kit obtained from T Cell Diagnostics, Inc. Cambridge, Mass.

Alternatively, the calcium phosphate-mediated transfection of K562 cells can be accomplished using the method of Graham and van der Erb (1973) Virology 52:456–467.

16.1.4. CELL LYSATES

Cell lines transfected to express the appropriate molecules or cell line endogenously expressing the appropriate molecules were solubilized at 5×107 cells/ml in lysis buffer containing 10 mM Tris pH 8.0, 1% nonidet P-40 (NP-40), 10 mM iodoacetamide (IAA), 1 mM phenylmethly sulfonyl fluoride (PMSF), 0.04% aprotinin and 0.3 mM N-tosyl-L-phenylalanine chloromethyl ketone (TPCK).

16.1.5. WESTERN BLOT ANALYSIS

The reactivity of CR1 purified by affinity chromatography from K562 supernatants was tested by Western blot analysis. Supernatants from K562 transfected with the full length CR1 were fractionated by 4–20% SDS-PAGE and then transferred to nitrocellulose sheets. The sheets were first blocked with blocking buffer (1% bovine serum albumin in phosphate-buffered saline in PBS). After blocking, the sheets were incubated with either antibody 3C6. D11 about 2–3 µg/ml(anti-CR1), anti-CD15 (about 20 µg/ml, or irrelevant isotype matched control antibody C305 (IgM, about 20 µg/ml), or W112 (IgG, about 2–5 µg/ml). After 1–2 hour incubation in the presence of the primary antibodies the sheets were washed with a solution of PBS and 0.05% Tween-20. After washing the sheets were incubated with horseradish peroxidase (HRP) conjugated goat anti-mouse antibody. After washing, color was developed with an HRP substrate, 16.2. RESULTS As expected, the material recovered from the K562 cell culture supernatants can be detected by Western blot using antibodies to the Lewis X antigen as well as monoclonal anti-CR1 antibodies.

16.3. PHYSICAL CHARACTERIZATION OF KCR1

To define the specific carbohydrate structures of the KCR1 recovered supra both affinity purified KCR1 and neuraminidase treated KCR1 were tested for their ability to bind anti-CR1 immobilized on wells of 96 well plates. Detection was with an anti-CD15 antibody which is reactive with the Lex $SLe^x$ ligand structures. Treatment of the KCR1 with neuraminidase removes terminal sialic acid residues from the $SLe^x$ oligosaccharide structures yielding the Lewis X structure. Results of this analysis are presented in Table III.

TABLE III

Reactivity of KCR1 with anti-CD15 Antibody

| Test Sample | Bound ($OD_{490-650}$) Monoclonal Antibody |
|---|---|
| CR1[1] | 0.059 ± 0.002 |
| KCR1[2] | 0.135 ± 0.001 |
| nKCR1[3] | 0.130 ± 0.006 |
| KCR1[4] | 0.110 ± 0.024 |

All samples are the mean plus or minus the standard deviation of the mean for four samples excluding the control which is the average of two samples.

[1] CR1 represents a sample of CR1 obtained from Chinese Hamster ovary cells which does not contain appropriate carbohydrate structures for binding the CD15 antibody.
[2] KCR1 represents a sample of affinity purified CR1 produced in K562 cells. The sample was concentrated by a Centricon™ concentrator prior to assay
[3] nKCR1 represents a sample of CR1 produced in K562 cells which was treated with neuraminidase. Neuraminidase treatment consisted of incubating the sample in the presence of neuraminidase prior to assay.
[4] KCR1 represents a sample of CR1 affinity purified from K562 cells and untreated prior to assay.

17. GENERALIZED ASSAY FORMATS TO DETECT FUNCTIONAL ACTIVITY

The compositions of the invention may also be evaluated for their ability to block intercellular adhesion to certain cells, for instance, activated endothelial cells thereby inhibiting a primary event in the inflammatory response. This evaluation may be achieved by a number of methods; the following methods being described as specific procedures that were employed in this regard or that may be useful in addition thereto:

A. COMPETITIVE INHIBITION OF HL-60 BINDING TO E AND P SELECTINS a) cells expressing E or P selectin(activated platelets or cells transfected with and expressing selectins on their surface, ref Larsen,et al.) are grown in 96-well microtiter plates to confluence.

b) HL-60 cells are added at 4 deg Centigrade in the presence or absence of CR1 or CR1 analogues and allow to settle and bind for 30 min.

c) non-adherent cells are removed by inverting the plates and centrifuging at 150 xg for 5 min.

d) the plates are scored for the number of bound HL-60 cells per microscope field.

B. IN VIVO ASSAY FOR SELECTIN BINDING a) induce P-selectin up-regulation in rats with CVF in accordance with the method of Mulligan et al., 1992, J. Clin. Invest. 90: 1600–1607.

b) inject radio-labelled sLEX-CR1 chimera or analogues vs TP10 and determine distribution of radiolabel.

C. IN VIVO ASSAY FOR COMPOSITION EFFICACY

Mulligan et al.("Role of Leukocyte Adhesion Molecules in Complement-Induced Lung Injury", J. Immunol. Vol. 150, 2401–24061, No. 6, Mar. 15, 1993,) describe the role of P selectin in lung vascular endothium injury in rats after cobra venom factor (CVF) activation of complement. Since it has previously been shown that complement has a protective effect in preventing acute microvascular injury of the lung induced by CVF, it is desirable to home the CR1 to the site of the injury via the selectin ligand. In order to assess the localization of the complement, twenty units of CVF per kg body weight is injected intravenously into male 300–350 gram Long Evans rats. To assess the localization of the CR1 to the lung $^{125}$I-CR1-$sLe^x$ (approximately 500 µCi), or in control animals $^{125}$I-CR1 is injected at for instance 15 mg/kg body weight. Since CVF induced lung injury is instantaneous, localization can be assessed by assessing tissue incorporation of radiolabelled CR1-$sLe^x$ by standard techniques approximately 30 minutes after injection.

The CVF model can also be used to assess the ability of the sLexto prevent the primary events in inflammation such as neutrophil sequestration and subsequent rolling and firm attachment. See also, Mulligan et. al., Role Endothelial-Leukocyte Adhesion Molecule 1 (ELAM-1) in Neutropnil-Mediated Lung Injury in Rats, J. Clin. Invest., Vol. 88, October 1991, 1396–1406, and Mulligan et al., "Neutrophil-dependent Acute Lung Injury," J. Clin. Invest., Vol. 90, October 1992, 1600–1607.

18. OTHER TECHNIQUES FOR PREPARATIONS OF COMPOSITIONS 18.1. MUTAGENESIS

CHO (Chinese hamster ovarian) cells that express sCR1 are used. The cells in suspension (at about $2 \times 10^5$ cells/ml) can be incubated for 18 hrs with EMS, washed, and relative plating efficiencies determined. Mutagenized cells may be cultured for seven days to allow expression of acquired mutations. Cells can be aliquoted at about $10^6$ cells/100-mm tissue culture dish in medium containing about 10% fetal calf serum and the appropriate concentration of the primary selective lectin(s). After six days, the plates are washed twice with alpha medium and the scondary selective lectin (s) added in alpha medium containing 10% fetal calf serum. After approximately four more days of incubation, the largest colonies are picked into alpha medium containing 10% fetal calf serum and the plates stained with 2% methylene blue in 50% methanol. Control plates which contained no lectin or only the primary selective lectin(s) are stained after 8 days and relative plating efficiencies determined.

18.2. CELL FUSION

Approximately $1 \times 10^8$ cells expressing the α1,3-fucosyl transferase and $5 \times 10^7$ cells expressing the desired complement protein which have been previously suspended in DMEM, were pelleted by centrifugation at 200×g for 5 minutes and warmed to 37° C. The pellet was resuspended in 1 ml of culture medium containing about 1 g/ml of polyethylene glycol (PEG) 4000, supplemented with 5% DMSO at 37° C. with gentle mixing. The cells wee then spun at 100×g for 2 minutes, 4.5 ml of supplemented medium was added over the next 3 minutes followed by 5 ml of supplemented medium over the next two minutes. Then the tube was filled with supplemented medium. As is well known in the art, timing of these steps is important.

The cells were pelleted by centrifugation at 100×g for 5 min at room temperature, then the supernatant was aspirated. The cell pellet was resuspended in medium, but care was taken not to force the dispersion of small cell clumps. The cells were plated in a 96-well plate in limiting dilution (To ensure growth, the wells of the plate may contain feeder cells). Culture medium containing mycophenolic acid was added, and then replaced as often was deemed necessary to ensure cell selection. Cells expressing sLex or sialyl di-Lex are then selected.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A pharmaceutical composition comprising a soluble complement receptor 1 polypeptide selected from the group consisting of sCR1 and sCR1 lacking LHR-A bound to a carbohydrate structure which is a selectin ligand in admixture with a pharmaceutically acceptable carrier, wherein said soluble complement receptor 1 polypeptide inhibits a primary event in the inflammatory response.

2. The pharmaceutical composition of claim 1 wherein said selectin ligand is a Lewis X antigen.

3. The pharmaceutical composition of claim 2 wherein said selectin ligand is a sialyl Lewis X antigen.

4. The pharmaceutical composition of claim 1 wherein the soluble complement receptor 1 polypeptide blocks intercellular adhesion.

5. The pharmaceutical composition of claim 1 wherein the soluble complement receptor 1 polypeptide binds a cellular adhesion molecule.

6. The pharmaceutical composition of claim 1 wherein the soluble complement receptor 1 polypeptide binds to activated endothelial cells.

7. A conjugate comprising at least one soluble complement receptor type 1 (CR1) polypeptide selected from the group consisting of sCR1 and sCR1 lacking long homologous repeat-A (LHR-A) bound to at least one carbohydrate structure which is a selectin ligand which conjugate inhibits a primary event in the inflammatory response.

8. The conjugate of claim 7 in which the conjugate blocks intercellular adhesion.

9. The conjugate of claim 7 in which the conjugate binds to a cellular adhesion molecule.

10. The conjugate of claim 7 in which the conjugate binds to activated end of endothelia cells.

11. The conjugate of claim 7 in which the selectin ligand is selected from the group consisting of ligand of E-selectin P-selectins, and L-selectins.

12. The conjugate of claim 7 in which the conjugate binds to an E-selectin.

13. The conjugate of claim 7 in which the conjugate binds to a P-selectin.

14. The conjugate of claim 7 in which the conjugate binds to an L-selectin.

15. The conjugate of claim 7 in which said conjugate binds to a lectin domain within said selectin and has a binding affinity of at least about $10^4 M^{-1}$.

16. The conjugate of claim 7 in which said at least one carbohydrate is an N-linked carbohydrate.

17. The conjugate of claim 16 in which the N-linked carbohydrate is fucosylated.

18. The conjugate of claim 16 in which the carbohydrate structure comprises an oligosaccharide related to the Lewis X carbohydrate.

19. The conjugate of claim 18 in which the carbohydrate comprises the Lewis X carbohydrate.

20. The conjugate of claim 17 in which the N-linked carbohydrate is sialylated.

21. The conjugate of claim 20 in which the carbohydrate structure comprises the sialyl Lewis X carbohydrate.

22. The conjugate of claim 7 in which the soluble complement receptor polypeptide comprises at least LHR B, LHR C, and LHR D up to and including the first alanine residue of the transmembrane region of complement receptor type 1.

23. A soluble complement inhibitory protein comprising a soluble CR1 polypeptide selected from the group consisting of sCR1 and sCR1 lacking LHR-A, which polypeptide bears a carbohydrate structure which is a selectin ligand, wherein said soluble complement inhibitory protein inhibits a primary event in the inflammatory response.

24. The complement inhibitory protein of claim 23 in which the selectin ligand is a Lewis X antigen.

25. The complement inhibitory protein claim 24 in which the Lewis X antigen is a sialyl Lewis X antigen.

26. The soluble complement inhibitory protein of claim 23 wherein the protein blocks intercellular adhesion.

27. The soluble complement inhibitory protein of claim 23 wherein the protein binds a cellular adhesion molecule.

28. The soluble complement inhibitory protein of claim 23 wherein the protein binds to activated endothelial cells.

* * * * *